US009193794B2

(12) United States Patent
Lin et al.

(10) Patent No.: US 9,193,794 B2
(45) Date of Patent: Nov. 24, 2015

(54) ANTIBODIES RECOGNIZING A CARBOHYDRATE CONTAINING EPITOPE ON CD-43 AND CEA EXPRESSED ON CANCER CELLS AND METHODS USING SAME

(75) Inventors: Rong-Hwa Lin, Los Altos, CA (US); Leewen Lin, Taipei (TW); Shih-Yao Lin, Taipei (TW); Shu-Hua Lee, Taipei (TW)

(73) Assignee: BioAlliance C.V., Alkmaar (NL)

( * ) Notice: Subject to any disclaimer, the term of this patent is extended or adjusted under 35 U.S.C. 154(b) by 701 days.

(21) Appl. No.: 12/690,846

(22) Filed: Jan. 20, 2010

(65) Prior Publication Data

US 2010/0124551 A1    May 20, 2010

Related U.S. Application Data

(62) Division of application No. 11/811,303, filed on Jun. 7, 2007, now Pat. No. 7,674,605.

(60) Provisional application No. 60/811,850, filed on Jun. 7, 2006.

(51) Int. Cl.
*A61K 39/00* (2006.01)
*C07K 16/28* (2006.01)
*C07K 16/30* (2006.01)
*A61K 39/395* (2006.01)

(52) U.S. Cl.
CPC ......... *C07K 16/2896* (2013.01); *C07K 16/3007* (2013.01); *A61K 39/39558* (2013.01); *A61K 2039/505* (2013.01); *C07K 2316/96* (2013.01); *C07K 2317/24* (2013.01); *C07K 2317/34* (2013.01); *C07K 2317/56* (2013.01); *C07K 2317/73* (2013.01)

(58) Field of Classification Search
CPC ............... A61K 39/39558; A61K 2039/505
USPC ............. 530/350, 387.3, 387.7, 388.1, 388.8, 530/391.3, 391.7; 424/130.1, 133.1, 138.1, 424/143.1, 154.1, 155.1, 181.1, 183.1
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 4,676,980 A | 6/1987 | Segal et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 5,047,335 A | 9/1991 | Paulson et al. |
| 5,219,740 A | 6/1993 | Miller et al. |
| 5,278,299 A | 1/1994 | Wong et al. |
| 5,314,995 A | 5/1994 | Fell, Jr. et al. |
| 5,422,120 A | 6/1995 | Kim |
| 5,500,362 A | 3/1996 | Robinson et al. |
| 5,510,261 A | 4/1996 | Goochee et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,677,427 A | 10/1997 | Goldenberg et al. |
| 5,693,761 A | 12/1997 | Queen et al. |
| 5,693,762 A | 12/1997 | Queen et al. |
| 5,733,743 A | 3/1998 | Johnson et al. |
| 5,750,373 A | 5/1998 | Garrard et al. |
| 5,772,997 A | 6/1998 | Hudziak et al. |

(Continued)

FOREIGN PATENT DOCUMENTS

| | | |
|---|---|---|
| AU | 37570/93 B | 10/1993 |
| EP | 0 345 242 A2 | 12/1989 |

(Continued)

OTHER PUBLICATIONS

Fukuda (Glycobiology. Sep. 1991; 1 (4):347-56).*
Pimenidou et al. (Oncol. Rep. Feb. 2004; 11 (2):327-31).*
Park et al. (Tissue Antigens. Jan. 2004; 63 (1): 46-53).*
Brown et al. (J. Biol. Chem. Nov. 1, 1996; 271 (44): 27686-95).*
Fabbi et al. (J. Immunol. Dec. 1, 1999; 163 (11): 5964-70).*
Amendment After Final Office Action submitted on Feb. 7, 2011, for U.S. Appl. No. 12/338,934, filed Dec. 18, 2008, 10 pages.
Amendment After Allowance submitted on Apr. 21, 2011, for U.S. Appl. No. 12/338,934, filed Dec. 18, 2008, 9 pages.
Notice of Allowance mailed on Mar. 8, 2011, for U.S. Appl. No. 12/338,934, filed Dec. 18, 2008, 7 pages.
Singer, M. et al. (1998). "I. Molecules of the Genetic Apparatus," Figure 1.34 in *Genes and Genomes*, Jankowsky, N.K. Ed., University Science Books: Mill Valley, CA, vol. 1, p. 63, with Certified Translation, 7 pages total.

(Continued)

*Primary Examiner* — Stephen Rawlings
(74) *Attorney, Agent, or Firm* — Morrison & Foerster LLP

(57) ABSTRACT

The present invention provides novel antibodies specifically bind to an epitope on CD43 and CEA expressed on nonhematopoietic cancer cells, but do not specifically bind to a CD43 expressed by a leukocyte or by a Jurkat cell, and is capable of inducing apoptosis of the nonhematopoietic cancer cell after binding to the epitope on cell surface of the nonhematopoietic cancer cell in the absence of cytotoxin conjugation and immune effector function, wherein the epitope comprises a carbohydrate structure and the binding of the antibody to the epitope is inhibited by a carbohydrate comprising a $Le^a$ structure, a $Le^a$-lactose structure, a LNDFH II structure, or a LNT structure. In addition, the present invention also provides use of the antibodies described herein for diagnostic and therapeutic purposes.

30 Claims, 16 Drawing Sheets

(56) References Cited

U.S. PATENT DOCUMENTS

| | | | |
|---|---|---|---|
| 5,807,715 A | 9/1998 | Morrison et al. |
| 5,814,482 A | 9/1998 | Dubensky, Jr. et al. |
| 5,821,337 A | 10/1998 | Carter et al. |
| 5,866,692 A | 2/1999 | Shitara et al. |
| 5,997,867 A | 12/1999 | Waldmann et al. |
| 6,048,703 A | 4/2000 | Siman et al. |
| 6,120,767 A | 9/2000 | Robinson et al. |
| 6,180,370 B1 | 1/2001 | Queen et al. |
| 6,265,150 B1 | 7/2001 | Terstappen et al. |
| 6,291,643 B1 | 9/2001 | Zou et al. |
| 6,329,508 B1 | 12/2001 | Friden |
| 6,331,415 B1 | 12/2001 | Cabilly et al. |
| 6,376,471 B1 | 4/2002 | Lawrence, III et al. |
| 6,413,942 B1 | 7/2002 | Felgner et al. |
| 6,436,908 B1 | 8/2002 | Koch et al. |
| 6,548,640 B1 | 4/2003 | Winter |
| 6,652,852 B1 | 11/2003 | Robinson et al. |
| 6,808,901 B1 | 10/2004 | Neuberger et al. |
| 7,674,605 B2 | 3/2010 | Lin et al. |
| 7,982,017 B2 | 7/2011 | Lin et al. |
| 8,568,718 B2 | 10/2013 | Lin et al. |
| 2003/0027763 A1 | 2/2003 | Bennett et al. |
| 2003/0133939 A1 | 7/2003 | Ledbetter et al. |
| 2004/0058400 A1 | 3/2004 | Holliger et al. |
| 2008/0171043 A1 | 7/2008 | Lin et al. |
| 2009/0191221 A1 | 7/2009 | Lin et al. |
| 2011/0280888 A1 | 11/2011 | Lin et al. |
| 2014/0105899 A1 | 4/2014 | Lin et al. |

FOREIGN PATENT DOCUMENTS

| | | |
|---|---|---|
| EP | 0 345 242 A3 | 12/1989 |
| EP | 0 396 387 B1 | 11/1990 |
| EP | 0 528 767 B1 | 2/1993 |
| EP | 0 524 968 B1 | 6/1995 |
| EP | 1 782 838 A1 | 5/2007 |
| GB | 2200651 A | 6/1991 |
| JP | 2006-502091 A | 1/2006 |
| RU | 2 294 939 C2 | 3/2007 |
| WO | WO-87/04462 A1 | 7/1987 |
| WO | WO-89/12624 A2 | 12/1989 |
| WO | WO-89/12624 A3 | 12/1989 |
| WO | WO-90/07936 A1 | 7/1990 |
| WO | WO-90/11092 A1 | 10/1990 |
| WO | WO-91/00360 A1 | 1/1991 |
| WO | WO-91/00904 A1 | 1/1991 |
| WO | WO-91/02805 A1 | 3/1991 |
| WO | WO-91/14438 A1 | 10/1991 |
| WO | WO-91/14445 A1 | 10/1991 |
| WO | WO-92/08495 A1 | 5/1992 |
| WO | WO-92/20373 A1 | 11/1992 |
| WO | WO-93/03769 A1 | 3/1993 |
| WO | WO-93/06213 A1 | 4/1993 |
| WO | WO-93/10218 A1 | 5/1993 |
| WO | WO-93/11230 A1 | 6/1993 |
| WO | WO-93/19191 A1 | 9/1993 |
| WO | WO-93/25234 A1 | 12/1993 |
| WO | WO-93/25698 A1 | 12/1993 |
| WO | WO-94/03622 A1 | 2/1994 |
| WO | WO-94/04690 A1 | 3/1994 |
| WO | WO-94/12649 A2 | 6/1994 |
| WO | WO-94/12649 A3 | 6/1994 |
| WO | WO-94/23697 A1 | 10/1994 |
| WO | WO-94/28938 A1 | 12/1994 |
| WO | WO-95/00655 A1 | 1/1995 |
| WO | WO-95/07994 A2 | 3/1995 |
| WO | WO-95/07994 A3 | 3/1995 |
| WO | WO-95/11984 A2 | 5/1995 |
| WO | WO-95/11984 A3 | 5/1995 |
| WO | WO-95/13796 A1 | 5/1995 |
| WO | WO-95/30763 A2 | 11/1995 |
| WO | WO-95/30763 A3 | 11/1995 |
| WO | WO-96/17072 A2 | 6/1996 |
| WO | WO-96/17072 A3 | 6/1996 |
| WO | WO-97/42338 A1 | 11/1997 |
| WO | WO-99/58572 A1 | 11/1999 |
| WO | WO-03/074569 A2 | 9/2003 |
| WO | WO-03/074569 A3 | 9/2003 |
| WO | WO-03/074679 A2 | 9/2003 |
| WO | WO-03/074679 A3 | 9/2003 |
| WO | WO-03/093315 A2 | 11/2003 |
| WO | WO-03/093315 A3 | 11/2003 |
| WO | WO-2006/001348 A1 | 1/2006 |
| WO | WO-2006/065533 A2 | 6/2006 |
| WO | WO-2006/065533 A3 | 6/2006 |
| WO | WO-2007/048022 A2 | 4/2007 |
| WO | WO-2007/048022 A3 | 4/2007 |
| WO | WO-2007/146172 A2 | 12/2007 |
| WO | WO-2007/146172 A3 | 12/2007 |
| WO | WO-2007/146172 A8 | 12/2007 |
| WO | WO-2009/079649 A1 | 6/2009 |

OTHER PUBLICATIONS

Al-Lazikani, B. et al. (Nov. 7, 1997). "Standard Conformations for the Canonical Structures of Immunoglobulins," *Journal of Molecular Biology* 273(4):927-948.

Amendment in Response to Non-Final Office Action submitted on Jun. 23, 2009, for U.S. Appl. No. 11/811,303, filed Jun. 7, 2007, 33 pages.

Amendment in Response to Non-Final Office Action submitted on Sep. 29, 2010, for U.S. Appl. No. 12/338,934, filed Dec. 18, 2008, 13 pages.

Baeckström, D. et al. (Nov. 15, 1991). "Purification and Characterization of a Membrane-Bound and a Secreted Mucin-Type Glycoprotein Carrying the Carcinoma-Associated Sialyl-le$^a$ Epitope on Distinct Core Proteins," *J. Biol. Chem*. 266(32):21537-21547.

Baeckström, D. et al. (Jun. 9, 1995). "Expression of the Leukocyte-associated Sialoglycoprotein CD43 by a Colon Carcinoma Cell Line," *Journal of Biological Chemistry* 270(23):13688-13692.

Baeckström, D. et al. (Apr. 25, 1997). "Post-translation Fate of Mucin-like Leukocyte Sialoglycoprotein (CD43) Aberrantly Expressed in a Colon Carcinoma Cell Line," *Journal of Biological Chemistry* 272(17):11503-11509.

Bažil, V. et al. (Feb. 15, 1996). "A Monoclonal Antibody Recognizing CD43 (leukosialin) Initiates Apoptosis of Human Hematopoietic Progenitor Cells But Not Stem Cells," *Blood* 87(4):1272-1281.

Belhocine, T. et al. (Feb. 2004). "The Imaging of Apoptosis with the Radiolabeled Annexin V: Optimal Timing for Clinical Feasibility," *Technology in Cancer Research and Treatment* 3(1):23-32.

Boerner, P. et al. (Jul. 1, 1991). "Production of Antigen-Specific Human Monoclonal Antibodies from In Vitro-primed Human Splenocytes," *Journal of Immunology* 147(1):86-95.

Boyd, P.N. et al. (1995). "The Effect of the Removal of Sialic Acid, Galactose and Total Carbohydrate on the Functional Activity of Campath-1 H," *Molecular Immunology* 32(17/18):1311-1318.

Brodeur, B.R. et al. (1987). "Mouse-Human Myeloma Partners for the Production of Heterohybridomas," Chapter 4, In *Monoclonal Antibody Production Techniques and Applications*, Schook, L. ed., Marcel Dekker Inc.: New York, NY, 51-63.

Brown, T.J. et al. (1996). "Characterization of a CD43/leukosialin-mediated Pathway for Inducing Apoptosis in Human T-lymphoblastoid Cells," *Journal of Biological Chemistry* 271(44):27686-27695.

Burton, D.R. (1985). "Review. Immunoglobulin G: Functional Sites," *Mol. Immunol*. 22(3):161-206. (4.00 Spec).

Cabilly, S. et al. (1984). "Generation of Antibody Activity from Immunoglobulin Polypeptide Chains Produced in *Escherichia coli*," *Proceedings of the National Academy of Sciences of the United States of America* 81(11):3273-3277.

Carlow, D.A., et al. (Jan. 1, 2001). "Absence of CD43 Fails to Alter T Cell Development and Responsiveness," *Journal of Immunology* 166(1):256-261.

Čermák, L. et al. (Mar. 8, 2002, e-pub. Dec. 31, 2001). "Molecular Mechanisms Involved in CD43-mediated Apoptosis of TF-1 cells. Roles of Transcription Daxx Expression, and Adhesion Molecules," *Journal of Biological Chemistry* 277(10):7955-7961.

Chevinsky, A. H. (May-Jun. 1991). "CEA in Tumors of Other Than Colorectal Origin," *Seminars in Surgical Oncology* 7(3):162-166.

(56) References Cited

OTHER PUBLICATIONS

Chiou, H.C. et al. (1994). "In Vivo Gene Therapy Via Receptor Mediated DNA Delivery," Chapter II Methods and Mechanisms, In *Gene Therapeutics: Methods and Application of Direct Gene Transfer*, Wolff, J. A. ed., Birkhäuser: Boston, MA, pp. 143-156.

Chu, G. et al. (1987). "Electroporation for the Efficient Transfection of Mammalian Cells with DNA," *Nucleic Acids Research* 15(3):1311-1326.

Clackson, T. et al. (Aug. 1991). "Making Antibody Fragments Using Phage Display Libraries," *Nature* 352(6336):624-628.

Clynes, R. et al. (Jan. 1998). "Fc Receptors Are Required in Passive and Active Immunity to Melanoma," *Proceedings of the National Academy of Sciences of the United States of America* 95(2):652-656.

Co, M.S. et al. (Feb. 15, 1992). "Chimeric and Humanized Antibodies with Specificity for the CD33 Antigen," *J. Immunol.* 148(4):1149-1154. (cited as Man Sung in spec). 4.00 Spec.

Cole, S.P.C. et al. (1985). "The EBV-Hybridoma Technique and its Application to Human Lung Cancer," Monoclonal Antibodies and Cancer Therapy, Reisfeld, R.A. et al. ed., Alan R. Liss Inc., New York, NY, 77-96.

Connelly, S. et al. (Feb. 1995). "In Vivo Gene Delivery and Expression of Physiological Levels of Functional Human Factor VIII in Mice," Human Gene Therapy 6(2):185-193.

Curiel, D.T. et al. (1992). "High-Efficiency Gene Transfer Mediated by Adenovirus Coupled to DNA-Polylysine Complexes," *Human Gene Therapy* 3(2):147-154.

Dragone, L.L. et al. (Jan. 1995). "Disregulation of Leukosialin (CD43, Ly48, Sialophorin) Expression in the B-Cell Lineage of Transgenic Mice Increases Splenic B-Cell Number and Survival," *Proc. Natl. Acad. Sci. USA* 92:626-630.

Ellison, J. W. et al. (1981). "The Nucleotide Sequence of a Human Immunoglobulin $C_{\gamma 1}$ Gene," *Nucleic Acids Research* 10(13):4071-4079.

Fabbi, M. et al. (1994). "A Novel 120-kDa Antigen Shared by Immature Human Thmyocytes and Long-Term-Activated T Cells," *Eur. J. Immunol.* 24:1-7.

Fabbi, M. et al. (1999). "8B4/20, A Private CD43 Epitope on Developing Human Thymocytes, Is Involved in Thymocye Maturation," *J. Immunol.* 163:5964-5970.

Fernandez-Rodriguez, J. et al. (2002). "The Leukocyte Antigen CD43 is Expressed in Different Cell Lines of Nonhematopoietic Origin," *Tumor Biology* 23(4):193-201.

Final Office Action mailed on Dec. 7, 2010, for U.S. Appl. No. 12/338,934, filed Dec. 18, 2008, 6 pages.

Findeis, M.A. et al. (May 1993). "Targeted Delivery of DNA for Gene Therapy Via Receptors," *Trends in Biotechnology* 11(5):202-205.

Fuhlbrigge, R.C. et al. (Feb. 15, 2006). "CD43 is a Ligand for E-selectin on $CLA_+$ Human T Cells," *Blood* 107(4):1421-1426.

Gazzano-Santoro, H. et al. (Mar. 28, 1997). "A Aon-Radioactive Complement-Dependent Cytotoxicity Assay for Anti-CD20 Monoclonal Antibody," *Journal of Immunological Methods* 202(2):163-171.

Gennaro, A.R. ed. (2000). Remington: The Science and Practice of Pharmacy, 20th ed., Lippincott Williams & Wilkins: pp. xiv-xv (Table of Contents Only.).

George, J. et al. (1998). "Differential Effects of Anit-$\beta_2$-Glycoprotein I Antibodies on Endothelial Cells and on the Manifestations of Experimental Antiphospholipid Syndrome," *Circulation* 97:900-906.

Glaser, S.M. et al. (Dec. 16, 2005). "Novel Antibody Hinge Regions for Efficient Production of $C_{H2}$ Domain-Deleted Antibodies," *The Journal of Biological Chemistry* 280(50):41494-41503.

Goding, J.W. (1986). Monoclonal Antibodies: Principles and Practice, Academic Press Limited: San Diego, CA, 3 pages, (Table of Contents Only.).

Gold, P. et al. (1965). "Specific Carcinoembryonic Antigens of the Human Digestive System," *Journal of Experimental Medicine* 122(3):467-481.

Goldenberg, D. M. (1991) "Imaging and Therapy of Gastrointestinal Cancers with Radiolabeled Antibodies," *American Journal of Gastroenterology* 86(10):1392-1403.

Greenspan, N.S. et al. (Oct. 1999). "Defining Epitopes: It's Not as Easy as it Seems," *Nature Biotechnology* 7:936-937.

Griffiths, A.D. et al. (1993). "Human Anti-Self Antibodies with High Specificity from Phage Display Libraries," *The EMBO Journal* 12(2):725-734.

Hammarström, S. (Apr. 1999). "The Carcinoembryonic Antigen (CEA) Family: Structures, Suggested Functions and Expression in Normal and Malignant tissues," *Seminars in Cancer Biology* 9(2):67-81.

Harlow, E. et al. (1988). Antibodies, A laboratory Manual, Cold Spring Harbor Publications: Cold Spring Harbor, NY, pp. iii-ix, (Table of Contents Only.).

Hieter, P. A. et al. (Nov. 1980). "Cloned Human and Mouse Kappa Immunoglobulin Constant and J Region Genes Conserve Homology in Functional Segments," *Cell* 22:197-207.

Holt, L.J. et al. (Nov. 2003). "Domain Antibodies: Proteins for Therapy," *Trends Biotechnology* 21(11):484-490.

Hoogenboom, H.R. et al. (Sep. 1991). "By-Passing Immunisation: Human Antibodies from Synthetic Repertoires of Germline $V_H$ Gene Segments Rearranged in vitro," *Journal of Molecular Biology* 227(2):381-388.

Hsu, T.A. et al. (Apr. 4, 1997). "Differential N-Glycan Patterns of Secreted and Intracellular IgG Produced in Trichoplusia ni Cells," *Journal of Biological Chemistry* 272(14):9062-9070.

Iliades, P. et al. (Jun. 16, 1997). "Triabodies: Single Chain Fv Fragments without a Linker Form Trivalent Trimers," *FEBS Letters* 409(3):437-441.

Imakiire, T. et al. (Feb. 10, 2004). "Generation, Immunologic Characterization and Antitumor Effects of Human Monoclonal Antibodies for Carcinoembryonic Antigen," *International Journal of Cancer* 108(4):564-570.

Jefferis, R et al. (1997). "Glycosylation of Antibody Molecules: Structural and Functional Significance," *Chemical Immunology* 65:111-128.

Johnson, K. S. et al. (Aug. 1993). "Human Antibody Engineering," *Current Opinion in Structural Biology* 3(4):564-571.

Jolly, D. (Mar. 1994). "Viral Vector Systems for Gene Therapy," *Cancer Gene Therapy* 1(1):51-64.

Kabat, E.A. et al. (Sep. 1991). Sequences of Proteins of Immunological Interest, 5th ed., vol. 2, National Institutes of Health: Bethesda, MD, pp. iii-xi, (Table of Contents Only.).

Kadaja, L. et al. (Apr. 1, 2004). "Over Expression of Leukocyte Marker CD43 Causes Activation of the Tumor Suppressor Proteins p53 and ARF," *Oncogene* 23(14):2523-2530.

Kaplitt, M.G. et al. (Oct. 1994). "Long-Term Gene Expression and Phenotypic Correction Using Adeno-Associated Virus Vectors in the Mammalian Brain," *Nature Genetics* 8:148-154.

Kievit, E. (Dec. 1, 2000). "Yeast Cytosine Deaminase Improves Radiosensitization and Bystander Effect by 5-Fluorocytosine of Human Colorectal Cancer Xenografts," *Cancer Research* 60(23):6649-6655.

Kimura, O. et al. (Jul. 1994). "Retroviral Delivery of DNA into the Livers of Transgenic Mice Bearing Premalignant and Malignant Hepatocellular Carcinomas," Human Gene Therapy 5(7):845-852.

Kohler, G. et al. (Aug. 7, 1975). "Continuous Cultures of Fused Cells Secreting Antibody of Predefined Specificity," *Nature* 256(5517):495-497.

Kortt, A.A. et al. (Apr. 1997). "Single-Chain Fv Fragments of Anti-Neuraminidase Antibody NC10 Containing Five- and Ten-Residue Linkers Form Dimers and with Zero-Residue Linker a Trimer," *Protein Engineering* 10(4):423-433.

Kozbor, D. et al. (Dec. 1984). "A Human Hybrid Myeloma for Production of Human Monoclonal Antibodies," *Journal of Immunology* 133(6):3001-3005.

Kuroki, M. et al. (Nov.-Dec. 2000). "Specific Targeting Strategies of Cancer Gene Therapy Using a Single-Chain Variable Fragment (scFv) with a High Affinity for CEA," *Anticancer Research* 20(6A):4067-4072.

(56) References Cited

OTHER PUBLICATIONS

Kuroki, M. et al. (Nov.-Dec. 2002). "Significance of Tumor-associated Antigens in the Diagnosis and Therapy of Cancer: An Overview," *Anticancer Research* 22(6C):4255-4264.

Laos, S. et al. (2006). "Inhibition of NF-κb Activation and Chemokine Expression by the Leukocyte Glycoprotein, CD43, in Colon Cancer Cells," *International Journal of Oncology* 28(3):695-704.

Loo, D. et al. (Mar. 2007). "The Glycoptope-Specific RAV12 Monoclonal Antibody Induces Oncosis in vitro and Has Antitumor Activity Against Gastrointestinal Adenocarcinoma Tumor Xenografts in vivo," *Molecular Cancer Therapeutics* 6(3):856-865.

Lopez, S. et al. (Mar. 1998). "CD43 (Sialophorin, Leukosialin) Shedding is an Initial Event During Neutrophil Migration, Which Could Be Closely Related to the Spreading of Adherent Cells," *Cell Adhesion and Communication* 5(2):151-160.

Mahato, R.I. et al. (Jul. 1997). "Cationic Lipid-Based Gene Delivery Systems: Pharmaceutical Perspectives," *Pharmaceutical Research* 14 (7) :853-859.

Manjunath, N. et al. (Oct. 12, 1995). "Negative Regulation of T-cell Adhesion and Activation by CD43," *Nature* 377(6549):535-538.

Marks, J. D. et al. (Dec. 5, 1991). "By-Passing Immunization: Human Antibodies From V-Gene Libraries Displayed on Phage," *Journal of Molecular Biology* 222(3):581-597.

Marks, J. D. et al. (Jul. 1992). "By-Passing Immunization: Building High Affinity Human Antibodies by Chain Shuffling," *Biotechnology* 10(7):779-783.

Martin, S.J. et al. (Aug. 11, 1995). "Protease Activation During Apoptosis: Death by a Thousand Cuts?" *Cell* 82(3):349-352.

Matsumoto, M. et al. (Dec. 15, 2005). "CD43 Functions as a Ligand for E-Selectin on Activated T Cells," *Journal of Immunology* 175(12):8042-8050.

McCafferty, J. et al. (Dec. 6, 1990). "Phage Antibodies: Filamentous Phage Displaying Antibody Variable Domains," *Nature* 348(6301):552-554.

McEvoy, L.M. et al. (Apr. 21, 1997). "Anti-CD43 Inhibition of T Cell Homing," *Journal of Experimental Medicine* 185(8):1493-1498.

McEvoy, L.M. et al. (Nov. 1, 1997). "Anti-CD43 Inhibits Monocyte-Endothelial Adhesion in Inflammation and Atherogenesis," *Blood* 90(9):3587-3594.

Mentzer, S.J. et al. (May 1, 1987). "Sialophorin, a surface Sialoglycoprotein Defective in the Wiskott-Aldrich Ayndrome, is Involved in Human T Lymphocyte Proliferation," *Journal of Experimental Medicine* 165(5):1383-1392.

Milstein, C. et al. (Oct. 6, 1983). "Hybrid Hybridomas and Their Use in Immunohistochemistry," *Nature* 305(5934):537-540.

Mullis, K.B. et al. ed. (1994). *PCR: The Polymerase Chain Reaction*, Birkhäuser Press: Boston, MA, pp. xv-xvii, (Table of Contents Only.).

Munson, P.J. et al. (Sep. 1, 1980). "LIGAND: A Versatile Computerized Approach for Characterization of Ligand-Binding Systems," *Analytical Biochemistry* 107(1):220-239.

Muyldermans, S. et al. (Jun. 2001). "Single Domain Camel Antibodies: Current Status," *Journal of Biotechnology* 74(4):277-302.

Nieto, M., et al. (1999). "Signaling through CD43 induces natural killer cell activation, chemokine release, and PYK-2 activation," *Blood* 94(8):2767-2777.

Nilsson, O. et al. (Mar. 1985). "Sialosyllactotetraosylceramide, A Novel Ganglioside Antigen Detected in Human Carcinomas by a Monoclonal Antibody," *FEBS* 182(2):398-402.

Nisonoff, A. et al. (Aug. 1960). "Separation of Univalent Fragments From the Bivalent Rabbit Antibody Molecule by Reduction of Disulfide Bonds," *Archives of Biochemistry and Biophysics* 89:230-244.

Nong, Y.H. et al. (Jul. 1, 1989) "A Monoclonal Antibody to Sialophorin (CD43) Induces Homotypic Adhesion and Activation of Human Monocytes," *Journal of Experimental Medicine* 170(1):259-267.

Non-Final Office Action mailed on Dec. 23, 2008, for U.S. Appl. No. 11/811,303, filed Jun. 7, 2007, 41 pages.

Non-Final Office Action mailed on Jun. 29, 2010, for U.S. Appl. No. 12/338,934, filed Dec. 18, 2008, 12 pages.

Notice of Allowance mailed on Nov. 2, 2009, for U.S. Appl. No. 11/811,303, filed Jun. 7, 2007, 7 pages.

Oi, V.T. et al. (Feb. 1983). "Immunoglobulin Gene Expression in Transformed Lymphoid Cells," *Proceedings of the National Academy of Sciences of the United States of America* 80(3):825-829.

Olafsen, T. et al. (Jan. 2004). "Covalent Disulfide-Linked Anti-CEA Diabody Allows Site-Specific Conjugation and Radiolabeling for Tumor Targeting Applications," *Protein Engineering, Design & Selection* 17(1):21-27.

Pallant, A. et al. (Feb. 1989). "Characterization of cDNAs Encoding Human Leukosialin and Localization of the Leukosialin Gene to Chromosome 16," *Proceedings of the National Academy of Sciences of the United States of America* 86(4):1328-1332.

Park, J.K. et al. (Apr. 25, 1991). "Enhancement of T-cell Activation by the CD43 Molecule Whose Expression is Defective in Wiskott-Aldrich Syndrome," *Nature* 350(6320): 706-709.

Park, W.S. et al. (2004). "Production and the Characterization of Monoclonal Antibody Against CD43, K06," *Tissue Antigens* 63:46-53.

Philip, R. et al. (Apr. 1994). "Efficient and Sustained Gene Expression in Primary T Lymphocytes and Primary and Cultured Tumor Cells Mediated by Adeno-Associated Virus Plasmid DNA Complexed to Cationic Liposomes.," *Molecular and Cellular Biology* 14(4):2411-2418.

Pimenidou, A. et al. (Feb. 2004). "Novel CD43 Specific Phage Antibodies React with Early Stage Colorectal Tumours," *Oncology Reports* 11(2):327-331.

Porter, R.R. (Sep. 1959). "The Hydrolysis of Rabbit γ-globulin and Antibodies with Crystalline Papain," *The Biochemical Journal* 73:119-126.

Remold-O'Donnell, E. et al. (Jun. 1, 1984). "Characterization of a Human Lymphocyte Surface Sialoglycoprotein that is Defective in Wiskott-Aldrich Syndrome," *Journal of Experimental Medicine* 159(6): 1705-1723.

Remold-O'Donnell , E. et al. (Jul. 1987). "Expression on Blood Cells of Sialophorin, the Surface Glycoprotein that is Defective in Wiskott-Aldrich Syndrome," *Blood* 70(1): 104-109.

Rice, D. et al. (Dec. 1982). "Regulated Expression of an Immunoglobulin κ-Gene Introduced into a Mouse Lymphoid Cell line," *Proceedings of the National Academy of Sciences of the United States of America* 79(24):7862-7865.

Rousseaux, J. et al. (1986). "Optimal Conditions for the Preparation of Proteolytic Fragments from Monoclonal IgG of Different Rat IgG Subclasses," *Methods in Enzymology* 121:663-669.

Santamaria, M. et al. (Aug. 1, 1996). "Specific Monoclonal Antibodies Against Leukocyte-Restricted Cell Surface Molecule CD43 React with Nonhematopoietic Tumor Cells," *Cancer Research* 56(15):3526-3529.

Schneider, U. et al. (May 15, 1977). "Characterization of EBV-Genome Negative "Null" and "T" Cell Lines Derived from Children with Acute Lymphoblastic Leukemia and Leukemic Transformed Non-Hodgkin Lymphoma," *International Journal of Cancer* 19(5):621-626.

Scovassi, A.I. et al. (Sep. 1999). "Poly(ADP-Ribosylation) and Apoptosis," *Molecular and Cellular Biochemistry* 199(1-2):125-137.

Sheets, M.D. et al. (May 26, 1998). "Efficient Construction of a Large Nonimmune Phage Antibody Library: The Production of High-Affinity Human Single-Chain Antibodies to Protein Antigens," *Proceedings of the National Academy of Sciences of the United States of America* 95(11): 6157-6162.

Sheets, M.D. et al. (1999). "Efficient Construction of a Large Nonimmune Phage Antibody Library: The Production of High-Affinity Human Single-Chain Antibodies to Protein Antigens," *Proceedings of the National Academy of Sciences of the United States of America* Erratum 96:795.

Shelley, C.S. et al. (Apr. 1989). "Molecular Characterization of Sialophorin (CD43), the Lymphocyte Surface Sialoglycoprotein Defective in Wiskott-Aldrich Syndrome," *Proceedings of the National Academy of Sciences of the United States of America* 86(8):2819-2823.

(56) References Cited

OTHER PUBLICATIONS

Shively, J. E. et al. (1985). "CEA-Related Antigens: Molecular Biology and Clinical Significance," *Critical Reviews in Oncology/Hematology* 2(4):355-399.
Sikut, R. et al. (Sep. 18, 1997). "Colon Adenoma and Cancer Cells Aberrantly Express the Leukocyte-Associated Sialoglycoprotein CD43," *Biochemical and Biophysical Research Communications* 238(2):612-616.
Sikut, R. et al. (Jul. 2, 1999). "Detection of CD43 (leukosialin) in Colon Adenoma and Adenocarcinoma by Novel Monoclonal Antibodies Against its Intracellular Domain," *International Journal of Cancer* 82(1):52-58.
Smyth, D.G., (1967). "Use of Papain, Pepsin, and Subtilisin in Sequence Determination," *Methods in Enzymology* 11:421-426. (cited incorrectly as Edelman et al. in the spec).
Stockton, B.M. et al. (Mar. 1998). "Negative Regulation of T Cell Homing by CD43," *Immunity* 8(3):373-381.
Suresh, M.R. et al. (1986). "Bispecific Monoclonal Antibodies from Hybrid Hybridomas," *Methods in Enzymology* 121:210-228.
Thompson, J.A. et al. (May 1987). "Molecular Cloning of a Gene Belonging to the Carcinoembryonic Antigen Gene Family and Discussion of a Domain Model," *Proc. Natl. Acad. Sci. USA* 84(9):2965-2969.
Thornberry, N.A. et al. (Aug. 28, 1998). "Caspases: Enemies Within," *Science* 281(5381):1312-1316.
Toneguzzo, F. et al. (Feb. 1986). "Electric Field-Mediated DNA Transfer: Transient and Stable Gene Expression in Human and Mouse Lymphoid Cells.," *Molecular and Cellular Biology* 6(2):703-706.
Treasure, J. et al. (Nov. 1992). "CD43 Expression in B Cell Lymphoma," *Journal of Clinical Pathology* 45(11):1018-1022.
Umaña, P. et al. (Feb. 1999). "Engineered Glycoforms of an Antineuroblastoma IgG1 with Optimized Antibody-Dependent Cellular Cytotoxic Activity," *Nature Biotechnology* 17(2):176-180.
Vaughan, T.J. et al. (Mar. 1996). "Human Antibodies with Sub-Nanomolar Affinities Isolated from a Large Non-Immunized Phage Display Library," *Nature Biotechnology* 14(3):309-314.
Waterhouse, P. et al. (May 11, 1993). "Combinatorial Infection and in vivo Recombination: a Strategy for Making Large Phage Antibody Repertoires," *Nucleic Acids Research* 21(9):2265-2266.
Wilkinson, R. W. et al. (Aug. 28, 2001). "Antibody Targeting Studies in a Transgenic Murine Model of Spontaneous Colorectal Tumors," *Proceedings of the National Academy of Sciences of the United States of America* 98(18)10256-10260.
Winter, G. et al. (1994). "Making Antibodies by Phage Display Technology," *Annual Review of Immunology* 12:433-455.
Wittwer, A.J. et al. (May 1, 1990). "Glycosylation at Asn-184 Inhibits the Conversion of Single-Chain to Two-Chain Tissue-Type Plasminogen Activator by Plasmin," *Biochemistry* 29(17):4175-4180.
Woffendin, C. et al. (Nov. 22, 1994). "Nonviral and Viral delivery of a Human Immunodeficiency Virus Protective Gene into Primary Human T Cells," *Proceedings of the National Academy of Science of the United States of America* 91(24):1581-1585.
Wright, A. et al. (Jan. 1997). "Effect of Glycosylation on Antibody Function: Implications for Genetic Engineering," *Trends in Biotechnology* 15(1):26-32.
Wu, C.H. et al. (Oct. 15, 1989). "Targeting Genes: Delivery and Persistent Expression of a Foreign Gene Driven by Mammalian Regulatory Elements in Vivo," *Journal of Biological Chemistry* 264(29):16985-16987.
Wu, G.Y. et al. (Oct. 15, 1988). "Receptor-Mediated Gene Delivery and Expression in Vivo," *Journal of Biological Chemistry* 263(29):14621-14624.
Wu, G.Y. et al. (Aug. 5, 1991). "Receptor-Mediated Gene Delivery in Vivo Partial Correction of Genetic Analbuminemia in Nagase Rats.," *Journal of Biological Chemistry* 266(22):14338-14342.
Wu, G.Y. et al. (Apr. 15, 1994). "Incorporation of Adenovirus into a Ligand-Based DNA Carrier System Results in Retention of Original Receptor Specificity and Enhances Targeted Gene Expression," *Journal of Biological Chemistry* 269(15):11542-11546.
Wyllie, A.H. et al. (1980). "Cell Death: the Significance of Apoptosis," *International Review of Cytology* 68:251-306.
Wyss, D.F. et al. (Aug. 1996). "The Structural Role of Sugars in Glycoproteins," *Current Opinion in Biotechnology* 7(4):409-416.
Ychou, M. (Feb. 9, 1998). "Phase I/II Radio-Immunotherapy Study with Iodine-131-Labeled Anti-CEA Monoclonal Antibody F F(ab')$_2$ in Patients with Non-Resectable Liver Metastases From Colorectal Cancer," *International Journal of Cancer* 75(4):615-619.
Zenke, M. et al. (May 1990). "Receptor-Mediated Endocytosis of Transferrin-Polycation Conjugates: An Efficient Way to Introduce DNA into Hematopoietic Cells," *Proceedings of the National Academy of Science of the United States of America* 87(10):3655-3659.
Zola, H. et al. (1987). "Using Monoclonal Antibodies: Soluble Antigens," Chapter 6, in *Monoclonal Antibodies: A Manual of Techniques*, CRC Press Inc., Boca Raton, FL, pp. 147-181.
Bodey et al. (2000). "Failure of Cancer Vaccines: The Significant Limitations of this Approach to Immunotherapy," *Anticancer Research* 20:2665-2676.
Chatterjee et al. (1994). "Idiotypic Antibody Immunotherapy of Cancer," *Cancer Immunology and Immunotherapy* 38:75-82.
Degruijl et al. (Oct. 1999). "Cancer Vaccine Strategies Get Bigger and Better," *Nature Medicine* 5(10):1124-1125.
Donnelly (Nov. 2003). "Cancer Vaccine Targets Leukemia," *Nature Medicine* 9(11):1354-1356.
Ezzell (Jan. 1995). "Cancer "Vaccines": An Idea Whose Time Has Come?" *Journal of NIH Research* 7:46-49.
Forni et al. (May 15, 2000). "Immunoprevention of Cancer: Is the Time Ripe?" *Cancer Research* 60:2571-2575.
Lee et al. (1999). "Increased Vaccine Specific T Cell Frequency After Peptide-Based Vaccination Correlated with Increased Susceptibility to In Vitro Stimulation But Does Not Lead to Tumor Regression," *Journal of Immunology* 163:6292-6300.
Non-Final Office Action mailed on Mar. 14, 2012, for U.S. Appl. No. 13/156,233, filed Jun. 8, 2011, 9 pages.
Amano, J. et al. (2001). "Intestinal Epithelial Cells Express and Secrete the CD43 Glycoform That Contains Core 2 O-Glycans," *Microbes and Infection* 3:723-728.
Zhang, K. et al. (Dec. 4, 1996). "Comparison of Sialyl-Lewis a-Carrying CD43 and MUC1 Mucins Secreted From a Colon Carcinoma Cell Line for E-Selection Binding and Inhibition of Leukocyte Adhesion," *Tumor Biology* (18)175-187.
Amit, A.G. et al. (Aug. 15, 1986). "Three-Dimensional Structure of an Antigen-Antibody Complex at 2.8 A Resolution," *Science* 233:747-753.
Anonymous. (Jun. 27, 2006). "Monoclonal Antibody to CD43 (Human) (K06)," Product Data Sheet, Alexis Biochemicals, 2 pages.
Bernard, A. et al. (Dec. 1986). "A Unique Epitope on the CD2 Molecule Defined by the Monoclonal Antibody 9-1: Epitope-Specific Modulation of the E-rosette Receptor and Effects on T-cell Functions," *Human Immunol* 17(4):388-405.
Casadevall, A. et al. (Jul. 31, 2012). "Immunoglobin Isotype Influences Affinity and Specificity," *Proceedings of the National Academy of Sciences* 109(31):12272-12273.
Dall'Acqua, W.F. et al. (Jul. 15, 2006). Modulation of the Effector Functions of a Human IgG1 through Engineering of its Hinge Region, *J Immunol* 177(2):1129-1138.
Dangl, J.L. et al. (Jul. 1988). "Segmental Flexibility and Complement Fixation of Genetically Engineered Chimeric Human, Rabbit and Mouse Antibodies," *The EMBO Journal* 7(7):1989-1994.
Dorai, H. et al. (1992). "Role of Inter-Heavy and Light Chain Disulfide Bonds in the Effector Functions of Human Immunoglobulin IgG1," *Molecular Immunology* 29(12):1487-1491.
McCloskey, N. et al. (Jun. 1996). "Human Constant Regions Influence the Antibody Binding Characteristics of Mouse-Human Chimeric IgG Subclasses," *Immunology* 88(2):169-173.
Non-Final Office Action mailed on Dec. 12, 2012, for U.S. Appl. No. 13/156,233, filed Jun. 8, 2011, 10 pages.
Paul, W.E. ed. (1984). *Fundamental Immunology* Raven Press, New York, pp. 231-235, with English Translation pp. 149-152.

(56) References Cited

OTHER PUBLICATIONS

Pettersen, R.D. et al. (Jun. 15, 1999). "CD47 Signals T Cell Death," *J. Immunol* 162(12):7031-7040.

Pritsch, O. et al. (Nov. 1996). "Can Immunoglobulin $C_H1$ Constant Region Domain Modulate Antigen Binding Affinity of Antibodies?" *Journal of Clinical Investigation* 98(10): 2235-2243.

Roux, K.H. et al. (Oct. 15, 1998). "Comparisons of the Ability of Human IgG3 Hinge Mutants, IgM, IgE, and IgA2, to Form Small Immune Complexes: A Role for Flexibility and Geometry," *J Immunol*:161(8):4083-4090.

Vajdos, F.F et al. (2002). "Comprehensive Functional Maps of the Antigen-Binding Site of an Anti-ErbB2 Antibody Obtained with Shotgun Scanning Mutagenesis," *J Mol Biol* 320, 415-428.

Vitetta, E.S. et al. (2006). "Considering Therapeutic Antibodies," *Science* 313:308-309.

Zips, D. et al. (2005). "New Anticancer Agents: In Vitro and In Vivo Evaluation," In vivo 19(1)1-7.

\* cited by examiner

COLO 205

DLD-1

NCI-N87

Colorectal Cancer Cell Lines

Normal Colorectal Cell Line

A

B

A.

B.

SEQUENCE LISTING

```
<160> NUMBER OF SEQ ID NOS: 33

<210> SEQ ID NO 1
<211> LENGTH: 137
<212> TYPE: PRT
<213> ORGANISM: Murine

<400> SEQUENCE: 1

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Arg Met Ser Cys Thr Ala Ser Gly Tyr Thr Phe
        35                  40                  45

Thr Ser Tyr Val Met His Trp Ile Lys Gln Lys Pro Gly Gln Gly Leu
    50                  55                  60

Asp Trp Ile Gly Tyr Ile Asn Pro Tyr Asn Gly Thr Gln Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Arg Thr Phe Pro Tyr Tyr Phe Asp Tyr Trp Gly
        115                 120                 125

Gln Gly Thr Thr Leu Thr Val Ser Ser
    130                 135

<210> SEQ ID NO 2
<211> LENGTH: 131
<212> TYPE: PRT
<213> ORGANISM: Murine

<400> SEQUENCE: 2

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Leu His Ser Asn Gly Asn Thr Tyr Leu Glu Trp Tyr Leu Gln Lys Pro
```

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Ala Pro Leu Thr Phe Gly Ala Gly Thr Lys Leu
        115                 120                 125

Glu Leu Lys
        130

<210> SEQ ID NO 3
<211> LENGTH: 140
<212> TYPE: PRT
<213> ORGANISM: Murine

<400> SEQUENCE: 3

Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Ser Phe
        35                  40                  45

Ile Ser Tyr Trp Met His Trp Val Lys Gln Arg Pro Gly Gln Gly Leu
    50                  55                  60

Glu Trp Ile Gly Ala Ile Ser Pro Gly Asp Ser Asp Thr Thr Tyr Asn
65                  70                  75                  80

Gln Arg Phe Thr Gly Lys Ala Lys Leu Thr Ala Val Thr Ser Ala Ser
                85                  90                  95

Thr Ala Tyr Met Glu Leu Ser Ser Leu Thr Asn Glu Asp Ser Ala Val
            100                 105                 110

Tyr Tyr Cys Ile Arg Arg Asp Gly Asn Tyr Gln Val Ala Trp Phe Ala
        115                 120                 125

Tyr Trp Gly Gln Gly Thr Leu Val Thr Val Ser Ala
    130                 135                 140

<210> SEQ ID NO 4
<211> LENGTH: 131
<212> TYPE: PRT
<213> ORGANISM: Murine

<400> SEQUENCE: 4

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys

```
            100                 105                 110
Phe Gln Gly Ser His Val Pro Phe Thr Phe Gly Ser Gly Thr Lys Leu
            115                 120                 125

Glu Ile Lys
    130

<210> SEQ ID NO 5
<211> LENGTH: 140
<212> TYPE: PRT
<213> ORGANISM: Murine

<400> SEQUENCE: 5

Met Glu Cys Asn Trp Ile Leu Pro Phe Ile Leu Ser Val Ile Ser Gly
  1               5                  10                  15

Val Tyr Ser Glu Val Gln Leu Gln Gln Ser Gly Thr Val Leu Ala Arg
                 20                  25                  30

Pro Gly Ala Ser Val Lys Met Ser Cys Lys Ala Ser Gly Tyr Ser Phe
             35                  40                  45

Thr Ser Tyr Trp Met His Trp Val Lys Gln Arg Thr Gly Gln Gly Leu
         50                  55                  60

Glu Trp Ile Gly Ala Ile Ser Pro Gly Asp Gly Asp Thr Thr Tyr Asn
 65                  70                  75                  80

Gln Lys Phe Thr Gly Lys Ala Lys Leu Thr Ala Val Thr Ser Ala Ser
                 85                  90                  95

Thr Ala Tyr Met Glu Leu Ser Ser Leu Thr His Glu Asp Ser Ala Val
            100                 105                 110

Tyr Tyr Cys Thr Arg Arg Asp Gly Ser Tyr Gln Val Ala Trp Phe Ala
            115                 120                 125

Tyr Trp Gly Arg Gly Thr Leu Val Thr Val Ser Ala
    130                 135                 140

<210> SEQ ID NO 6
<211> LENGTH: 131
<212> TYPE: PRT
<213> ORGANISM: Murine

<400> SEQUENCE: 6

Met Lys Leu Pro Val Arg Leu Leu Val Leu Met Phe Trp Ile Pro Val
  1               5                  10                  15

Ser Ser Ser Asp Val Leu Met Thr Gln Thr Pro Leu Ser Leu Pro Val
                 20                  25                  30

Ser Leu Gly Asp Gln Ala Ser Ile Ser Cys Arg Ser Ser Gln Ser Ile
             35                  40                  45

Val His Ser Asn Gly Asn Thr Tyr Leu Glu Trp Phe Leu Gln Lys Pro
         50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
            115                 120                 125

Glu Ile Lys
    130
```

```
<210> SEQ ID NO 7
<211> LENGTH: 137
<212> TYPE: PRT
<213> ORGANISM: Artificial Sequence
<220> FEATURE:
<223> OTHER INFORMATION: synthetic construct

<400> SEQUENCE: 7

Met Gly Trp Ser Trp Ile Phe Leu Phe Leu Leu Ser Gly Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Val Met His Trp Val Arg Gln Ala Pro Gly Gln Gly Leu
    50                  55                  60

Glu Trp Ile Gly Tyr Ile Asn Pro Tyr Asn Gly Gly Thr Gln Tyr Asn
65                  70                  75                  80

Glu Lys Phe Lys Gly Lys Ala Thr Ile Thr Ala Asp Glu Ser Thr Asn
                85                  90                  95

Thr Ala Tyr Met Glu Leu Ser Ser Leu Thr Ser Glu Asp Ser Ala Val
            100                 105                 110

Tyr Tyr Cys Ala Arg Arg Thr Phe Pro Tyr Tyr Phe Asp Tyr Trp Gly
        115                 120                 125

Gln Gly Thr Thr Leu Thr Val Ser Ser
    130                 135

<210> SEQ ID NO 8
<211> LENGTH: 132
<212> TYPE: PRT
<213> ORGANISM: Artificial Sequence
<220> FEATURE:
<223> OTHER INFORMATION: synthetic construct

<400> SEQUENCE: 8

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ser Ser Gln Ser
        35                  40                  45

Ile Leu His Ser Asn Gly Asn Thr Tyr Leu Glu Trp Tyr Gln Gln Lys
    50                  55                  60

Pro Gly Lys Ala Pro Lys Leu Leu Ile Tyr Lys Val Ser Asn Arg Phe
65                  70                  75                  80

Ser Gly Val Pro Ser Arg Phe Ser Gly Ser Gly Ser Gly Thr Asp Phe
                85                  90                  95

Thr Leu Thr Ile Ser Ser Leu Gln Pro Asp Asp Phe Ala Thr Tyr Tyr
            100                 105                 110

Cys Phe Gln Gly Ser His Ala Pro Leu Thr Phe Gly Gln Gly Thr Lys
        115                 120                 125

Val Glu Leu Lys
    130

<210> SEQ ID NO 9
<211> LENGTH: 411
<212> TYPE: DNA
<213> ORGANISM: Murine
```

```
<400> SEQUENCE: 9
atggaatgga gttggatatt tctctttctc ctgtcaggaa ctgcaggtgt ccactctgag      60
gtccagctgc agcagtctgg acctgagctg gtaaagcctg ggcttcagt gaggatgtcc     120 tgcacggctt ctggatacac attcactagc tatgttatgc actggataaa gcagaagcct    180
gggcagggcc ttgactggat tggatatatt aatccttaca tggtggtac tcagtacaat     240 gagaagttca aggcaaggc cacactgact tcagacaaat cctccagcac agcctacatg     300
gagctcagca gcctgacctc tgaggactct gcggtctatt actgtgcaag acggaccttc    360
ccgtactact ttgactactg gggccaaggc accactctca cagtctcctc a             411

<210> SEQ ID NO 10
<211> LENGTH: 393
<212> TYPE: DNA
<213> ORGANISM: Murine

<400> SEQUENCE: 10
atgaagttgc ctgttaggct gttggtgctg atgttctgga ttcctgcttc cagcagtgat     60
gttttgatga cccaaactcc actctccctg cctgtcagtc ttggagatca agcctccatc    120
tcttgcagat ctagtcagag catttttacat agtaatggaa acacctattt gaatggtac    180 ctgcagaaac caggccagtc tccaaagctc ctgatctaca agtttccaa ccgattttct     240 ggggtcccag acaggttcag tggcagtgga tcagggacag atttcacact caagatcagc    300
agagtggagg ctgaggatct gggagtttac tactgctttc aaggttcaca tgctcctctc    360
acgttcggtg ctgggaccaa gctggagctg aaa                                 393

<210> SEQ ID NO 11
<211> LENGTH: 420
<212> TYPE: DNA
<213> ORGANISM: Murine

<400> SEQUENCE: 11 atgaatgta actggatact tccttttatt ctgtcggtaa tttcaggggt ctactcagag      60
gttcagctcc agcagtctgg gactgtgctg gcaaggcctg ggcttccgt gaagatgtcc     120 tgcaaggctt ctggctacag ctttatcagc tactggatgc actgggtaaa acagaggcct    180
ggacagggtc tagaatggat tggtgctatt tctcctggag atagtgatac tacctacaac    240
cagaggttca cgggcaaggc caaactgact gcagtcacat ccgccagcac tgcctacatg    300
gagctcagca gcctgacaaa tgaggactct gcggtctatt attgtataag aagggatggt    360
aactaccaag ttgcctggtt tgcttactgg ggccaaggga ctctggtcac tgtctctgca    420

<210> SEQ ID NO 12
<211> LENGTH: 393
<212> TYPE: DNA
<213> ORGANISM: Murine

<400> SEQUENCE: 12
atgaagttgc ctgttaggct gttggtgctg atgttctgga ttcctgcttc cagcagtgat     60
gttttgatga cccaaactcc actctccctg cctgtcagtc ttggagatca agcctccatc    120
tcttgcagat ctagtcagag cattgtacat agtaatggaa acacctattt gaatggtac    180 ctgcagaaac caggccagtc tccaaagctc ctgatctaca agtttccaa ccgattttct     240 ggggtcccag acaggttcag tggcagtgga tcagggacag atttcacact caagatcagc    300
agagtggagg ctgaggatct gggagtttat tactgctttc aaggttcaca tgttccattc    360
```

```
acgttcggct cggggacaaa gttggaaata aaa                            393
```

<210> SEQ ID NO 13
<211> LENGTH: 420
<212> TYPE: DNA
<213> ORGANISM: Murine

<400> SEQUENCE: 13

```
atggaatgta actggatact tccttttatt ctgtcggtaa tttcaggggt ctactcagag    60
gttcagctcc agcagtctgg gactgtgctg gcaaggcctg gggcttccgt gaagatgtcc   120
tgcaaggctt ctggctacag ttttaccagc tactggatgc actgggtaaa acagaggact   180
gggcagggtc tagaatggat tggtgctatt tctcctggag atggtgatac tacctacaac   240
cagaagttca cggcaaggc caaactgact gcagtcacat ccgccagcac tgcctacatg   300
gagctcagca gcctgacaca tgaggactct gcggtctatt actgtacaag aagagatggt   360
agctaccaag ttgcctggtt tgcttactgg ggccgaggga ctctggtcac tgtctctgca   420
```

<210> SEQ ID NO 14
<211> LENGTH: 393
<212> TYPE: DNA
<213> ORGANISM: Murine

<400> SEQUENCE: 14

```
atgaaattgc ctgttaggct gttggtgctg atgttctgga ttcctgtttc cagcagtgat    60
gttttgatga cccaaactcc actctccctg cctgtcagtc ttggagatca agcctccatc   120
tcttgcagat ctagtcagag cattgtccat agtaatggaa acacctattt agaatggttc   180
ctgcagaaac caggccagtc tccaaagctc ctgatctaca agtttccaa ccgatttttct   240
ggggtcccag acaggttcag tggcagtgga tcagggacag atttcacact caagatcagc   300
agagtggagg ctgaggatct gggagtttat tactgctttc aaggttcaca tgttccattc   360
acgttcggct cggggacaaa gttggaaata aaa                               393
```

<210> SEQ ID NO 15
<211> LENGTH: 411
<212> TYPE: DNA
<213> ORGANISM: Artificial Sequence
<220> FEATURE:
<223> OTHER INFORMATION: synthetic construct

<400> SEQUENCE: 15

```
atgggatgga gctggatctt tctcttcctc ctgtcaggta ccgcgggcgt gcactctcag    60
gtccagcttg tccagtctgg ggctgaagtc aagaaacctg gctcgagcgt gaaggtctcc   120
tgcaaggctt ctggctacac ctttactagc tatgttatgc actgggtaag gcaggcccct   180
ggacagggtc tggaatggat tggatatatt aatccttaca atggtggtac tcagtacaat   240
gagaagttca aggcaaggc cacaattact gcagacgaat ccaccaatac agcctacatg   300
gaactgagca gcctgacatc tgaggacagc gcagtctatt actgtgcaag acggaccttc   360
ccgtactact ttgactactg gggccaagga accacgctca cagtctcctc a           411
```

<210> SEQ ID NO 16
<211> LENGTH: 396
<212> TYPE: DNA
<213> ORGANISM: Artificial Sequence
<220> FEATURE:
<223> OTHER INFORMATION: synthetic construct

<400> SEQUENCE: 16

```
atggagaccg ataccctcct gctatgggtc ctcctgctat gggtcccagg atcaaccgga       60
gatattcaga tgacccagtc tccatcttcc ctctctgcta gcgtcgggga tagggtcacc      120
ataacctgca gatctagtca gagcatttta catagtaatg aaacaccta tttagaatgg      180
taccagcaga agccaggcaa agctcccaag cttctaatct ataaagtttc caaccgattt      240
tctggagtcc cttcacgctt cagtggcagt ggatctggga ccgatttcac cctcacaatc      300
agctctctgc agccagatga tttcgccact tattactgct ttcaaggttc acatgctcct      360
ctcacgttcg gtcaggggac caaggtggag ctgaaa                               396
```

<210> SEQ ID NO 17
<211> LENGTH: 12
<212> TYPE: PRT
<213> ORGANISM: Artificial Sequence
<220> FEATURE:
<223> OTHER INFORMATION: synthetic construct

<400> SEQUENCE: 17

Trp Pro Ile Asp Leu Met Ser Glu Thr Pro Ile Leu
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: synthetic construct

<400> SEQUENCE: 18

Trp Pro Ile Ala Asn His Glu Asn Ala Leu Ser Ala
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: synthetic construct

<400> SEQUENCE: 19

Trp Pro Ile Ser Gly Lys His Ser Phe Trp Ser Leu
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: synthetic construct

<400> SEQUENCE: 20

Trp Pro Ile Leu Asp His Ala Val Ser Arg Pro Ser
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: synthetic construct

<400> SEQUENCE: 21

Trp Pro Ile Asp Ile Pro Tyr Ala Trp Asp Phe Ser

```
<210> SEQ ID NO 22
<211> LENGTH: 12
<212> TYPE: PRT
<213> ORGANISM: Artificial Sequence
<220> FEATURE:
<223> OTHER INFORMATION: synthetic construct

<400> SEQUENCE: 22

Trp Pro Ile Ser Pro Gln Pro Gly Ala Arg Pro Val
1               5                   10

<210> SEQ ID NO 23
<211> LENGTH: 12
<212> TYPE: PRT
<213> ORGANISM: Artificial Sequence
<220> FEATURE:
<223> OTHER INFORMATION: synthetic construct

<400> SEQUENCE: 23

Trp Pro Ile Ala Pro Asn Arg Tyr Leu Leu Ser Ser
1               5                   10

<210> SEQ ID NO 24
<211> LENGTH: 12
<212> TYPE: PRT
<213> ORGANISM: Artificial Sequence
<220> FEATURE:
<223> OTHER INFORMATION: synthetic construct

<400> SEQUENCE: 24

Trp Pro Ile Pro Pro Glu Val Glu Pro Phe Lys His
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic construct

<400> SEQUENCE: 25

Trp Pro Ile Leu Gln Asn Ala Ala Gly Thr Gly Leu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic construct

<400> SEQUENCE: 26

Trp Pro Ile Pro Thr Leu Met Glu Leu Pro Ser Ala
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic construct

<400> SEQUENCE: 27

Trp Pro Ile Thr Asn Ser Asp Ser Arg Ile Thr Trp
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: synthetic construct

<400> SEQUENCE: 28

Trp Pro Ile His Ser Ala His Val Arg Tyr Thr Thr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: synthetic construct

<400> SEQUENCE: 29

Ala Glu Thr Asp Tyr Asp Pro Asp His Phe Thr Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: synthetic construct

<400> SEQUENCE: 30

Asp Ala Arg Tyr Ser His Asp Pro Ala Trp Pro Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: synthetic construct

<400> SEQUENCE: 31

Ala Gly Gln Lys Trp Asp Pro Glu Trp Pro His Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: synthetic construct

<400> SEQUENCE: 32

Tyr Asp His His Trp Thr Asn Pro Pro Thr Gln Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetic construct

<400> SEQUENCE: 33

Glu Pro Asn Met Asp Pro Asn Trp Ala Ser Pro Ser
1               5                   10
```

ANTIBODIES RECOGNIZING A CARBOHYDRATE CONTAINING EPITOPE ON CD-43 AND CEA EXPRESSED ON CANCER CELLS AND METHODS USING SAME

CROSS-REFERENCE TO RELATED APPLICATIONS

This application is a divisional application of U.S. patent application Ser. No. 11/811,303, filed Jun. 7, 2007, which claims the priority benefit of U.S. provisional application Ser. No. 60/811,850, filed Jun. 7, 2006, all of which are incorporated herein by reference in their entirety.

FIELD OF THE INVENTION

The present invention relates to novel monoclonal antibodies that recognize a carbohydrate containing epitope on CD43 and carcinoembryonic antigen (CEA) expressed on nonhematopoietic tumor or cancer cells. These antibodies have the property of inducing cell death (e.g., apoptosis) in these non-hematopoietic tumor or cancer cells in the absence of cytotoxin conjugation and immune effector function. These monoclonal antibodies are useful as diagnostic and therapeutic agents.

BACKGROUND OF THE INVENTION

CD43 (also named as sialophorin or leukosialin), a heavily sialylated molecule expresses at high levels on most human leukocytes including all T cells and platelets with a molecular weight ranging from 115,000 to 135,000. CD43 expression is defective on the T cells of males with the Wiskott-Aldrich syndrome, an X chromosome-linked recessive immunodeficiency disorder (Remold-O'Donnell et al. (1987) Blood 70(1):104-9; Remold-O'Donnel et al. (1984) J. Exp. Med. 159:1705-23).

Functional studies demonstrated that anti-CD43 monoclonal antibody stimulates the proliferation of peripheral blood T lymphocytes (Mentzer et al. (1987) J. Exp. Med. 1:165 (5):1383-92; Park et al. (1991) Nature, 350:706-9) and the activation of monocytes (Nong et al. (1989) J. Exp. Med. 1:170(1):259-67). A monoclonal anti-CD43 antibody L11 blocks T cell binding to lymph node and Peyer's patch HEV. Antibody L11 inhibits T cell extravasation from the blood into organized secondary lymphoid tissues (McEvoy et al. (1997) J. Exp. Med. 185:1493-8). Monoclonal antibody recognizing CD43 molecule induces apoptosis of lineage marker-negative bone marrow hematopoietic progenitor cells (HPCs) that express CD34 at a high density (Bazil et al. (1996) Blood, 87(4):1272-81.) and of human T-lymphoblastoid cells (Brown et al. (1996) J. Biol. Chem. 271:27686-95). Recent studies further indicated that CD43 functions as a ligand for E-selectin on human T cells (Matsumoto et al. (2005) J. Immunol. 175:8042-50; Fuhlbrigge et al. (2006) Blood, 107:1421-6).

Interestingly, scientists have also discovered that certain nonhematopoietic tumor cells, especially colorectal adenocarcinomas, do express CD43 molecules on the cell surface. Santamaria et al. (1996) Cancer Research, 56:3526-9: Baeckstrom et al. (1995) J. Biol. Chem. 270:13688-92; Baeckstrom et al. (1997) J. Biol. Chem. 272:11503-9; Sikut et al. (1997) Biochem. Biophy. Res. Commun. 238:612-6. It has been shown that glycans on CD43 expressed in a colon carcinoma cell line (COLO 205) are different from those of leukocyte CD43 (Baeckstrom et al. (1997) J. Biol. Chem.272:11503-9).

Although it has been suggested that over-expression of CD43 causes activation of the tumor suppressor protein p53 (Kadaja et al. (2004) Oncogene 23:2523-30) and suppresses a subset of NF-kappaB target genes, partly via the inhibition of p65 transcriptional activity (Laos et al. (2006) Int. J. Oncol. 28:695-704), the direct evidence showing the causal role of CD43 in colon tumorigenesis is still lacking. The use of conventional anti-CD43 antibody as therapeutics for nonhematopoietic tumor cells is not practical due to its strong binding to both tumor and immune T cells. There remains a need to generate antibodies that specifically bind to a CD43 expressed on non-hematopoietic tumor or cancer cells, but do not bind to a CD43 expressed on leukocytes or other cells of hematopoietic origin. These antibodies may be useful as therapeutic agents for treating CD43 expressing nonhematopoietic cancer.

CEA is normally expressed in a variety of glandular epithelial tissues (such as the gastrointestinal, respiratory, and urogenital tracts) where it appears to be localized to the apical surface of the cells (Hammarstrom, S. (1999) Semin. Cancer Biol. 9, 67-81.). In tumors arising from these tissues, there is an increasing level of CEA expression extending from the apical membrane domain to the entire cell surface, together with secretion of the protein into the blood (Hammarstrom, S. (1999) Semin. Cancer Biol. 9, 67-81.). The excessive expression of CEA was observed in many types of cancers, including colorectal cancer, pancreatic cancer, lung cancer, gastric cancer, hepatocellular carcinoma, breast cancer, and thyroid cancer. Therefore, CEA has been used as a tumor marker and immunological assays to measure the elevated amount of CEA in the blood of cancer patients have long been utilized clinically in the prognosis and management of cancers (Gold P, et al. (1965) J Expl. Med. 122:467-81; Chevinsky, A. H. (1991) Semin. Surg. Oncol. 7, 162-166; Shively, J. E. et al., (1985) Crit. Rev. Oncol. Hematol. 2, 355-399).

More importantly, CEA has become a potentially useful tumor-associated antigen for targeted therapy (Kuroki M, et al. (2002) Anticancer Res 22:4255-64). Two major strategies using CEA as a target for cancer immunotherapy have been developed. One method is the specific targeting of suicide genes (nitric oxide synthase (iNOS) gene) (Kuroki M. et al., (2000) Anticancer Res. 20(6A):4067-71) or isotopes (Wilkinson R W. et al., (2001) PNAS USA 98, 10256-60, Goldenberg, D. M. (1991) Am. J. Gastroenterol., 86: 1392-1403, Olafsen T. et al., Protein Engineering, Design & Selection, 17, 21-27, 2004) to CEA-expressing tumor cells by anti-CEA antibodies. This method has also been extended to the use of antibody or antibody fragment conjugated with therapeutic agents, such as drugs, toxins, radionucleotides, immumodulators or cytokines. The other method is to utilize immunological cytolytic activities, specifically through antibody-dependent cellular cytotoxicity (ADCC) or complement-dependent cytotoxicity (CDC) to eliminate CEA-expressing tumor cells (Imakiire T et al., (2004) Int. J. Cancer: 108, 564-570). These methods often give rise to cytokine releases resulting in systemic side effects.

All references, publications, and patent applications disclosed herein are hereby incorporated by reference in their entirety.

BRIEF SUMMARY OF THE INVENTION

In one aspect, the present invention provides novel antibodies that specifically bind to an epitope on CD43 and CEA expressed by a nonhematopoietic cancer cell, but do not specifically bind to a CD43 expressed by a leukocyte (e.g., human peripheral T cells) or a Jurkat cell (a lymphoblastoid leukemia cell). The epitope that the antibodies bind to comprises a carbohydrate. These antibodies are capable of inducing cell death in these nonhematopoietic cancer cells in the absence of cytotoxin conjugation to the antibodies and immune effector function.

The invention provides an antibody, which antibody specifically binds to an epitope on CD43 and/or CEA expressed by a nonhematopoietic cancer cell, but does not specifically bind to a CD43 expressed by a leukocyte or by a Jurkat cell, and is capable of inducing apoptosis of the nonhematopoietic cancer cell after binding to the epitope expressed on cell surface of the nonhematopoietic cancer cell in the absence of cytotoxin conjugation and immune effector function, wherein the epitope comprises a carbohydrate, and the binding of the antibody to the epitope is inhibited by a carbohydrate comprising a Le$^a$ structure, a Le$^a$-lactose structure, a LNDFH II structure, or a LNT structure. In some embodiments, the epitope that the antibody binds to is fucose sensitive.

The nonhematopoietic cancer cell includes, but is not limited to, cells from colorectal cancer and gastric cancer.

In some embodiments, the antibody described herein is a monoclonal antibody. In some embodiments, the antibody described herein is a murine, a human, a humanized, or a chimeric antibody.

In some embodiments, the antibody described herein, upon binding to the epitope expressed on the cell surface of the nonhematopoietic cancer cell, reduces the number of cancer cells, and/or inhibits growth or proliferation of the cancer cell. For example, the reduction in cell number or inhibition of cell growth in the presence the antibody is by at least any of about 10%, about 20%, about 30%, about 40%, about 50%, about 65%, about 75%, or greater as compared to cell number or cell growth in the absence of the antibody.

In some embodiments, the antibody described herein recognizes a conformation epitope on an extracellular domain of the CD43 and CEA expressed by the nonhematopoietic cancer cell, wherein the conformation epitope includes a structure having physical and chemical characteristics equivalent to the structure formed by tripeptide, N'-Trp-Pro-Ile-C'. In some embodiments, the antibody described herein binds to a polypeptide comprising the amino acid sequence of N'-Trp-Pro-Ile-C' at the N-terminus of the polypeptide.

In some embodiments, the antibody described herein competes with an antibody comprising a heavy chain variable region comprising the amino acid sequence of SEQ ID NO:1, and a light chain variable region comprising the amino acid sequence of SEQ ID NO:2, for binding to the epitope present on the cell surface of the nonhematopoietic cancer cell.

In some embodiments, the antibody described herein competes with an antibody comprising a heavy chain variable region comprising the amino acid sequence of SEQ ID NO:3, and a light chain variable region comprising the amino acid sequence of SEQ ID NO:4, for binding to the epitope present on the cell surface of the nonhematopoietic cancer cell.

In some embodiments, the antibody described herein competes with an antibody comprising a heavy chain variable region comprising the amino acid sequence of SEQ ID NO:5, and a light chain variable region comprising the amino acid sequence of SEQ ID NO:6, for binding to the epitope expressed on the cell surface of the nonhematopoietic cancer cell.

In some embodiments, the antibody comprises a heavy chain variable region comprising three CDRs from the amino acid sequence of SEQ ID NO:1, and a light chain variable region comprising three CDRs from the amino acid sequence of SEQ ID NO:2. In some embodiments, the antibody comprises a heavy chain variable region comprising the amino acid sequence of SEQ ID NO:1, and a light chain variable region comprising the amino acid sequence of SEQ ID NO:2.

In some embodiments, the antibody comprises a heavy chain variable region comprising three CDRs from the amino acid sequence of SEQ ID NO:3, and a light chain variable region comprising three CDRs from the amino acid sequence of SEQ ID NO:4. In some embodiments, the antibody comprises a heavy chain variable region comprising the amino acid sequence of SEQ ID NO:3, and a light chain variable region comprising the amino acid sequence of SEQ ID NO:4.

In some embodiments, the antibody comprises a heavy chain variable region comprising three CDRs from the amino acid sequence of SEQ ID NO:5, and a light chain variable region comprising three CDRs from the amino acid sequence of SEQ ID NO:6. In some embodiments, the antibody comprises a heavy chain variable region comprising the amino acid sequence of SEQ ID NO:5, and a light chain variable region comprising the amino acid sequence of SEQ ID NO:6.

In some embodiments, the antibody is a humanized antibody comprising a heavy chain variable region comprising the amino acid sequence of SEQ ID NO:7, and a light chain variable region comprising the amino acid sequence of SEQ ID NO:8.

In another aspect, the present invention provides polypeptides comprising a heavy chain and/or light chain, or a fragment of the antibody described herein. The invention also provides polypeptides derived from any of the antibodies described herein, wherein the polypeptides specifically bind to the epitope on CD43 and CEA expressed by a nonhematopoietic cancer cell, but do not specifically bind to a CD43 expressed by a leukocyte or by a Jurkat cell, and are capable of inducing apoptosis of the nonhematopoietic cancer cell after binding to the CD43 expressed on cell surface of the nonhematopoietic cancer cell in the absence of cytotoxin conjugation and immune effector function.

In another aspect, the present invention provides polynucleotides encoding any of the antibodies or polypeptides described herein. The invention also provides vectors (such as expression vectors) comprising any of the polynucleotides described herein. The invention also provides host cells comprising any of the polynucleotides or vectors described herein.

In another aspect, the present invention provides a composition comprising any of the antibodies or polypeptides described herein. In certain embodiments, the antibodies or the polypeptides are linked to an agent. In some embodiments, the agent is a therapeutic agent (e.g., radioactive moieties, cytotoxins, and chemotherapeutic agents). In some embodiments, the agent is a label (e.g., enzymes, fluorescent molecules, and biotin).

The invention also provides a pharmaceutical composition comprising an effective amount of any of the antibodies or polypeptides described herein, or polynucleotides encoding the antibodies or polypeptides, and a pharmaceutically acceptable carrier. In some embodiments, the antibodies or the polypeptides are linked to a therapeutic agent. In some embodiments, the composition is formulated for administration by intraperitoneal, intravenous, subcutaneous, and intramuscular injections, and other forms of administration such as oral, mucosal, via inhalation, sublingually, etc.

In some embodiments, the composition may comprise more than one antibodies of the invention, or one antibody of the invention with one or more other anti-cancer antibodies or other anti-cancer agents.

In another aspect, the present invention provides methods for generating an antibody or a polypeptide described herein comprising culturing a host cell or progeny thereof under conditions that allow production of the antibody or polypeptide, wherein the host cell comprises an expression vector that encodes for the antibody or the polypeptide In some embodiments, the method further comprises purifying the antibody or the polypeptide.

In another aspect, the invention provides methods of generating any of the antibodies described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the present invention provides methods for inducing apoptosis in a nonhematopoietic cancer cell expressing the epitope on the cell surface, comprising contacting the cancer cell with an antibody or a polypeptide described herein. In some embodiments, the cancer cell is in an individual.

In another aspect, the present invention provides methods for treating nonhematopoietic cancer in an individual comprising administering to the individual an effective amount of a composition comprising an antibody or a polypeptide described herein, wherein the antibody or polypeptide bind to the cancer cells in the individual. In some embodiments, the cancer is colorectal, pancreatic, gastric, or lung cancer.

In another aspect, the present invention provides methods for treating nonhematopoietic cancer in an individual comprising administering to the individual an amount of an antibody or a polypeptide described herein, and an amount of another anti-cancer agent, wherein the antibody or polypeptide binds to the cancer cells in the individual, and whereby the antibody or the polypeptide and the anti-cancer agent in conjunction provide effective treatment of cancer in the individual.

In another aspect, the present invention provides kits for treating nonhematopoietic cancer in an individual comprising an antibody or a polypeptide described herein. These kits may further comprise instructions for administering the antibody or the polypeptide to the individual for treating the cancer.

In another aspect, the present invention provides methods for detecting or diagnosing of a nonhematopoietic cancer, identifying individual having a nonhematopoietic cancer for treatment, or monitoring progression of a nonhematopoietic cancer, comprising contact a sample with an antibody or a polypeptide described herein; and detecting presence or absence, or level of binding the antibody or the polypeptide to a cell in the sample. The presence of binding between the antibody and a cell in the sample indicates that the sample may contain a cancer cell, and/or the individual having cancer may be treated with an antibody described herein. The methods may further comprises a step of comparing the level of binding to a control.

In another aspect, the present invention provides kits for detecting or diagnosing of nonhematopoietic cancer, identifying individual having nonhematopoietic cancer for treatment, or monitoring progression of nonhematopoietic cancer, comprising an antibody or a polypeptide described herein, and reagents for detecting binding of the antibody or the polypeptide to a cell in a sample.

BRIEF DESCRIPTION OF THE DRAWINGS

In FIG. 11A, cell lysates of COLO 205 expressing flag-tagged human CEA were immunoprecipitated with anti-Flag® antibody M2, immunoprecipitated proteins were run on SDS-PAGE and then transferred to NC paper. NC paper was incubated with anti-Flag M2, m5F1, 51-41, 138-10, or CEA/Ab-3 as indicated. In FIG. 11B, cell lysates of COS-7 cells expressing flag-tagged human CEA (+) or non-CEA expressing COS-7 cells (-) were immunoprecipitated with anti-Flag® antibody M2, immunoprecipitated proteins were run on SDS-PAGE and then transferred to NC paper. NC paper was incubated with anti-Flag® M2, m5F1, or CEA/Ab-3 as indicated.

In FIG. 12A, soluble CD43 expressed by COLO 205 cells purified with protein A Sepharose® beads were run on SDS-PAGE and transferred to NC paper, and the NC paper was Western blotted with antibody m5F1, 51-14 or 138-10. In FIG. 12B, cell lysates of COS-7 cells transfected with hCD43, hCD43/myc-His, or untransfected cells were run on SDS-PAGE and transferred to NC paper, and the NC paper was Western blotted with anti-CD43 (MEM59) (left panel) or m5F1 (right panel).

DETAILED DESCRIPTION OF THE INVENTION

Definitions

Figure 1:
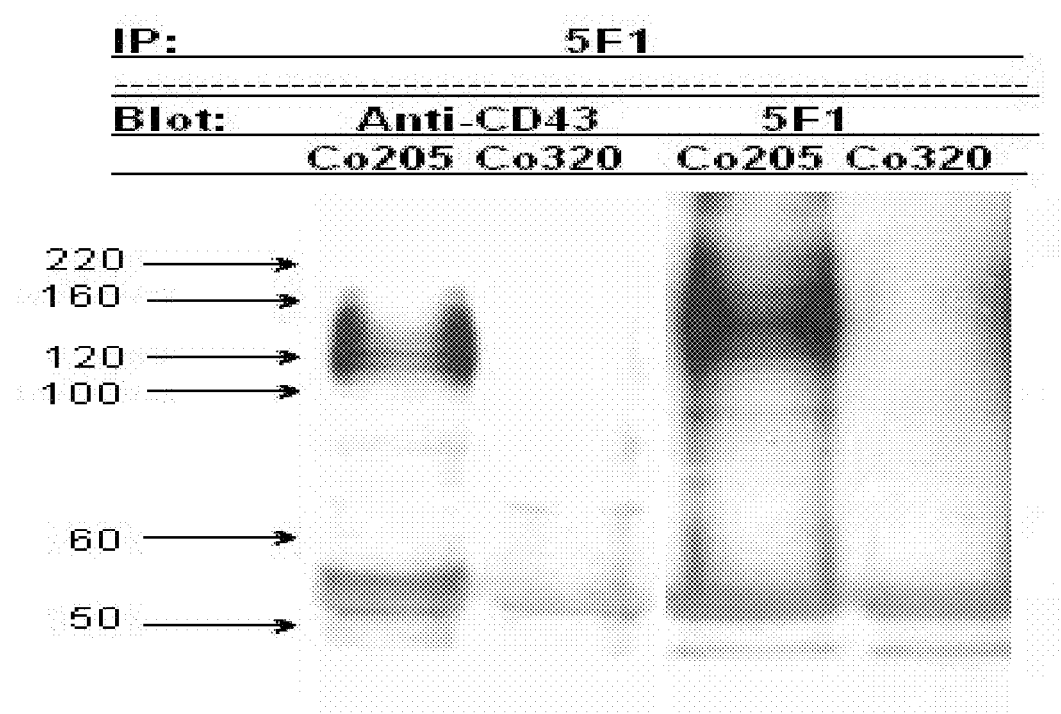
FIG. 1 shows the results of identification of the target protein of 5F1. Protein in the eluate of 5F1 immunoaffinity column from COLO 205 lysate (lanes 1 and 3) or COLO 320 lysate (lanes 2 and 4) was immunoblotted with a commercial anti-CD43 antibody AF2038 (lanes 1 and 2) or antibody 5F1 (lanes 3 and 4).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibody of the present invention is further intended to include bispecific, multispecific, single-chain, and chimeric and humanized molecules having affinity for a polypeptide conferred by at least one CDR region of the antibody. Antibodies of the present invention also include single domain antibodies which are either the variable domain of an antibody heavy chain or the variable domain of an antibody light chain. Holt et al., *Trends Biotechnol.* 21:484-490, 2003. Methods of making domain antibodies comprising either the variable domain of an antibody heavy chain or the variable domain of an antibody light chain, containing three of the six naturally occurring complementarity determining regions from an antibody, are also known in the art. See, e.g., Muyldermans, *Rev. Mol. Biotechnol.* 74:277-302, 2001.

As used herein, "monoclonal antibody" refers to an antibody of substantially homogeneous antibodies, i.e., the individual antibodies comprising the population are identical except for possible naturally-occurring mutations that may be present in minor amounts. Monoclonal antibodies are generally highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, a "chimeric antibody" refers to an antibody having a variable region or part of variable region from a first species and a constant region from a second species. An intact chimeric antibody comprises two copies of a chimeric light chain and two copies of a chimeric heavy chain. The production of chimeric antibodies is known in the art (Cabilly et al. (1984), *Proc. Natl. Acad. Sci. USA*, 81:3273-3277; Harlow and Lane (1988), *Antibodies: a Laboratory Manual*, Cold Spring Harbor Laboratory). Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human is less likely to elicit an immune response from a human subject when the antibodies are injected than would the constant region from a non-human source. However, the definition is not limited to this particular example.

An "isolated" antibody is one which has been identified and separated and/or recovered from a component of its natural environment.

As used herein, "substantially pure" refers to material which is at least 50% pure (i.e., free from contaminants), more preferably at least 90% pure, more preferably at least 95% pure, more preferably at least 98% pure, more preferably at least 99% pure.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination. A constant region of an antibody generally provides structural stability and other biological functions such as antibody chain association, secretion, transplacental mobility, and complement binding, but is not involved with binding to the antigen. The amino acid sequence and corresponding exon sequences in the genes of the constant region will be dependent upon the species from which it is derived; however, variations in the amino acid sequence leading to allotypes will be relatively limited for particular constant regions within a species. The variable region of each chain is joined to the constant region by a linking polypeptide sequence. The linkage sequence is coded by a "J" sequence in the light chain gene, and a combination of a "D" sequence and a "J" sequence in the heavy chain gene.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, PNAS (USA), 95:652-656.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "individual" or a "subject" is a mammal, more preferably a human. Mammals also include, but are not limited to, farm animals, sport animals, pets (such as cats, dogs, horses), primates, mice and rats.

As use herein, the term "specifically recognizes" or "specifically binds" refers to measurable and reproducible interactions such as attraction or binding between a target and an antibody, that is determinative of the presence of the target in the presence of a heterogeneous population of molecules including biological molecules. For example, an antibody that specifically or preferentially binds to an epitope is an antibody that binds this epitope with greater affinity, avidity, more readily, and/or with greater duration than it binds to other epitopes of the target or non-target epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, the terms "cancer," "tumor," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, and sarcoma. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, thyroid cancer, testicular cancer, esophageal cancer, and various types of head and neck cancer.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and variations of the invention described herein include "consisting" and/or "consisting essentially of" aspects and variations.

Antibodies and Polypeptides that Specifically Bind to a Carbohydrate Epitope on CD43 and CEA Expressed on Nonhematopoietic Cancer Cells The invention provides isolated antibodies, and polypeptides derived from the antibodies, that specifically bind to an epitope on CD43 and/or CEA expressed by nonhematopoietic cancer cells, but do not specifically bind to a CD43 expressed by a leukocyte (such as a peripheral T cell) or a Jurkat cell. The antibodies and polypeptides of the invention may further have one or more of the following characteristics: (a) binding of the antibody or the polypeptide to the epitope is reduced if the molecule comprising the epitope is treated with α-1→(2,3,4)-Fucosidase; (b) binding of the antibody or the polypeptide to the epitope is inhibited by a carbohydrate comprising a Le$^a$ structure, a Le$^a$-lactose structure, a LNDFH II structure, and/or a LNT structure; (c) induce death of the nonhematopoietic cancer cell (such as through apoptosis) after binding to the epitope expressed on the cell surface of the cancer cell in the absence of cytotoxin conjugation and immune effector function; (d) inhibit cell growth or proliferation of the nonhematopoietic cancer cell after binding to the epitope expressed on the cell surface of the cancer cell; and (e) treat or prevent nonhematopoietic cancer expressing the epitope on the cell surface, such as colorectal cancer and gastric cancer, in an individual.

As used herein, the term "inhibition" includes partial and complete inhibition. For example, binding of the antibody or the polypeptide to the epitope on CD43 and CEA is inhibited by at least about 20%, at least about 30%, at least about 40%, at least about 50%, at least about 60%, at least about 70%, at least about 80%, or at least about 90% by a carbohydrate comprising a Le$^a$ structure, a Le$^a$-lactose structure, a LNDFH II structure, or a LNT structure. Binding of the antibody to the epitope may be inhibited by direct competition or by other mechanisms.

Examples of non-hematopoietic cancer cells expressing the epitope include, but are not limited to, colorectal cancer cells (such as COLO 205 and DLD-1) and gastric cancer cells (such as NCI-N87).

The antibodies and polypeptides of the present invention may recognize an extracellular domain of a CD43 present on a nonhematopoietic cancer cell, but does not bind to an extracellular domain of a leukocyte CD43 (e.g., a peripheral T cell), or an extracellular domain of CD43 expressed on a Jurkat cell (a lymphoblastoid leukemia cell). In some embodiments, the novel antibodies or polypeptides of the invention do not specifically bind to a CD43 expressed by a cell of hematopoietic origin.

The antibodies of the invention can encompass monoclonal antibodies, polyclonal antibodies, antibody fragments (e.g., Fab, Fab', F(ab')$_2$, Fv, Fc, etc.), chimeric antibodies, single chain (ScFv), mutants thereof, fusion proteins comprising an antibody portion, and any other modified configuration of the immunoglobulin molecule that comprises an antigen recognition site of the required specificity. The antibodies may be murine, rat, camel, human, or any other origin (including humanized antibodies).

The binding affinity of the polypeptide (including antibody) to CD43 or CEA may be less than any of about 500 nM, about 400 nM, about 300 nM, about 200 nM, about 100 nM, about 50 nM, about 10 nM, about 1 nM, about 500 pM, about 100 pM, or about 50 pM. As is well known in the art, binding affinity can be expressed as $K_D$, or dissociation constant, and an increased binding affinity corresponds to a decreased $K_D$. One way of determining binding affinity of antibodies to CD43 or CEA is by measuring binding affinity of monofunctional Fab fragments of the antibody. To obtain monofunctional Fab fragments, an antibody (for example, IgG) can be cleaved with papain or expressed recombinantly. The affinity of an Fab fragment of an antibody can be determined by surface plasmon resonance (BIAcore3000™ surface plasmon resonance (SPR) system, BIAcore, INC, Piscaway N.J.) and ELISA. Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibodies and polypeptides of the invention reduce the number of cancer cells, and/or inhibit cell growth or proliferation of tumor or cancer cells that have the epitope. Preferably, the reduction in cell number or inhibition of cell growth or proliferation is by at least about 10%, about 20%, about 30%, about 40%, about 50%, about 65%, about 75%, or greater as compared to the cell not treated with the antibody or polypeptides. Cancer cells include, but are not limited to, colorectal cancer, pancreatic cancer, lung cancer, gastric cancer.

In some embodiments, the antibodies and polypeptides of the invention are capable of inducing cell death alone, for example through apoptosis, after binding the epitope expressed on cell surface of the nonhematopoietic cancer cell. The term "induce cell death" as used herein, means that the antibodies or polypeptides of the present invention, can directly interact with a molecule expressed on the cell surface, and the binding/interaction alone is sufficient to induce cell death in the cells without the help of other factors such as cytotoxin conjugation or other immune effector functions, i.e., complement-dependent cytotoxicity (CDC), antibody-dependent cellular cytotoxicity (ADCC), or phagocytosis.

As used herein, the term "apoptosis" refers to gene-directed process of intracellular cell destruction. Apoptosis is distinct from necrosis; it includes cytoskeletal disruption, cytoplasmic shrinkage and condensation, expression of phosphatidylserine on the outer surface of the cell membrane and blebbing, resulting in the formation of cell membrane bound vesicles or apoptotic bodies. The process is also referred to as "programmed cell death." During apoptosis, characteristic phenomena such as curved cell surfaces, condensation of nuclear chromatin, fragmentation of chromosomal DNA, and loss of mitochondrial function are observed. Various known technologies may be used to detect apoptosis, such as staining cells with Annexin V, propidium iodide, DNA fragmentation assay and YO-PRO®-1 (Invitrogen).

Methods of detecting cell death (such as apoptosis) include, but are not limited to, detecting morphology, DNA fragmentation, enzymatic activity, and polypeptide degradation, etc. See Siman et al., U.S. Pat. No. 6,048,703; Martin and Green (1995), *Cell*, 82: 349-52; Thornberry and Lazebnik (1998), *Science*, 281:1312-6; Zou et al., U.S. Pat. No. 6,291, 643; Scovassi and Poirier (1999), *Mol. Cell Biochem.*, 199: 125-37; Wyllie et al. (1980), *Int. Rev. Cytol.*, 68:251-306; Belhocine et al. (2004), *Technol. Cancer Res. Treat.*, 3(1):23-32, which are incorporated herein by reference.

In some embodiments, the antibodies and polypeptides of the invention recognize a conformation epitope expressed on a nonhematopoietic cancer cell, and this epitope includes a structure having physical and chemical characteristics equivalent to the structure formed by tripeptide, N'-Trp-Pro-Ile-C'. As used herein, "an epitope which includes a structure having physical and chemical characteristics equivalent to the structure formed by a peptide" means that both structures have a similar physical and chemical property related to antibody binding so that an antibody that specifically binds to one structure would bind to both structures. In some embodiments, the antibodies and polypeptides bind to a polypeptide comprising amino acid sequence, N'-Trp-Pro-Ile-C' at the N-terminus of the polypeptide.

In some embodiments, the antibodies and polypeptides of the invention competes with antibody 5F1, 138-10, or 51-41, for binding to the epitope expressed on the cell surface of the cancer cell. In some embodiments, the antibodies or polypeptides of the invention binding to an epitope on CD43 or CEA to which at least one of antibodies 5F1, 138-10, and 51-41 binds.

Competition assays can be used to determine whether two antibodies bind the same epitope by recognizing identical or sterically overlapping epitopes or one antibody competitively inhibits binding of another antibody to the antigen. These assays are known in the art and are described in detail in the Examples. Typically, antigen or antigen expressing cells is immobilized on a multi-well plate and the ability of unlabeled antibodies to block the binding of labeled antibodies is measured. Common labels for such competition assays are radioactive labels or enzyme labels.

In some embodiments, the antibody of the invention is antibody 5F1 or an antibody derived from 5F1. The heavy chain and light chain variable sequences of 5F1 are set forth in SEQ ID NO:1 and SEQ ID NO:2, respectively. The invention provides an antibody or a polypeptide comprising a fragment or a region of the antibody 5F1. In one embodiment, the fragment is a light chain of the antibody 5F1. In another embodiment, the fragment is a heavy chain of the antibody 5F1. In yet another embodiment, the fragment contains one or more variable regions from a light chain and/or a heavy chain of the antibody 5F1. In yet another embodiment, the fragment contains one, two, or three CDRs from a light chain and/or a heavy chain of the antibody 5F1. In some embodiments, the antibody is a humanized antibody of 5F1, such as h5F1 comprising the heavy chain variable region shown in SEQ ID NO:7 and the light chain variable region shown in SEQ ID NO:8. In some embodiments, the one or more CDRs derived from antibody 5F1 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of 5F1.

In some embodiments, the antibody of the invention is antibody 138-10 or an antibody derived from 138-10. The heavy chain and light chain variable sequences of 138-10 are set forth in SEQ ID NO:3 and SEQ ID NO:4, respectively. The invention provides an antibody or a polypeptide comprising a fragment or a region of the antibody 138-10. In one embodiment, the fragment is a light chain of the antibody 138-10. In another embodiment, the fragment is a heavy chain of the antibody 138-10. In yet another embodiment, the fragment contains one or more variable regions from a light chain and/or a heavy chain of the antibody 138-10. In yet another embodiment, the fragment contains one, two, or three CDRs from a light chain and/or a heavy chain of the antibody 138-10. In some embodiments, the antibody is a humanized antibody of 138-10. In some embodiments, the one or more CDRs derived from antibody 138-10 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of 138-10.

In some embodiments, the antibody of the invention is antibody 51-41 or an antibody derived from 51-41. The heavy chain and light chain variable sequences of 51-41 are set forth in SEQ ID NO:5 and SEQ ID NO:6, respectively. The invention provides an antibody or a polypeptide comprising a fragment or a region of the antibody 51-41. In one embodiment, the fragment is a light chain of the antibody 51-41. In another embodiment, the fragment is a heavy chain of the antibody 51-41. In yet another embodiment, the fragment contains one or more variable regions from a light chain and/or a heavy chain of the antibody 51-41. In yet another embodiment, the fragment contains one, two, or three CDRs from a light chain and/or a heavy chain of the antibody 51-41. In some embodiments, the antibody is a humanized antibody of 51-41. In some embodiments, the one or more CDRs derived from antibody 51-41 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of 51-41.

In some embodiments, the CDR is a Kabat CDR. In other embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined.

Methods of making antibodies and polypeptides derived from the antibodies are known in the art and are disclosed herein. The monoclonal antibodies of the present invention can be prepared using well-established methods. For example, the monoclonal antibodies can be prepared using hybridoma technology, such as those described by Kohler and Milstein (1975), Nature, 256:495. In a hybridoma method, a mouse, a hamster, or other appropriate host animal, is typically immunized with an immunizing agent (e.g., a cancer cell expressing CD43 or CEA, CD43 or CEA (including extracellular domain and fragments thereof expressed by the cancer cell) which may be purified using antibodies described herein, or a polypeptide comprising amino acid sequence N'-Trp-Pro-Ile-C' at the N-terminus of the polypeptide) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-1031). Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human hetero-myeloma cell lines also have been described for the production of human monoclonal antibodies (Kozbor, J. Immunol. (1984), 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies. The antibody may be screened for having specific binding to the epitope on CD-43 or CEA expressed by the nonhematopoietic cancer or tumor cells, but no specific binding to CD43 expressing leukocyte, Jurkat cells, and/or other CD43 expressing cells of hematopoietic origin. Cancer cells or extracellular domain (including fragments thereof) containing the epitope may be used for screening. For example, CEA-N-A2 expressed by COLO 205 cells described in Example 10 may used for screening.

Jurkat cell line is a lymphoblastoid leukemia cell, and was established from the peripheral blood of a 14 year old boy by Schneider et al. Schneider et al., Int. J. Cancer 19:621-626, 1977. Various Jurkat cell lines are commercially available, for example, from American Type Culture Collection (e.g., ATCC TIB-152, ATCC TIB-153, ATCC CRL-2678).

Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980), Anal. Biochem., 107:220.

The antibodies identified may further be tested for their capabilities to induce cell death (e.g., apoptosis), and/or inhibiting cell growth or proliferation using methods known in the art and described herein.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies can be generated by culturing the hybridoma cells, and the antibodies secreted by the hybridoma cells may further be isolated or purified. Antibodies may be isolated or purified from the culture medium or ascites fluid by conventional immunoglobulin purification procedures such as, for example, protein A-Sepharose®, hydroxylapatite chromatography, gel electrophoresis, dialysis, or affinity chromatography.

The antibodies of the invention can also be made by recombinant DNA methods, such as those described in U.S. Pat. Nos. 4,816,567 and 6,331,415, which are hereby incorporated by reference. for example, DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiment, the antibodies of the present invention are expressed from two expression vectors. The first expression vector encodes a heavy chain of the antibody (e.g., a humanized antibody), comprising a first part encoding a variable region of the heavy chain of the antibody, and a second part encoding a constant region of the heavy chain of the antibody. In some embodiments, the first part encodes a variable region having an amino acid sequence represented by SEQ ID NO:7. The second expression vector encodes a light chain of the antibody, comprising a first part encoding a variable region of the light chain of the antibody, and a second part encoding a constant region of the light chain of the antibody. In some embodiments, the first part encodes a variable region having an amino acid sequence represented by SEQ ID NO:8.

Alternatively, the antibodies (e.g., a humanized antibody) of the present invention are expressed from a single expression vector. The single expression vector encodes both the heavy chain and light chain of the antibodies of the present invention. In some embodiments, the expression vector comprises a polynucleotide sequence encoding a variable region of the heavy chain having an amino acid sequence represented by SEQ ID NO:7 and a variable region of the light chain having an amino acid sequence represented by SEQ ID NO:8.

Normally the expression vector has transcriptional and translational regulatory sequences which are derived from species compatible with a host cell. In addition, the vector ordinarily carries a specific gene(s) which is (are) capable of providing phenotypic selection in transformed cells.

A wide variety of recombinant host-vector expression systems for eukaryotic cells are known and can be used in the invention. For example, *Saccharomyces cerevisiae*, or common baker's yeast, is the most commonly used among eukaryotic microorganisms, although a number of other strains, such as *Pichia pastoris*, are available. Cell lines derived from multicellular organisms such as Sp2/0 or Chinese Hamster Ovary (CHO), which are available from the ATCC, may also be used as hosts. Typical vector plasmids suitable for eukaryotic cell transformations are, for example, pSV2neo and pSV2gpt (ATCC), pSVL and pSVK3 (Pharmacia), and pBPV-1/pML2d (International Biotechnology, Inc.).

The eukaryotic host cells useful in the present invention are, preferably, hybridoma, myeloma, plasmacytoma or lymphoma cells. However, other eukaryotic host cells may be suitably utilized provided the mammalian host cells are capable of recognizing transcriptional and translational DNA sequences for expression of the proteins; processing the leader peptide by cleavage of the leader sequence and secretion of the proteins; and providing post-translational modifications of the proteins, e.g., glycosylation.

Accordingly, the present invention provides eukaryotic host cells which are transformed by recombinant expression vectors comprising DNA constructs disclosed herein and which are capable of expressing the antibodies or polypeptides of the present invention. In some embodiments, the transformed host cells of the invention, therefore, comprise at least one DNA construct comprising the light and heavy chain DNA sequences described herein, and transcriptional and translational regulatory sequences which are positioned in relation to the light and heavy chain-encoding DNA sequences to direct expression of antibodies or polypeptides.

The host cells used in the invention may be transformed in a variety of ways by standard transfection procedures well known in the art. Among the standard transfection procedures which may be used are electroporation techniques, protoplast fusion and calcium-phosphate precipitation techniques. Such techniques are generally described by F. Toneguzzo et al. (1986), *Mol. Cell. Biol.*, 6:703-706; G. Chu et al., *Nucleic Acid Res.* (1987), 15:1311-1325; D. Rice et al., *Proc. Natl. Acad. Sci. USA* (1979), 79:7862-7865; and V. Oi et al., *Proc. Natl. Acad. Sci. USA* (1983), 80:825-829.

In the case of two expression vectors, the two expression vectors can be transferred into a host cell one by one separately or together (co-transfer or co-transfect).

The present invention also provides a method for producing the antibodies or polypeptides, which comprises culturing a host cell comprising an expression vector(s) encoding the antibodies or the polypeptides, and recovering the antibodies or polypeptides from the culture by ways well know to one skilled in the art.

Furthermore, the desired antibodies can be produced in a transgenic animal. A suitable transgenic animal can be obtained according to standard methods which include micro-injecting into eggs the appropriate expression vectors, transferring the eggs into pseudo-pregnant females and selecting a descendant expressing the desired antibody.

The present invention also provides chimeric antibodies that specifically recognize the epitope on CD43 and CEA expressed by a cancer cell. For example, the variable and constant regions of the chimeric antibody are from separate species. In some embodiments, the variable regions of both heavy chain and light chain are from the murine antibodies described herein. In some embodiments, the variable regions comprise amino acid sequences shown in SEQ ID NO:1 and SEQ ID NO:2. In some embodiments, the variable regions comprise amino acid sequences shown in SEQ ID NO:3 and SEQ ID NO:4. In some embodiments, the variable regions comprise amino acid sequences shown in SEQ ID NO:5 and SEQ ID NO:6. In some embodiments, the constant regions of both the heavy chain and light chain are from human antibodies.

The chimeric antibody of the present invention can be prepared by techniques well-established in the art. See for example, U.S. Pat. Nos. 6,808,901, 6,652,852, 6,329,508, 6,120,767 and 5,677,427, each of which is hereby incorporated by reference. In general, the chimeric antibody can be prepared by obtaining cDNAs encoding the heavy and light chain variable regions of the antibodies, inserting the cDNAs into an expression vector, which upon being introduced into eukaryotic host cells, expresses the chimeric antibody of the present invention. Preferably, the expression vector carries a functionally complete constant heavy or light chain sequence so that any variable heavy or light chain sequence can be easily inserted into the expression vector.

The present invention provides a humanized antibody that specifically recognizes the epitope on CD43 and CEA expressed by a nonhematopoietic cancer cell. The humanized antibody is typically a human antibody in which residues from CDRs are replaced with residues from CDRs of a non-human species such as mouse, rat or rabbit having the desired specificity, affinity and capacity. In some instances, Fv framework residues of the human antibody are replaced by corresponding non-human residues.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; and 6,548,640. For example, the constant region may be engineered to more resemble human constant regions to avoid immune response if the antibody is used in clinical trials and treatments in humans. See, for example, U.S. Pat. Nos. 5,997,867 and 5,866,692.

It is important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. The humanized antibodies may also contain modifications in the hinge region to improve one or more characteristics of the antibody.

In another alternative, antibodies may be screened and made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines and bovines.

In certain embodiments, the antibody is a fully human antibody. Non-human antibodies that specifically bind an antigen can be used to produce a fully human antibody that binds to that antigen. For example, the skilled artisan can employ a chain swapping technique, in which the heavy chain of a non-human antibody is co-expressed with an expression library expressing different human light chains. The resulting hybrid antibodies, containing one human light chain and one non-human heavy chain, are then screened for antigen binding. The light chains that participate in antigen binding are then co-expressed with a library of human antibody heavy chains. The resulting human antibodies are screened once more for antigen binding. Techniques such as this one are further described in U.S. Pat. No. 5,565,332. In addition, an antigen can be used to inoculate an animal that is transgenic for human immunoglobulin genes. See, e.g., U.S. Pat. No. 5,661,016.

The antibody may be a bispecific antibody, a monoclonal antibody that has binding specificities for at least two different antigens, can be prepared using the antibodies disclosed herein. Methods for making bispecific antibodies are known in the art (see, e.g., Suresh et al., 1986, *Methods in Enzymology* 121:210). Traditionally, the recombinant production of bispecific antibodies was based on the coexpression of two immunoglobulin heavy chain-light chain pairs, with the two heavy chains having different specificities (Millstein and Cuello, 1983, *Nature* 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; and EP 03089). Heteroconjugate antibodies may be made using any convenient cross-linking methods. Suitable cross-linking agents and techniques are well known in the art, and are described in U.S. Pat. No. 4,676,980.

Single chain Fv fragments may also be produced, such as described in Iliades et al., 1997, *FEBS Letters*, 409:437-441. Coupling of such single chain fragments using various linkers is described in Kortt et al., 1997, *Protein Engineering*, 10:423-433. A variety of techniques for the recombinant production and manipulation of antibodies are well known in the art.

It is contemplated that the present invention encompasses not only the monoclonal antibodies described above, but also any fragments thereof containing the active binding region of the antibodies, such as Fab, F(ab')$_2$, scFv, Fv fragments and the like. Such fragments can be produced from the monoclonal antibodies described herein using techniques well established in the art (Rousseaux et al. (1986), in *Methods Enzymol.*, 121:663-69 Academic Press).

Methods of preparing antibody fragment are well known in the art. For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by U.S. Pat. Nos. 4,036,945 and 4,331,647 and references contained therein, which patents are incorporated herein by reference. Also, see Nisonoff et al. (1960), *Arch Biochem. Biophys.* 89: 230; Porter (1959), *Biochem. J.* 73: 119, Edelman et al., in *METHODS IN ENZYMOLOGY* VOL. 1, page 422 (Academic Press 1967).

Alternatively, the Fab can be produced by inserting DNA encoding Fab of the antibody into an expression vector for prokaryote or an expression vector for eukaryote, and introducing the vector into a prokaryote or eukaryote to express the Fab.

The invention encompasses modifications to antibodies or polypeptide described herein, including functionally equivalent antibodies which do not significantly affect their properties and variants which have enhanced or decreased activity and/or affinity. For example, amino acid sequence of antibody 5F1 or humanized antibody, may be mutated to obtain an antibody with the desired binding affinity to the CD43 or CEA expressed by the cancer cell. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the table below under the heading of "conservative substitutions". If such substitutions result in a change in biological activity, then more substantial changes, denominated "exemplary substitutions" in the table below, or as further described below in reference to amino acid classes, may be introduced and the products screened.

| Amino Acid Substitutions | | |
|---|---|---|
| Original Residue | Conservative Substitutions | Exemplary Substitutions |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
 (1) Non-polar: Norleucine, Met, Ala, Val, Leu, Ile;
 (2) Polar without charge: Cys, Ser, Thr, Asn, Gln;
 (3) Acidic (negatively charged): Asp, Glu;
 (4) Basic (positively charged): Lys, Arg;
 (5) Residues that influence chain orientation: Gly, Pro; and
 (6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyl transferase III (GnTIII), a glycosyl transferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5.278,299). Glycosylation, or certain types of glycosylation, can be enzymatically removed from the glycoprotein, for example using endoglycosidase H (Endo H), N-glycosidase F, endoglycosidase Fl, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

The antibody or polypeptide of the invention may be conjugated (for example, linked) to an agent, such as a therapeutic agent and a label. Examples of therapeutic agents are radioactive moieties, cytotoxins, or chemotherapeutic molecules.

The antibody (or polypeptide) of this invention may be linked to a label such as a fluorescent molecule, a radioactive molecule, an enzyme, or any other labels known in the art. As used herein, the term "label" refers to any molecule that can be detected. In a certain embodiment, an antibody may be labeled by incorporation of a radiolabeled amino acid. In a certain embodiment, biotin moieties that can be detected by marked avidin (e.g., streptavidin containing a fluorescent marker or enzymatic activity that can be detected by optical or colorimetric methods) may be attached to the antibody. In certain embodiments, a label may be incorporated into or attached to another reagent which in turn binds to the antibody of interest. For example, a label may be incorporated into or attached to an antibody that in turn specifically binds the antibody of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Examples of labels for polypeptides include, but are not limited to, the following: radioisotopes or radionucleoides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., fluorescein isothiocyanate (FITC), rhodamine, lanthanide phosphors, phycoerythrin (PE)), enzymatic labels (e.g., horseradish peroxidase, β-galactosidase, luciferase, alkaline phosphatase, glucose oxidase, glucose-6-phosphate dehydrogenase, alcohol dehydrogenase, malate dehyrogenase, penicillinase, luciferase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The invention also provides pharmaceutical compositions comprising antibodies or polypeptides described herein, and a pharmaceutically acceptable carrier or excipients. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

In some embodiments, the invention provides compositions (described herein) for use in any of the methods described herein, whether in the context of use as a medicament and/or use for manufacture of a medicament.

Polynucleotides, Vectors and Host Cells

The invention also provides polynucleotides comprising a nucleotide sequence encoding any of the monoclonal antibodies and polypeptides described herein. In some embodiments, the polypeptides comprise the sequences of light chain and heavy chain variable regions.

In some embodiments, the polynucleotides comprise a nucleic acid sequence encoding the heavy chain variable region set forth in SEQ ID NO:1, and/or a nucleic acid sequence encoding the light chain variable region set forth in SEQ ID NO:2. In some embodiments, the polynucleotides comprise a nucleic acid sequence encoding a heavy chain variable region comprising one, two, or three CDRs from SEQ ID NO:1, and/or a nucleic acid sequence encoding a light chain variable region comprising one, two, or three CDRs from SEQ ID NO:2. In some embodiments, the polynucleotides comprise a nucleic acid sequence set forth in SEQ ID NO:9, and/or a nucleic acid sequence set forth in SEQ ID NO:10.

In some embodiments, the polynucleotides comprise a nucleic acid sequence encoding the heavy chain variable region set forth in SEQ ID NO:3, and/or a nucleic acid sequence encoding the light chain variable region set forth in SEQ ID NO:4. In some embodiments, the polynucleotides comprise a nucleic acid sequence encoding a heavy chain variable region comprising one, two, or three CDRs from SEQ ID NO:3, and/or a nucleic acid sequence encoding a light chain variable region comprising one, two, or three CDRs from SEQ ID NO:4. In some embodiments, the polynucleotides comprise a nucleic acid sequence set forth in SEQ ID NO:11, and/or a nucleic acid sequence set forth in SEQ ID NO:12.

In some embodiments, the polynucleotides comprise a nucleic acid sequence encoding the heavy chain variable region set forth in SEQ ID NO:5, and/or a nucleic acid sequence encoding the light chain variable region set forth in SEQ ID NO:6. In some embodiments, the polynucleotides comprise a nucleic acid sequence encoding a heavy chain variable region comprising one, two, or three CDRs from SEQ ID NO:5, and/or a nucleic acid sequence encoding a light chain variable region comprising one, two, or three CDRs from SEQ ID NO:6. In some embodiments, the polynucleotides comprise a nucleic acid sequence set forth in SEQ ID NO:13, and/or a nucleic acid sequence set forth in SEQ ID NO:14.

In some embodiments, the polynucleotides comprise a nucleic acid sequence encoding the heavy chain variable region set forth in SEQ ID NO:7, and/or a nucleic acid sequence encoding the light chain variable region set forth in SEQ ID NO:8. In some embodiments, the polynucleotides comprise a nucleic acid sequence set forth in SEQ ID NO:15, and/or a nucleic acid sequence set forth in SEQ ID NO:16.

It is appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Thus, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein can, but need not, have an altered structure or function. Alleles can be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides can be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

The invention also provides vectors (e.g., cloning vectors, expression vectors) comprising a nucleic acid sequence encoding any of the polypeptides (including antibodies) described herein. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript® (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides or vectors described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Diagnostic uses

The present invention provides a method of using the antibodies, polypeptides and polynucleotides of the present invention for detection, diagnosis and monitoring of a disease, disorder or condition associated with the epitope expression (either increased or decreased relative to a normal sample, and/or inappropriate expression, such as presence of expression in tissues(s) and/or cell(s) that normally lack the epitope expression).

In some embodiments, the method comprises detecting the epitope expression in a sample obtained from a subject suspected of having cancer, such colorectal, pancreatic, gastric, and lung cancer. Preferably, the method of detection comprises contacting the sample with an antibody, polypeptide, or polynucleotide of the present invention and determining whether the level of binding differs from that of a control or comparison sample. The method is also useful to determine whether the antibodies or polypeptides described herein are an appropriate treatment for the patient.

As used herein, the term "a sample" or "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A sample" or "a biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "a sample" or "a biological sample" can also refer to cells or tissue analyzed in vivo, i.e., without removal from animal. Typically, "a sample" or "a biological sample" will contain cells from the animal, but the term can also refer to non-cellular biological material, such as non-cellular fractions of blood, saliva, or urine, that can be used to measure the cancer-associated polynucleotide or polypeptides levels. "A sample" or "a biological sample" further refers to a medium, such as a nutrient broth or gel in which an organism has been propagated, which contains cellular components, such as proteins or nucleic acid molecules.

In one embodiment, the cells or cell/tissue lysate are contacted with an antibody and the binding between the antibody and the cell is determined. When the test cells are shown binding activity as compared to a control cell of the same tissue type, it may indicate that the test cell is cancerous. In some embodiments, the test cells are from human tissues.

Various methods known in the art for detecting specific antibody-antigen binding can be used. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or (β-glactosidase), fluorescent moieties or proteins (e.g., fluorescein, rhodamine, phycoerythrin, GFP, or BFP), or luminescent moieties (e.g., Qdot® nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art.

In some embodiments, the polypeptides including antibodies of the invention need not be labeled, and the presence thereof can be detected using a labeled antibody which binds to the antibodies of the invention.

The antibodies of the present invention can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, or $^3$H) so that the cells or tissue of interest can be localized using immunoscintigraphy.

The antibody may also be used as staining reagent in pathology using techniques well known in the art.

Therapeutic uses

A striking and surprising feature of the antibodies of the present invention relates to their ability to effectively induce nonhematopoietic cancer cell death. Thus, the present invention provides therapeutic uses of the antibodies and polypeptides of the present invention in treating cancer, such as, colorectal cancer, lung cancer, pancreatic cancer, gastric cancer, breast cancer, hepatocellular carcinoma, and thyroid cancer. Any cancer may be treated, such as colon cancer, colorectal cancer, lung cancer, breast cancer, brain tumor, malignant melanoma, renal cell carcinoma, bladder cancer, lymphomas, T cell lymphomas, multiple myeloma, gastric cancer, pancreas cancer, cervical cancer, endometrial carcinoma, ovarian cancer, esophageal cancer, liver cancer, head and neck squamous cell carcinoma, cutaneous cancer, urinary tract carcinoma, prostate cancer, choriocarcinoma, pharyngeal cancer, laryngeal cancer, thecomatosis, androblastoma, endometrium hyperplasy, endometriosis, embryoma, fibrosarcoma, Kaposi's sarcoma, hemangioma, cavernous hemangioma, angioblastoma, retinoblastoma, astrocytoma, neurofibroma, oligodendroglioma, medulloblastoma, ganglioneuroblastoma, glioma, rhabdomyosarcoma, hamartoblastoma, osteogenic sarcoma, leiomyosarcoma, thyroid sarcoma and Wilms tumor, as long as the cancer cell expresses the epitope recognized by the antibodies described herein. The method may further comprise a step of detecting the binding between an antibody or a polypeptide described herein and a tumor or, cancer cell in an individual to be treated.

Generally, an effective amount of a composition comprising an antibody or a polypeptide is administered to a subject in need of treatment, thereby inhibiting growth of the cancer cell and/or inducing death of the cancer cell. Preferably the composition is formulated with a pharmaceutically acceptable carrier.

In one embodiment, the composition is formulated for administration by intraperitoneal, intravenous, subcutaneous, and intramuscular injections, and other forms of administration such as oral, mucosal, via inhalation, sublingually, etc.

In another embodiment, the present invention also contemplates administration of a composition comprising the antibodies or polypeptides of the present invention conjugated to other molecules, such as detectable labels, or therapeutic or cytotoxic agents. The agents may include, but are not limited to radioisotopes, toxins, toxoids, inflammatory agents, enzymes, antisense molecules, peptides, cytokines, or chemotherapeutic agents. Methods of conjugating the antibodies with such molecules are generally known to those of skilled in the art. See, e.g., PCT publications WO 92/08495; WO 91/14438; WO 89/12624; U.S. Pat. No. 5,314,995; and EP 396,387; the disclosures of which are incorporated herein by reference in their entireties.

In one embodiment, the composition comprises an antibody or polypeptide conjugated to a cytotoxic agent. Cytotoxic agents can include any agents that are detrimental to cells. A preferred class of cytotoxic agents that can be conjugated to the antibodies or fragments may include, but are not limited to paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The dosage required for the treatment depends on the choice of the route of administration, the nature of the formulation, the nature of the subject's illness, the subject's size, weight, surface area, age and sex; other drugs being administered, and the judgment of the attending physician. Suitable dosages are in the range of 0.01-1000.0 mg/kg.

Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight; or less, is administered. For repeated administrations over several days or longer, depending on the condition, the treatment is sustained until a desired suppression of disease symptoms occurs. An exemplary dosing regimen comprises administering a weekly dose of about 6 mg/kg of the antibody. However, other dosage regimens may be useful, depending on the pattern of pharmacokinetic decay that the practitioner wishes to achieve. Empirical considerations, such as the half-life, generally will contribute to determination of the dosage. The progress of this therapy is easily monitored by conventional techniques and assays.

In some subjects, more than one dose may be required. Frequency of administration may be determined and adjusted over the course of therapy. For example, frequency of administration may be determined or adjusted based on the type and stage of the cancer to be treated, whether the agent is administered for preventive or therapeutic purposes, previous therapy, the patient's clinical history and response to the agent, and the discretion of the attending physician. Typically the clinician will administer a therapeutic antibody (such as humanized 5F1), until a proper dosage is reached to achieves the desired result. In some cases, sustained continuous release formulations of antibodies may be appropriate. Various formulations and devices for achieving sustained release are known in the art.

In one embodiment, dosages for the antibodies or polypeptides may be determined empirically in subjects who have been given one or more administration(s). Subjects are given incremental dosages of the antibodies or polypeptides. To assess efficacy of the antibodies or polypeptides, markers of the disease symptoms such as CD43 or CEA can be monitored. Efficacy in vivo can also be measured by assessing tumor burden or volume, the time to disease progression (TDP), and/or determining the response rates (RR).

Administration of an antibody or polypeptide in accordance with the method in the present invention can be continuous or intermittent, depending, for example, upon the recipient's physiological condition, whether the purpose of the administration is therapeutic or prophylactic, and other factors known to skilled practitioners. The administration of an antibody or a polypeptide may be essentially continuous over a preselected period of time or may be in a series of spaced dose.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In another embodiment, the composition can comprise one or more anti-cancer agents, one or more antibodies described herein, or with an antibody or polypeptide that binds to a different antigen. Such composition can contain at least one, at least two, at least three, at least four, at least five different antibodies. The antibodies and other anti-cancer agents may be in the same formulation (e.g., in a mixture, as they are often denoted in the art), or in separate formulations but are administered concurrently or sequentially, are particularly useful in treating a broader range of population of individuals.

A polynucleotide encoding any of the antibodies or polypeptides of the present invention (such as antibody 5F1 or humanized form) can also be used for delivery and expression of any of the antibodies or polypeptides of the present invention in a desired cell. It is apparent that an expression vector can be used to direct expression of the antibody or polypeptide. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding any of the antibodies or polypeptides of the present invention can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al. (1990), *Proc. Natl. Acad Sci. USA,* 87:3655; Wu et al. (1991), *J. Biol. Chem.* 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol.

The therapeutic polynucleotides and polypeptides of the present invention can be delivered using gene delivery vehicles. The gene delivery vehicle can be of viral or non-viral origin (see generally, Jolly (1994), *Cancer Gene Therapy* 1:51; Kimura (1994), *Human Gene Therapy* 5:845; Connelly (1985), *Human Gene Therapy* 1:185; and Kaplitt (1994), *Nature Genetics* 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242; alphavirus-based vectors, e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors, e.g., PCT Publication Nos. WO 94/12649, WO 93/03769; WO 93/19191; WO 94/28938; WO 95/11984 and WO 95/00655. Administration of DNA linked to killed adenovirus as described in Curiel (1992), *Hum. Gene Ther.* 3:147 can also be employed.

Non-viral delivery vehicles and methods can also be employed, including, but are not limited to, polycationic condensed DNA linked or unlinked to killed adenovirus alone (see, e.g., Curiel (1992), *Hum. Gene Ther.* 3:147); ligand-linked DNA (see, e.g., Wu (1989), *J. Biol. Chem.* 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes.

Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent NO. 0 524 968. Additional approaches are described in Philip (1994), *Mol. Cell Biol.* 14:2411 and in Woffendin (1994), *Proc. Natl. Acad. Sci.* 91:1581.

The composition comprising an antibody of the present invention can be administered sequentially or concurrently with one or more other therapeutic agents such as chemotherapeutic agents (such as 5-FU, 5-FU/MTX, 5-FU/Leucovorin, Levamisole, Irinotecan, Oxaliplatin, Capecitabin, or Uracil/Tegafur), immunoadjuvants, growth inhibitory agents, cytotoxic agents and cytokines, etc. The amounts of the antibody and the therapeutic agent depend on what type of drugs are used, the pathological condition being treated, and the scheduling and routes of administration but would generally be less than if each were used individually.

Following administration of the composition comprising the antibody described herein, the efficacy of the composition can be evaluated both in vitro and in vivo by various methods well known to one of ordinary skill in the art. Various animal models are well known for testing anti-cancer activity of a candidate composition. These include human tumor xenografting into athymic nude mice or scid/scid mice, or genetic murine tumor models such as p53 knockout mice. The in vivo nature of these animal models make them particularly predictive of responses in human patients. Such models can be generated by introducing cells into syngeneic mice using standard techniques, e.g., subcutaneous injection, tail vein injection, spleen implantation, intraperitoneal implantation and implantation under the renal capsule, etc.

Kits

The invention also provides kits for use in the instant methods. Kits of the invention include one or more containers comprising a purified antibody or a polypeptide described herein and instructions for use in accordance with any of the methods of the invention described herein. In some embodiments, these instructions comprise a description of administration of the antibody to treat a nonhematopoietic cancer, such as colorectal cancer, according to any of the methods described herein. The kit may further comprise a description of selecting an individual suitable for treatment based on identifying whether that individual has the disease and the stage of the disease, or whether the epitope is expressed on the cancer cells in the individual.

In some embodiments, the kits for detecting a cancer cell in a sample comprise an antibody or a polypeptide described herein and reagents for detecting binding of the antibody or the polypeptide to a cell in the sample.

The instructions relating to the use of the antibodies or polypeptides to treat cancer generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating a cancer described herein. Instructions may be provided for practicing any of the methods described herein.

The kits of this invention are in suitable packaging. Suitable packaging includes, but is not limited to, vials, bottles, jars, flexible packaging (e.g., sealed Mylar® or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an antibody described herein. The container may further comprise a second pharmaceutically active agent.

Kits may optionally provide additional components such as buffers and interpretive information. Normally, the kit comprises a container and a label or package insert(s) on or associated with the container.

EXAMPLES

The following Examples are provided to illustrate but not to limit the invention.

Example 1

Generation and Characterization of Monoclonal Antibodies that Specifically Binds to CD43 Expressed on Cancer Cells Generation of Monoclonal Antibodies Human colorectal adenocarcinoma cell line, COLO 205 (ATCC CCL-222), was purchased from Food Industry Research and Development Institute (CCRC 60054), Hsinchu, Taiwan, and grown in RPMI 1640 medium (GIBCO BRL) with 10% FBS (Hyclone), 100 units/ml of penicillin and 100 µg/ml of streptomycin (GIBCO BRL) at 37° C. in a humidified atmosphere of 5% CO2. A female 8-week Balb/c mouse was immunized three times with $2 \times 10^7$ COLO 205 cells in 500 µl PBS or 10 micro-gram of partial purified protein in CFA every two weeks and finally were given a boost of $2 \times 10^6$ COLO 205 cells or 10 micro-gram of partial purified protein in 200 µl PBS. Five days after the final boost, the spleen cells were fused with X63 myeloma cells. Hybridomas were selected with DMEM supplemented with 10% FBS (Hyclone) and HAT (Hybri-Max™, Sigma H0262, at a final concentration of 100 µM hypoxanthine, 0.4 µM aminopterin, 16 µM thymidine). Three hybridoma cell lines m5F1, m51-41, m138-10, which secrete the monoclonal antibody 5F1, 51-41, and 138-10, have been generated.

Identification and Characterization of the Target Antigen for Monoclonal Antibody 5F1

Membrane proteins from colorectal cancer tissues or COLO 205 cells were isolated with extraction buffer (50 mM Tris-HCl, pH 7.4, 150 mM NaCl, 1% Nonidet P-40) containing protease inhibitors (Complete tabs; Roche Molecular Biochemicals). Membrane protein lysates were first pre-cleared on a 1-ml column containing non-immune mouse IgG immobilized on Protein G Sepharose® (Amersham Pharmacia Biotech Inc., N.J., U.S.A), and the flow-through portion was directly applied onto a 1-ml column of 5F1 coupled to Protein G-Sepharose®. Column was washed and the target protein of 5F1 was eluted. The purity of the isolated protein was visualized by silver staining and also identified by Western blotting after separation on 8% SDS-PAGE. The isolated protein was also used to immunize mice to generate other 5F1-like antibodies such as 138-10 or 51-41.

For immunoprecipitation experiments, the membrane proteins were incubated with 5F1 or an anti-CD43 antibody (AF2038, R&D System, Inc.) followed by incubation with protein G Sepharose® (Amersham Pharmacia Biotech Inc., N.J., U.S.A.). The precipitates were run on 8% SDS-PAGE and subjected to Western (or immuno) blot analysis.

Proteins were mixed with an equal volume of sample buffer (50 mM Tris-HCl, pH 6.8, 100 mM DTT, 2% SDS, 0.1% bromophenol blue, 10% glycerol), separated by 8% SDS-PAGE and then transferred to a nitrocellulose membrane (Hybond™-C Super, Amersham). The nitrocellulose membrane was then blocked with 5% skimmed milk in PBS, and incubated with 5F1 or anti-CD43 mAb (AF2038). Blot was then treated with horseradish peroxidase-conjugated goat anti-mouse immunoglobulin (Jackson ImmunoResearch Laboratories, West Grove, Pa.) and developed with chemiluminescence reagents (ECL, Amersham, UK).

To test whether 5F1 does recognize CD43, a commercially available anti-CD43 mAb (AF2038, R&D system, Inc.) was used to confirm the identity of 5F1 affinity-purified protein from COLO 205 lysates by Western blot analysis. The lysates from a 5F1 binding negative cell line COLO 320 were used as control. Our results (FIG. 1) showed that both the anti-CD43 (AF2038) and 5F1 antibodies reacted with the protein captured by 5F1 immunoaffinity column, strongly suggesting that 5F1 does recognize CD43.

Monoclonal Antibody 5F1 Specifically Recognizes CD43 Expressed on Cell Surface of Nonhematopoietic Cancer Cells.

$2 \times 10^5$ COLO 205 cells were seeded in each well of a v-bottomed 96-well plate and incubated with different concentrations of 5F1 antibody, ranging from 0.33 to 1 µg/ml, at 4° C. for 1 hr. Cells were washed twice with 200 µl FACS buffer (1×PBS+1% FBS), stained with 100 of 1 µg/ml (in FACS buffer) goat-anti-mouse IgG-PE (Southern Biotech.), and then incubated at 4° C. for 30 min. Cells were washed thrice with FACS buffer and analyzed by flow cytometry (BD LSR, BD Life Sciences).

Figure 2A:
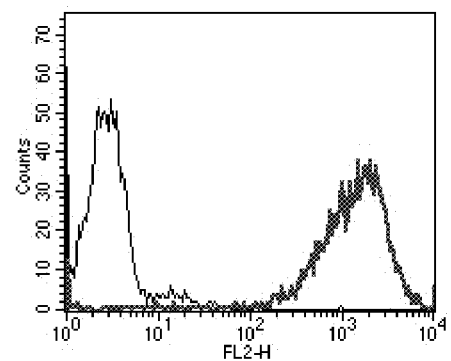
FIG. 2A shows the results of flow cytometric analysis of antibody 5F1 binding to three cancer cell lines: colorectal cancer cells (COLO 205 and DLD-1), and gastric cancer cell (NCI-N87).
Figure 2A:
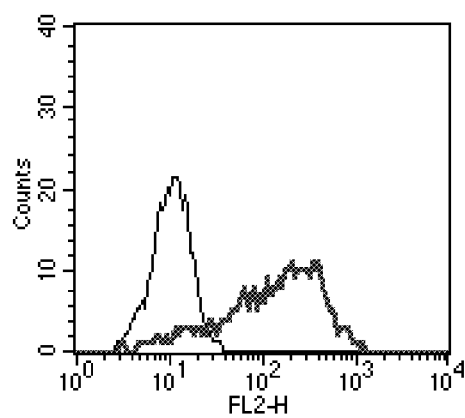
Figure 2A:
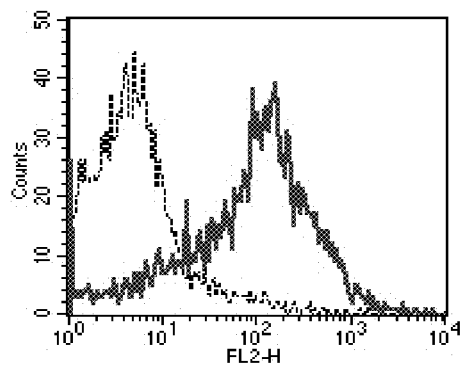
Figure 2B:
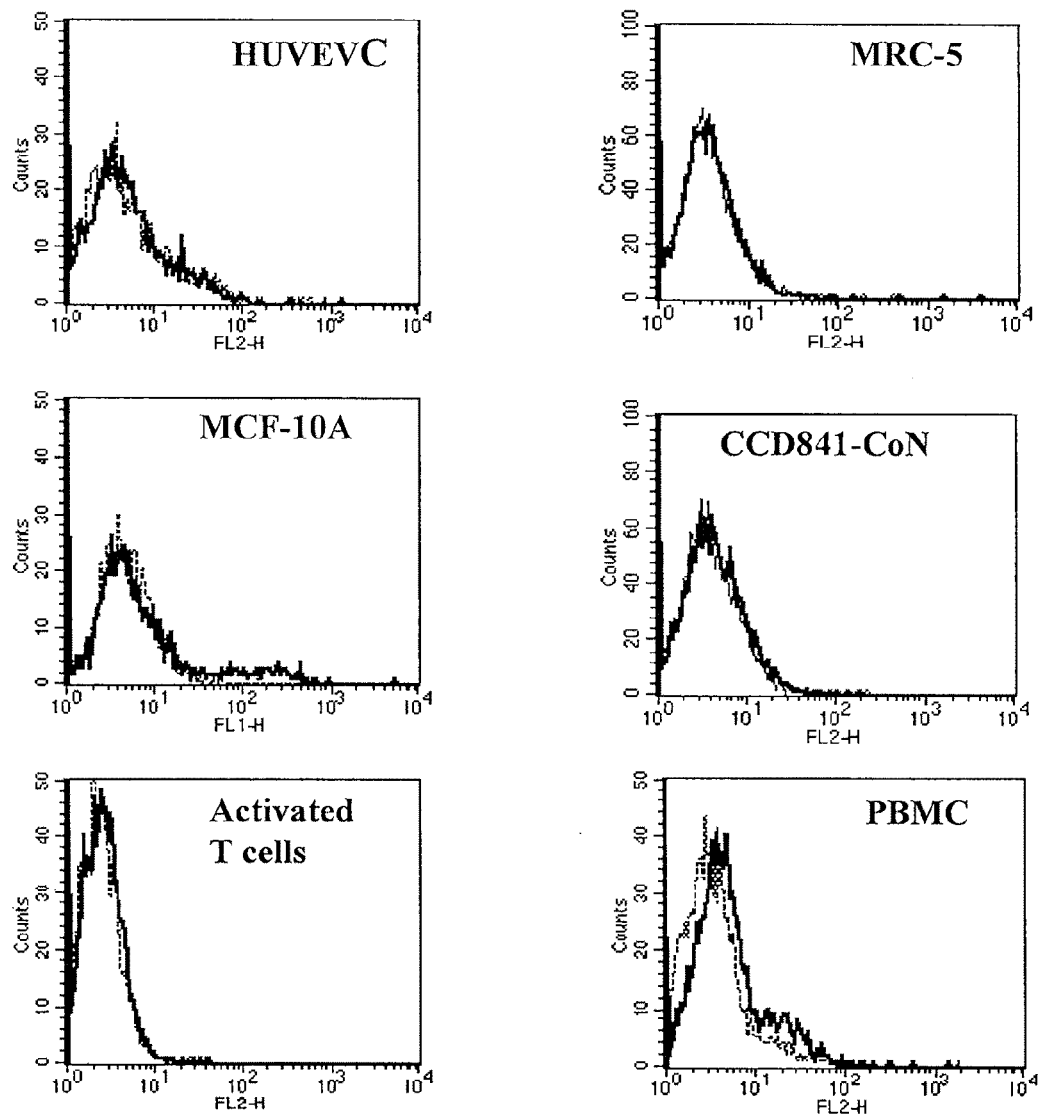
FIG. 2B shows the results of flow cytometric analysis of antibody 5F1 binding to normal endothelial cells (HUVEC), normal (embryonic) lung cells (MRC-5), normal mammary gland epithelial cells (MCF-10A), normal colorectal cells (CCD841-CoN), activated T lymphocytes (activated for seven days), or normal peripheral blood mononuclear cells (PBMC).

Antibody binding results from flow cytometry are shown in Table 1 below. Monoclonal antibody such as 5F1 (isotype: IgG3), or 138-10 (isotype IgM), or 51-41 (isotype IgM) recognizes a surface CD43 expressed on the cytoplasmic membranes of COLO 205 colorectal cancer cells and NCI-N87 gastric cancer cells, but not peripheral T nor Jurkat (a lymphoblastoid leukemia cell line; ATCC TIB-152). See Table. 1 below. Flow cytometry data (FIG. 2A and FIG. 2B) also show 5F1 binds to other types of cancer cells, such as colorectal cancer cells (DLD-1), and gastric cancer cells (NCI-N87), but not normal endothelial cells (HUVEC), normal lung cells (MRC-5), normal mammary gland epithelial cells (MCF-10A), normal colorectal cells (CCD841-CoN), activated T lymphocytes (activated for seven days), or normal peripheral blood mononuclear cells (PBMC).

Table 1 shows antigen-binding properties of anti-CD43 antibodies such as 5F1, 138-10, or 51-41 to colorectal cancer, gastric cancer cells, human peripheral T cells, and Jurkat (a lymphoblastoid leukemia cell line).

| % of Binding/ Abs | Peripheral T cells | Jurkat (Leukemia cells) | COLO 205 | NCI-N87 (Gastric cancer cells) |
|---|---|---|---|---|
| 5F1 | <10% | <10% | >80% | >80% |
| 138-10 | <10% | <10% | >80% | >80% |
| 51-41 | <10% | <10% | >80% | >80% |
| Anti-CD162 | >80% | >80% | <10% | Not tested |
| MEM-59 (anti-CD43; Biovendor, Candler, NC) | >80% | Not tested | >70% | Not tested |
| Isotype control Ab | <10% | <10% | <10% | <10% |

To detect the expression of the target protein of 5F1 in COLO 205 cells and human colorectal cancer tissues, a routine immunohistochemical method was used. Briefly, cells or tissues were fixed for immunostaining with 1 µg/ml of 5F1, incubated with biotin-labeled anti-mouse IgG, then incubated with avidin-biotin peroxidase complex (Vector Laboratories, Inc. Burlingame, Calif., U.S.A.), and stained with the chromogen 3,3'-diaminobenzidine tetrachloride. Immunohistochemical study showed that 52.5 percent of the tissues from patients with colorectal cancer (31/59) stained positive with 5F1.

Example 2

Apoptotic Activity of Antibodies that Specifically Bind to CD43 Expressed on Cancer Cells Detection of Apoptosis Induced by 5F1 in COLO 205 Cells by ELISA Assay To evaluate the type of cell death induced by 5F1, colorectal cancer cells were grown in culture plates and incubated with or without 5F1. The level of internucleosomal (apoptotic) DNA fragmentation was determined by antibody-mediated capture and detection of cytoplasmic mononucleosome- and oligonucleosome-associated histone-DNA complexes using the Cell Death Detection ELISA$^{PLUS}$ kit (Roche, Cat#1774425). The ELISA assay was performed according to the manufacturer's instruction. Briefly, $1 \times 10^4$ COLO 205 cells were plated in each well of 96-well plates and incubated with 5F1 or 9E10 (an anti-myc antibody) at the concentration of 10 µg/ml, or with medium control. After 6, 24 or 48 hr of incubation at 37° C., cells were washed and incubated with 200 µl of lysis buffer for 30 min. After pelleting nuclei (200×g, 10 min.), 20 µl of the supernatant (cytoplasmic fraction) containing fragmented DNA was transferred to streptavidin-coated microtiter plates that had been incubated with biotinylated monoclonal antihistone antibody. The amount of fragmented DNA of nucleosomes bound to anti-histone antibody was evaluated by peroxidase-conjugated monoclonal anti-DNA antibody using ABTS (2,2-azino-di[3-ethylbenzthiazoline sulfonate-6-diammonium salt]) as a substrate. Finally, absorbance at 405 nm, upon incubating with a peroxidase substrate for 10-20 min., was determined with a microplate reader (Molecular Devices, SpectraMax® M2). Values from wells containing lysis buffer and substrate only were subtracted as background. The data were analyzed as the specific enrichment of mono- and oligonucleosomes released into the cytoplasm from the values using the following formula:

$$\text{Enrichment factor } (E.F.) = \frac{mU \text{ of the sample (dying/dead cells)}}{mU \text{ of the medium control}}$$

(cells without mAb treatment)

$mU$ = absorbance $[10^{-3}]$

Figure 3:
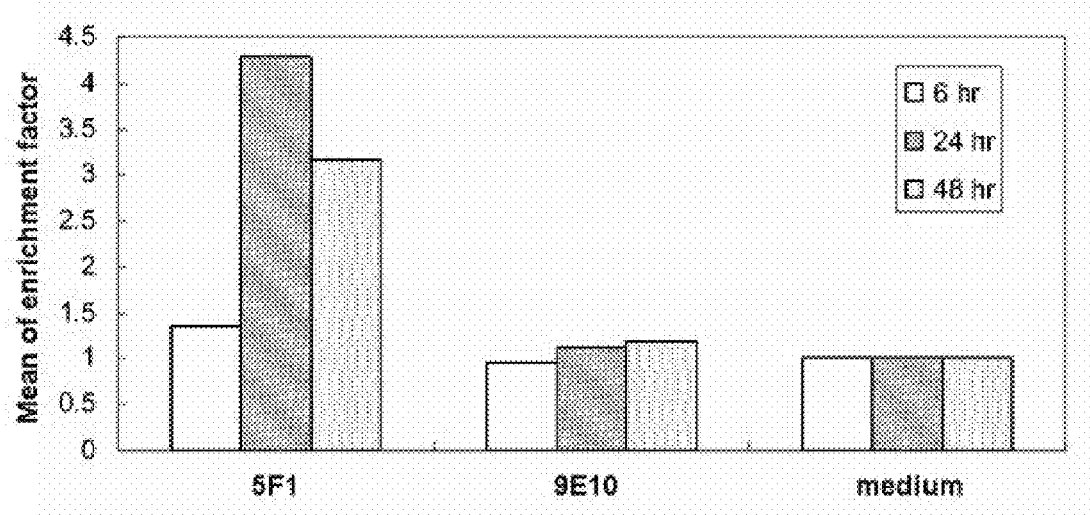
FIG. 3 shows mean enrichment of nucleosomes in the cytoplasm of COLO 205 cells after incubation in the presence of antibody 5F1 or 9E10 (an anti-myc antibody), or control medium for 6, 24, and 48 hours.

Data shown in FIG. 3 indicate that 5F1 induced an enrichment of nucleosomes in the cytoplasm of COLO 205 cells after 24 hr of incubation. The detected fragmented DNA in the 5F1 treated cytoplasm was increased more than 4-fold as compared to medium control. Such enrichment was not observed in the cells treated with either control antibody 9E10 (an anti-myc antibody) or medium alone, indicating that 5F1 alone caused cancer cells to undergo apoptosis.

Detection of Apoptosis Induced by 5F1, 138-10, and 51-41 in COLO 205 Cells Using Annexin V and PI Staining Annexin V stains the phospholipids that flips toward the outer side of the cytoplasmic membrane at the early stage of the apoptosis process. Thus, staining of Annexin V, as assayed by FACS analysis, indicates the cells undergoing apoptosis. $1.2 \times 10^5$ COLO 205 cells were seeded to each well of a 96-well plate, and then various concentrations of 5F1 (2-16 µg/ml) diluted in the medium or fresh medium (untreated control) was added into the cells. To test whether the cross-linker (CL) is needed for 5F1 to induce apoptosis in tumor cells, 20 µg/ml of rabbit anti-mouse IgG (Jackson ImmunoResearch, Cat#315-005-045) was added into a set of samples for comparison. After a 6-hr incubation at 37° C., the cells were stained with 0.25 µl of FITC-conjugated Annexin V (Strong Biotech Corporation) in 100 µl Annexin V binding buffer at room temperature for 15 min. The cells were then stained with propidium iodide (PI, a DNA staining dye) and analyzed by flow cytometry.

Flow cytometry data showed that treatment of 5F1, in the absence of the cross-linker, for 6 hours at concentration of 4 µg/ml or higher caused significant number of colorectal cancer cells to undergo apoptosis, suggesting that 5F1 alone could effectively induce apoptosis in COLO 205 cells.

Effect of inducing apoptosis of COLO 205 cells by other anti-C43 antibodies, 138-10 and 51-41, was also tested. Table 2 below shows 5F1, 138-10, or 51-41 induced apoptosis in colorectal cancer cells. The COLO 205 cells were incubated with 32 micro-gram/ml of each antibody for 6 hours and stained with annexin-V and then PI, followed by FACS analysis.

TABLE 2

Induction of apoptosis in COLO 205 cells by 5F1, 138-10, and 51-41.

|  | 5F1 | 138-10 | 51-41 | Control Ab (negative control) |
|---|---|---|---|---|
| % Apoptosis (annexin-V$^+$) | >40% | >30% | >30% | <15% |

The above results show that treatments with antibodies specific for cancer expressed CD43 can induce apoptosis in a cancer cell.

Figure 10:
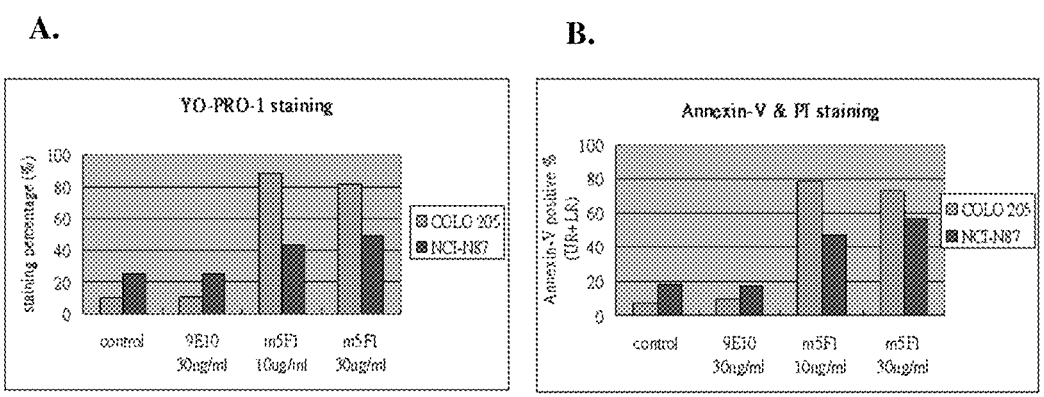
FIG. 10 shows staining of COLO 205 and NCI-N87 cells for apoptotic cell death after incubation with various antibodies. COLO 205 and NCI-N87 cells were incubated overnight with control, 9E10 (30 ug/ml), m5F1 (10 ug/ml), or m5F1 (30 ug/ml). Cells were then stained with YO-PRO®-1 (A) or combined Annexin-V & PI (B). Staining percentage for each condition is shown in the bar graph.

Detection of Apoptosis Induced by m5F1 in NCI-87 Cells Using YO-PRO®-1 Staining or Annexin V and PI Staining $4 \times 10^5$ cells of NCI-N87 (human gastric carcinoma cell line) or $5 \times 10^5$ cells of COLO 205 were seeded in 12-well culture plate (Nunc Catalog #150628). After overnight culture, medium was changed, and antibodies at concentrations as indicated in FIG. 10 or azide were added for 6 hours incubation. Then, the cells were trypsinized and collected for staining with YO-PRO®-1 (Invitrogen, Catalog #Y3603) or double staining with Annexin-V-FITC & PI (Strong Biotech, apoptosis detection kits, Catalog #AVK250).

As shown in FIGS. 10A and 10B, antibody m5F1 induced apoptosis in NCI-87 and COLO 205 cells as measured by YO-PRO®-1 staining (A) and by double staining with Annexin-V-FITC and PI (B). These data indicate that m5F1 can also induce apoptosis in gastric carcinoma cells.

Example 3

Inhibition of Cancer Cell Growth by 5F1

5F1 Alone Inhibits the Growth of Cancer Cells

Colorectal cancer cells (COLO 205), and normal endothelial cells (HUVEC) were seeded and incubated with 5F1 or a control antibody 9E10. Also included were untreated cells as negative controls. Cell survival was evaluated using MTT & WST-1 assays to detect proliferative activity as described herein.

Figure 4:
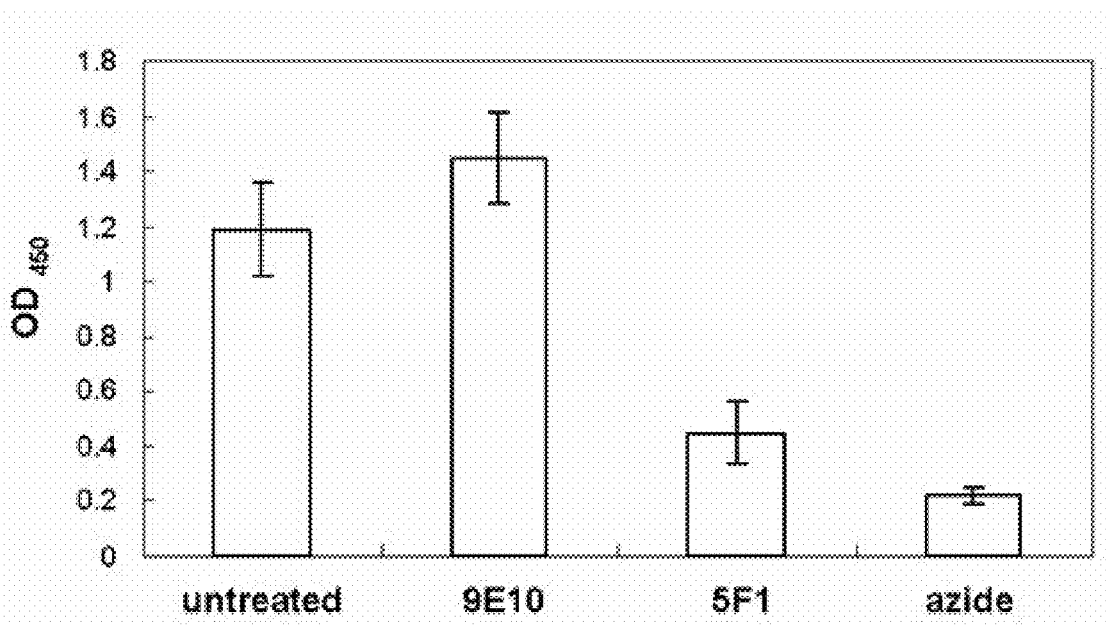
FIG. 4 shows the results of cell growth of COLO 205 measured by WST-1 assay after incubation with antibody 5F1, 9E10, or azide in vitro for 72 hr.

WST-1 assay is based on the cleavage of the tetrazolium salt WST-1 to formazan by cellular mitochondrial dehydrogenases. The formazan produced can be quantified by spectrophotometer by measuring absorbance at 450 nm. Proliferation of viable cells results in an increase in the overall activity of the enzymes; and decrease in the enzymatic activity indicates cell growth inhibition. Thus, WST-1 assay was used to evaluate the survival rate of tumor cells after 5F1 treatment. Briefly, $4\times10^3$ COLO 205 cells in 100 µl culture medium were seeded in 5 duplicates for each treatment in a 96-well culture plate. Then 10 µg/ml of 5F1, control antibody 9E10 (an anti-myc antibody) or fresh medium (untreated control) was added. The treatment of 0.5% sodium azide ($NaN_3$) was also included in the assay as a cytotoxicity control. After a three-day incubation period at 37° C., 20 µl of WST-1 reagent (Roche, Cat#1664807) was added to each well and the mixture was incubated at 37° C. for 30 min. Absorbance at 450 nm was obtained to reflect the survival rate of the treated cells. The results of WST-1 assay for COLO 205 cells are shown in FIG. 4. Data indicated that growth of COLO 205 cells was substantially inhibited (FIG. 4) while that of HUVEC (data not shown) was not influenced by 5F1 treatment. The percentage of survival rate was reduced to less than 50% in the antibody 5F1 treated as compared to isotype control antibody 9E10 treated colorectal cancer cells. The positive control group treated with 0.5% sodium azide showed 19% survival rate.

Figure 5:
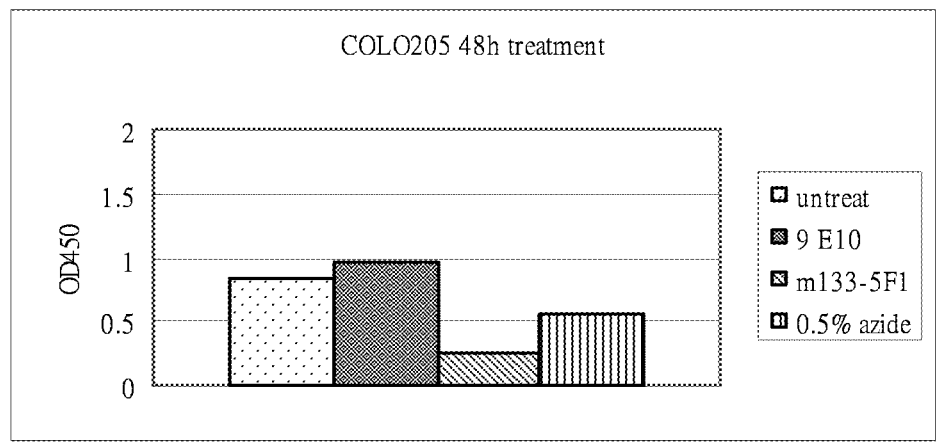
FIG. 5 shows the results of cell growth measured by WST-1 assay. Colorectal carcinoma cells COLO 205 and normal colorectal cell line CCD841-CoN, were either untreated, or incubated with 9E10, 5F1 (referred to as "m133-5F1"), or 0.5% azide.
Figure 5:
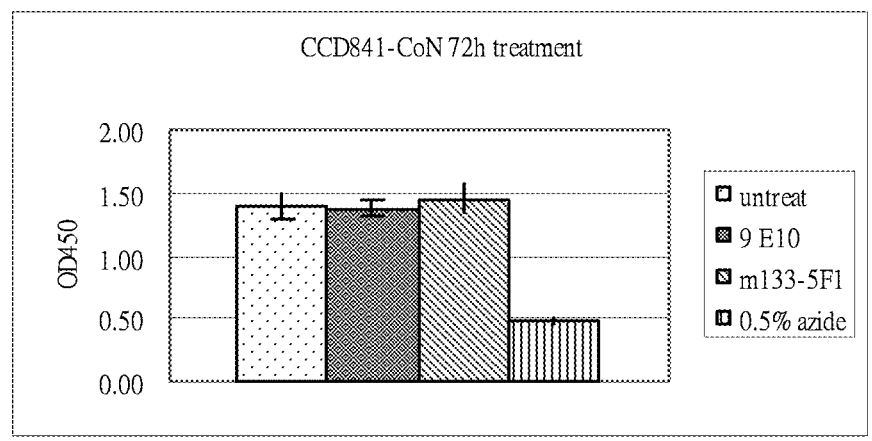

In another experiment, cells ($2\times10^3$) were seeded in each well of a 96-well culture plate and incubated with 10 microgram/ml of monoclonal antibody 5F1 or control antibody 9E10 (an antibody against c-myc). Untreated cells were used as negative controls; and cells treated with 0.5% sodium azide were used as positive controls. After a two- or three-day incubation period at 37° C., 10 ul of WST-1 Reagent were added to each well and the cells were further incubated for 30 min. WST-1 cell survival assay was then conducted as described above. The results, shown in FIG. 5, indicated that growth of colorectal carcinoma cells, such as COLO 205, was substantially inhibited by antibody 5F1, but normal colorectal cell line (such as CCD841-CoN was not effected.

Figure 6:
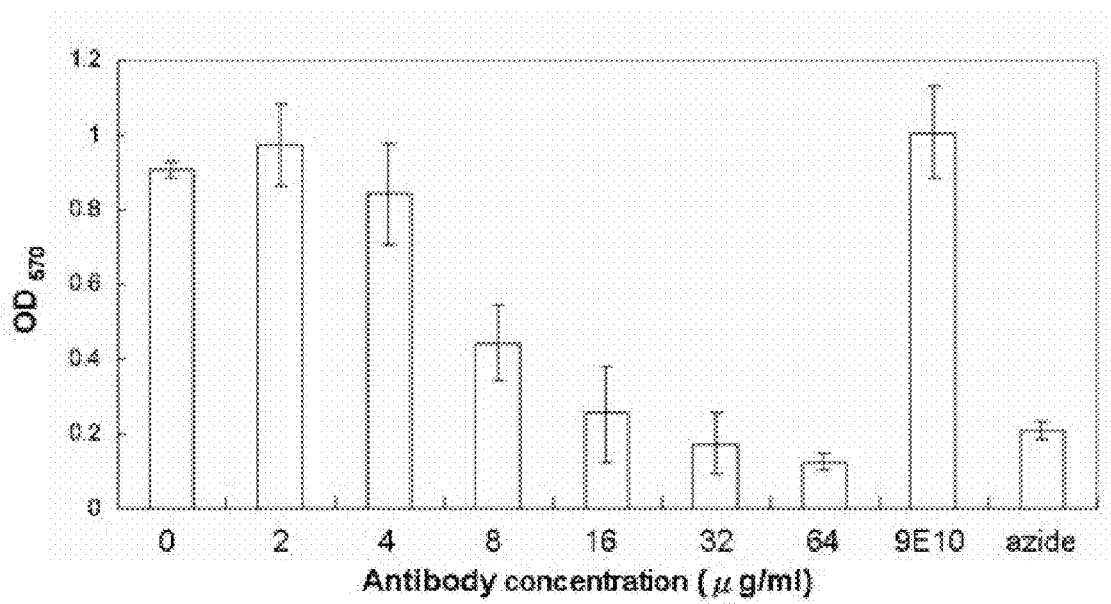
FIG. 6 shows the results of MTT staining of COLO 205 cells after incubation with various concentration of 5F1 (0, 2, 4, 8, 16, 32, 64 ug/ml), 9E10 (64 ug/ml) or 0.5% azide.

MTT is another tetrazolium-based method for the measurement of cell viability and proliferation. The yellow tetrazolium MTT (3-(4,5-dimethylthiazolyl-2)-2,5-diphenyltetrazolium bromide) is reduced by metabolically active cells, in part by the action of dehydrogenase enzymes, to generate reducing equivalents such as NADH and NADPH. The resulting intracellular purple formazan can be solubilized and quantified by spectrophotometric means. Cells ($5\times10^3$) were seeded in each well of a 96-well culture plate and incubated with monoclonal antibody 5F1(concentration range from 0-64 µg/ml) or a control antibody 9E10(64 µg/ml) against c-myc. Untreated cells were used as negative controls; and cells treated with 0.5% sodium azide were used as positive controls. After 72-hr incubation period at 37° C., 10 µl of MTT Reagent were added to each well and the cells were further incubated for 2-4 hr until purple precipitate is visible. 100 ul detergent reagent (DMSO) is added. Absorbance of samples at 570 nm is recorded. Data from MTT assay demonstrated that 5F1 inhibited cell proliferation of COLO 205 in a dose-dependent manner (from 0 to 64 µg/ml) and the ED50 (effective dose for 50% inhibition) was 8 µg/ml (FIG. 6). As also indicated in the FIG. 6, a remarkable inhibition of cell growth was found when 64 µg/ml of 5F1 was used while control antibody 9E10 had no such effect at the same concentration.

Evaluation of Anti-tumor Effects of SF1 In Vivo

The in vivo anti-tumor effects of SF1 were analyzed in a tumor xenograft mouse model. $5\times10^6$ COLO 205 cells were implanted subcutaneously into the hind flank region of SCID mice on day 0. A week after the inoculation of cells, in one experiment, mice were treated with 500 micro-gram of SF1 or PBS by intra-peritoneal injection. In another experiment, four groups of mice (6 mice in each group) bearing established tumors were intravenously treated every other day with four doses of 25 mg/kg of 5-fluorouracil plus leucovorin (5 FU/LV), and with or without various doses of SF1 intraperitoneal injection twice weekly.

Figure 7:
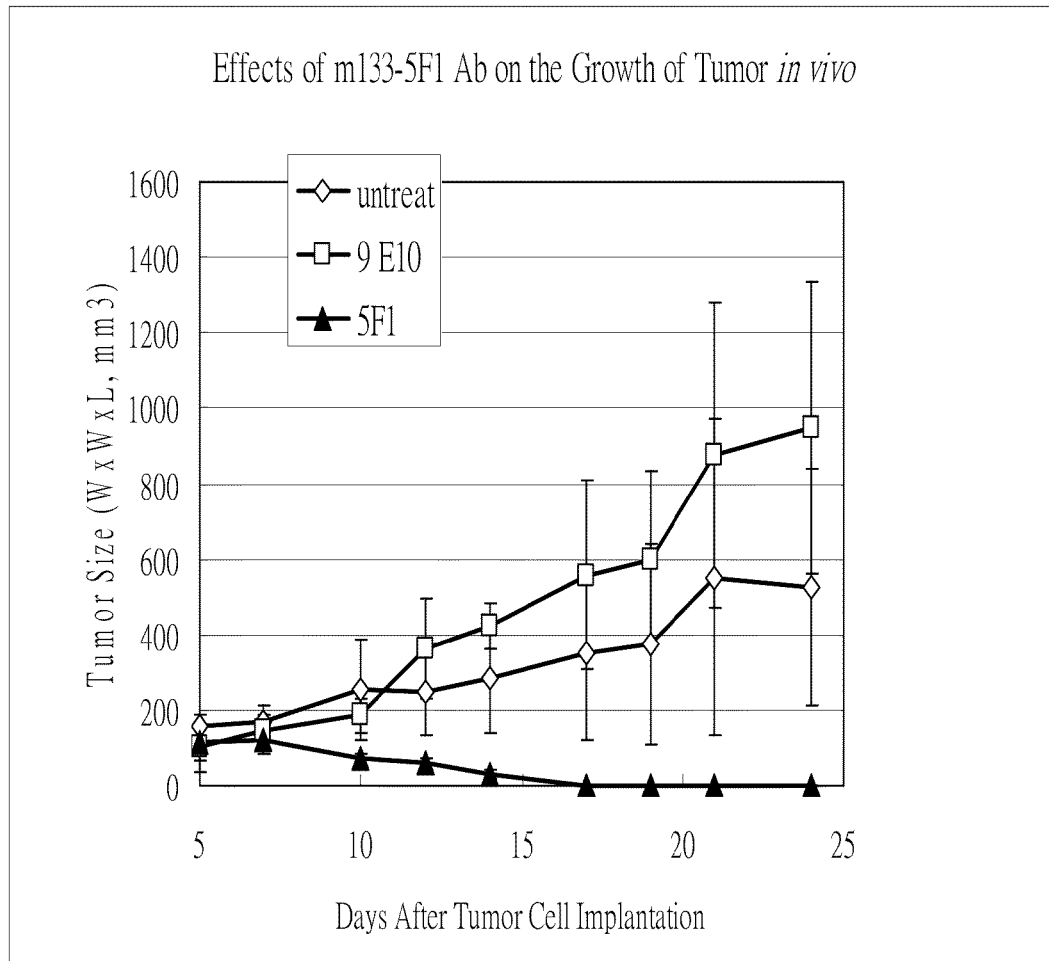
FIG. 7 shows in vivo effects (on tumor size) of antibody 5F1 (also referred to as "m133-5F1") on human COLO 205 tumors in SCID mice. Antibody 5F1 (at 500 µg/injection), or control antibody 9E10 (at 500 µg/injection), or PBS (untreated) was injected on days 0, 3, 5, 7, 10, 12, 14, and 17.

In one experiment, tumor implantation in SCID mice were achieved by subcutaneous injection of colorectal cancer cell COLO 205 at $1\times10^7$ cells per mouse at day 0 and then treated by intraperitoneal injection of monoclonal antibody SF1 (at 500 µg per dose) or control monoclonal antibody 9E10 (an antibody raised against c-myc) or PBS at days 0, 3, 5, 7, 10, 12, 14, and 17. Fifteen mice were used in each group of the experiment. Tumor size was measured starting from day S up to day 24 by the product of the width, width, and length (W×W×L) and expressed by $mm^3$. As shown in FIG. 7, monoclonal antibody SF1 effectively suppressed the tumor growth as compared to the control antibody 9E10 and PBS (untreated).

Figure 8:
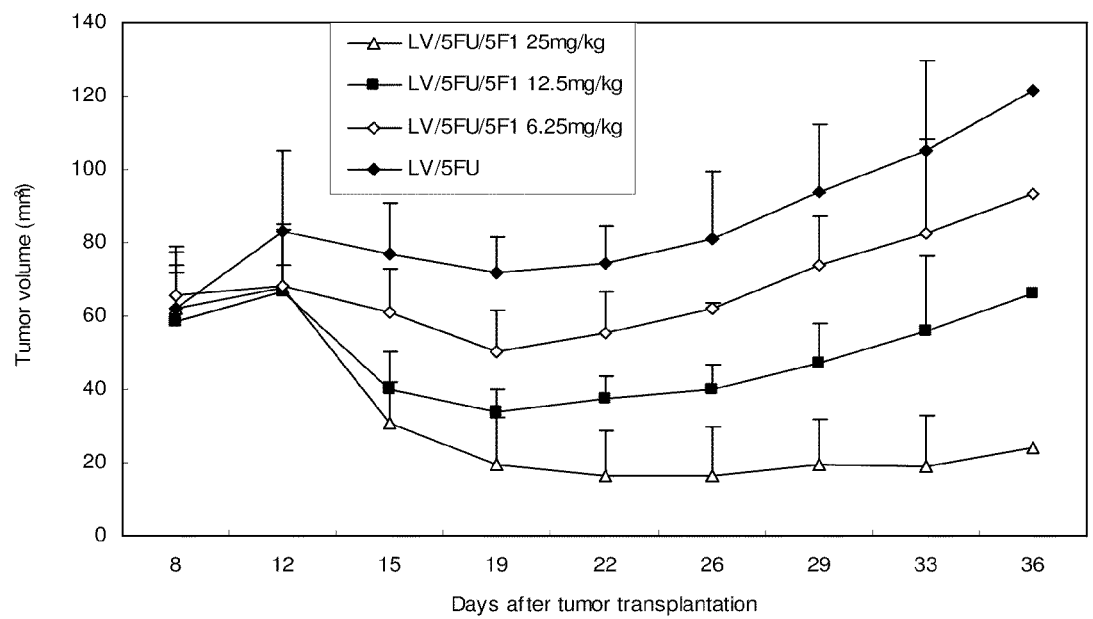
FIG. 8 shows in vivo effects (on tumor size) of antibody 5F1 with chemical drugs 5FU/LV on human COLO 205 tumors in SCID mice. 5FU/LV was intravenously injected every other day with four doses of 25 mg/kg a week after the inoculation of COLO 205 cells. Antibody 5F1 was intraperitoneally injected at 0, 6.25 mg/kg, 12.5 mg/kg, and 25 mg/kg twice weekly for 3 weeks post 7 days of tumor implant.

To see the combined effects of SF1 and chemo-drugs like 5FU/LV, mice were iv injected with 25 mg/kg of 5FU/LV every other day for 4 doses and ip injected with or without various amounts of SF1 antibodies twice weekly for 3 weeks post 7 days of tumor implant. Tumor growth was assessed based on twice-weekly measurement of tumor volume ($mm^3$) by calipers and the tumor size was calculated using the formula: $\pi/6\times$larger diameter$\times$(smaller diameter)$^2$ (Kievit E, Cancer Research,60:6649-55). As shown in FIG. 8, the combination of 5F1 antibody and 5FU/LV treatments significantly inhibited the human colorectal tumor growth compared to those of chemo-drug treated alone (FIG. 8).

Example 4

Three Novel Anti-CD43 Antibodies, SF1, 138-10, and 51-41, Recognize Similar Epitope Expressed on Cancer Cells To understand the binding property of three novel anti-CD43 antibodies (5F1, 138-10, and 51-41), FACS analysis was used. COLO 205 cells (100,000) were stained with 1 micro gram/ml of biotinylated 5F1 at 4 degree C. for 1 hr in the presence of various amounts of non-biotinylated antibody 5F1, 138-10, and 51-41. After washes, the cells were further stained with streptavidin-FITC at the same condition for 30 min. The cells were washed and analyzed by FACS. Data shown in Table 3 below are mean Fluorescence Intensity from one representative experiment. Both 51-41 and 138-10 antibodies were able to compete the binding of biotinylated-5F1 to COLO 205 cells suggesting that all three antibodies bind on the similar binding site expressed on the surface of COLO 205 cells.

TABLE 3

5F1, 138-10, and 51-41 recognize similar epitopes expressed on COLO 205 cells.

| Competing antibody concentration (microgram/ml) | Mean Fluorescence Intensity in the presence of unlabeled 5F1, 51-41, or 138-10 | | |
|---|---|---|---|
| | 5F1 | 51-41 | 138-10 |
| 200 | 9.78 | 75.66 | 199.7 |
| 66.7 | 60.28 | 165.62 | 297.03 |
| 22.2 | 21.67 | 325.23 | 395.53 |
| 7.4 | 129.04 | 606.20 | 640.42 |
| 2.46 | 733.36 | 783.81 | 702.79 |
| 0.82 | 1004 | 789.23 | 724.15 |
| 0.273 | 1027 | 901.36 | 683.08 |
| 0.09 | 825 | 869.61 | 717.19 |
| 0.03 | 888 | 860.13 | 704.33 |

Example 5

Epitope Determination of Antibody 5F1

To further define the epitope structure recognized by the monoclonal antibody 5F1, this monoclonal antibody was used to test its specific reactivity to different polypeptide sequences. 96-well microtiter plates were coated with antibody 5F1 with 50 µl per well at the concentration of 10 µg/ml in 0.1 M NaHCO3 (pH 8.6) coating buffer over night at 4° C. After wash, the plates were blocked by incubation with blocking buffer containing 0.1 M NaHCO3 (pH 8.6), 5 mg/ml BSA, 0.02% NaN$_3$ (150 µl /well) for at least one hour at 4° C. Plates were then incubated with fusion proteins containing various fragments of polypeptides at the various concentrations for one hour at room temperature. After wash with 0.5% Tween® containing TBS, the bound fusion protein-polypeptides were eluted with 1 mg/ml BSA containing 0.2M Glycine-HCl (pH 2.2) buffer and neutralized with 1 M Tris-HCl (pH 9.1). The amino acid sequence of eluted fusion protein-polypeptides were then determined. The polypeptides that antibody 5F1 binds contain a tripeptide sequence of Trp-Pro-Ile (WPI), from N-terminus to C-terminus. This tripeptide amino acid sequence is not present in the CD43 amino acid sequence. Pallant et al., Proc. Natl. Acad. Sci. USA 86:1328-32, 1989; Shelley et al., Proc. Natl. Acad. Sci. USA 86:2819-23, 1989.

To further confirm the tripeptide epitope that antibody 5F1 binds, Sandwich ELISA was performed. 96-well microtiter plates were coated with antibody (5F1 or control antibody 9E10) with 50 µl per well at the concentration of 1 µg/ml over night at 4° C. Plates were blocked by incubation with 0.25% of BSA in PBS(150 µl/well) for 1 hour at 37° C. Plates were then incubated with fusion proteins containing various fragments of polypeptides fused to a carrier protein for 2 hours at room temperature. After washing 4 times with PBS containing 0.05% of Tween® 20, plates were then incubated with carrier protein-specific antibody at 2 µg/ml for 1.5 hours at room temperature. After incubation, plates were washed 4 times with PBST. 50 µl of 1 to 3000 diluted Goat anti-carrier protein-specific antibody conjugated with HRP was then added to each well and the plates were incubated for 1 hour at 37° C. Enzyme reaction was carried out by adding substrate of the HRP enzyme to determine the reactivity of the designated polypeptide to these to these two antibodies (5F1 and 9E10). Table 4 below shows the data from ELISA assay when 5F1 or 9E10 was immobilized on the plate. "+" indicates the designated polypeptide binds to the monoclonal antibody; and "–" indicates the designated polypeptide does not bind to the monoclonal antibody. Monoclonal antibody 5F1 recognized a tripeptide WPI epitope structure. Since the tripeptide WPI sequence is not present in CD43, these data suggest that 5F1 recognizes a conformational epitope which includes a structure having physical and/or chemical characteristics similar or equivalent to the structure formed by tripeptide WPI.

TABLE 4

Epitope structures recognized by 5F1

| Peptide Name | Amino cid sequences | 5F1 | 9E10 |
|---|---|---|---|
| 5F1-01-2-21 | W P I D L M S E T P I L (SEQ ID NO: 17) | + | – |
| 5F1-01-2-04 | W P I A N H E N A L S A (SEQ ID NO: 18) | + | – |
| 5F1-01-2-18 | W P I S G K H S F W S L (SEQ ID NO: 19) | + | – |
| 5F1-01-2-17 | W P I L D H A V S R P S (SEQ ID NO: 20) | + | – |
| 5F1-01-2-16 | W P I D I P Y A W D F S (SEQ ID NO: 21) | + | – |
| 5F1-01-2-13 | W P I S P Q P G A R P V (SEQ ID NO: 22) | + | – |
| 5F1-01-2-09 | W P I A P N R Y L L S S (SEQ ID NO: 23) | + | – |
| 5F1-01-2-06 | W P I P P E V E P F K H (SEQ ID NO: 24) | + | – |
| 5F1-01-2-05 | W P I L Q N A A G T G L (SEQ ID NO: 25) | + | – |
| 5F1-01-2-23 | W P I P T L M E L P S A (SEQ ID NO: 26) | + | – |
| 5F1-01-2-22 | W P I T N S D S R I T W (SEQ ID NO: 27) | + | – |
| 5F1-01-2-14 | W P I H S A H V R Y T T (SEQ ID NO: 28) | + | – |
| 9F9-01-03-24 | A E T D Y D P D H F T P (SEQ ID NO: 29) | – | – |
| 9F9-01-03-18 | D A R Y S H D P A W P Y (SEQ ID NO: 30) | – | – |
| 9F9-01-03-17 | A G Q K W D P E W P H S (SEQ ID NO: 31) | – | – |
| 9F9-01-03-21 | Y D H H W T N P P T Q K (SEQ ID NO: 32) | – | – |
| 9F9-01-03-25 | E P N M D P N W A S P S (SEQ ID NO: 33) | – | – |

Example 6

Cloning of the Variable Regions of Light and Heavy Chains of 5F1, 138-10, and 51-41, and Antibody Humanization The variable region cDNAs of 5F1 light and heavy chains were amplified by PCR, and the synthesized cDNAs were subcloned into pCRII (Invitrogen) for sequence determination. Nucleotide sequences were obtained from several independent clones and analyzed. Identical cDNA sequence from independent clones was chosen to represent the light or heavy chain V region of each antibody. Table 5 below showed the translated amino acid sequences of and nucleotide sequences encoding the light and heavy chain V regions of 5F1, 138-10, 51-41, and humanized 5F1 (h5F1Vc).

TABLE 5

Amino acid sequences of the antibodies' variable regions, and nucleic acid sequences encoding the antibodies' variable regions (CDRs are underlined)

5F1 heavy chain amino acid sequence (SEQ ID NO: 1) and nucleotide sequence (SEQ ID NO: 9)
```
  1 M   E   W   S   W   I   F   L   F   L   L   S   G   T   A   G   V   H   S   E
  1 ATGGAATGGAGTTGGATATTTCTCTTTCTCCTGTCAGGAACTGCAGGTGTCCACTCTGAG 21 V   Q   L   Q   Q   S   G   P   E   L   V   K   P   G   A   S   V   R   M   S
 61 GTCCAGCTGCAGCAGTCTGGACCTGAGCTGGTAAAGCCTGGGGCTTCAGTGAGGATGTCC 41 C   T   A   S   G   Y   T   F   T   S   Y   V   M   H   W   I   K   Q   K   P
121 TGCACGGCTTCTGGATACACATTCACTAGCTATGTTATGCACTGGATAAAGCAGAAGCCT 61 G   Q   G   L   D   W   I   G   Y   I   N   P   Y   N   G   G   T   Q   Y   N
181 GGGCAGGGCCTTGACTGGATTGGATATATTAATCCTTACAATGGTGGTACTCAGTACAAT 81 E   K   F   K   G   K   A   T   L   T   S   D   K   S   S   S   T   A   Y   M
241 GAGAAGTTCAAAGGCAAGGCCACACTGACTTCAGACAAATCCTCCAGCACAGCCTACATG 101 E   L   S   S   L   T   S   E   D   S   A   V   Y   Y   C   A   R   R   T   F
301 GAGCTCAGCAGCCTGACCTCTGAGGACTCTGCGGTCTATTACTGTGCAAGACGGACCTTC 121 P   Y   Y   F   D   Y   W   G   Q   G   T   T   L   T   V   S   S
361 CCGTACTACTTTGACTACTGGGGCCAAGGCACCACTCTCACAGTCTCCTCA
```

5F1 light chain amino acid sequence (SEQ ID NO: 2) and nucleotide sequence (SEQ ID NO: 10)
```
  1 M   K   L   P   V   R   L   L   V   L   M   F   W   I   P   A   S   S   S   D
  1 ATGAAGTTGCCTGTTAGGCTGTTGGTGCTGATGTTCTGGATTCCTGCTTCCAGCAGTGAT 21 V   L   M   T   Q   T   P   L   S   L   P   V   S   L   G   D   Q   A   S   I
 61 GTTTTGATGACCCAAACTCCACTCTCCCTGCCTGTCAGTCTTGGAGATCAAGCCTCCATC 41 S   C   R   S   S   Q   S   I   L   H   S   N   G   N   T   Y   L   E   W   Y
121 TCTTGCAGATCTAGTCAGAGCATTTTACATAGTAATGGAAACACCTATTTAGAATGGTAC 61 L   Q   K   P   G   Q   S   P   K   L   L   I   Y   K   V   S   N   R   F   S
181 CTGCAGAAACCAGGCCAGTCTCCAAAGCTCCTGATCTACAAAGTTTCCAACCGATTTTCT 81 G   V   P   D   R   F   S   G   S   G   S   G   T   D   F   T   L   K   I   S
241 GGGGTCCCAGACAGGTTCAGTGGCAGTGGATCAGGGACAGATTTCACACTCAAGATCAGC
101 R   V   E   A   E   D   L   G   V   Y   Y   C   F   Q   G   S   H   A   P   L
301 AGAGTGGAGGCTGAGGATCTGGGAGTTTACTACTGCTTTCAAGGTTCACATGCTCCTCTC 121 T   F   G   A   C   T   K   L   E   L   K
361 ACGTTCGGTGCTGGGACCAAGCTGGAGCTGAAA
```

138-10 heavy chain amino acid sequence (SEQ ID NO: 3) and nucleotide sequence (SEQ ID NO: 11)
```
  1 M   E   C   N   W   I   L   P   F   I   L   S   V   I   S   C   V   V   S   E
  1 ATGGAATGTAACTGGATACTTCCTTTTATTCTGTCGGTAATTTCAGGGGTCTACTCAGAG 21 V   Q   L   Q   Q   S   G   T   V   L   A   R   P   G   A   S   V   K   M   S
 61 GTTCAGCTCCAGCAGTCTGGGACTGTGCTGGCAAGGCCTGGGGCTTCCGTGAAGATGTCC 41 C   K   A   S   G   V   S   F   I   S   Y   W   M   H   W   V   K   Q   R   P
121 TGCAAGGCTTCTGGCTACAGCTTTATCAGCTACTGGATGCACTGGGTAAAACAGAGGCCT 61 G   Q   G   L   E   W   I   G   A   I   S   P   G   D   S   D   T   T   Y   N
181 GGACAGGGTCTAGAATGGATTGGTGCTATTTCTCCTGGAGATAGTGATACTACCTACAAC 81 Q   R   F   T   G   K   A   K   L   T   A   V   T   S   A   S   T   A   V   M
241 CAGAGGTTCACGGGCAAGGCCAAACTGACTGCAGTCACATCCGCCAGCACTGCCTACATG 101 E   L   S   S   L   T   N   E   D   S   A   V   Y   Y   C   I   R   R   D   G
301 GAGCTCAGCAGCCTGACAAATGAGGACTCTGCGGTCTATTATTGTATAAGAAGGGATGGT 121 N   Y   Q   V   A   W   F   A   Y   W   G   Q   G   T   L   V   T   V   S   A
361 AACTACCAAGTTGCCTGGTTTGCTTACTGGGGCCAAGGGACTCTGGTCACTGTCTCTGCA
```

TABLE 5-continued

Amino acid sequences of the antibodies' variable regions, and nucleic acid sequences encoding the antibodies' variable regions (CDRs are underlined)

138-10 light chain amino acid sequence (SEQ ID NO: 4) and
nucleotide sequence (SEQ ID NO: 12)
```
  1 M  K  L  P  V  R  L  L  V  L  M  F  W  I  P  A  S  S  S  D
  1 ATGAAGTTGCCTGTTAGGCTGTTGGTGCTGATGTTCTGGATTCCTGCTTCCAGCAGTGAT 21 V  L  M  T  Q  T  P  L  S  L  P  V  S  L  G  D  Q  A  S  I
 61 GTTTTGATGACCCAAACTCCACTCTCCCTGCCTGTCAGTCTTGGAGATCAAGCCTCCATC 41 S  C  R  S  S  Q  S  I  V  H  S  N  G  N  T  Y  L  E  W  Y
121 TCTTGCAGATCTAGTCAGAGCATTGTACATAGTAATGGAAACACCTATTTAGAATGGTAC 61 L  Q  K  P  G  Q  S  P  K  L  L  I  Y  K  V  S  N  R  F  S
181 CTGCAGAAACCAGGCCAGTCTCCAAAGCTCCTGATCTACAAAGTTTCCAACCGATTTTCT 81 G  V  P  D  R  F  S  G  S  G  S  G  T  D  F  T  L  K  I  S
241 GGGGTCCCAGACAGGTTCAGTGGCAGTGGATCAGGGACAGATTTCACACTCAAGATCAGC 101 R  V  E  A  E  D  L  G  V  Y  Y  C  F  Q  G  S  H  V  P  F
301 AGAGTGGAGGCTGAGGATCTGGGAGTTTATTACTGCTTTCAAGGTTCACATGTTCCATTC

121 T  F  G  S  G  T  K  L  E  I  K
361 ACGTTCGGCTCGGGGACAAAGTTGGAAATAAAA
```

51-41 heavy chain amino acid sequence (SEQ ID NO: 5) and
nucleotide sequence (SEQ ID NO: 13)
```
  1 M  E  C  N  W  I  L  P  F  I  L  S  V  I  S  G  V  Y  S  E
  1 ATGGAATGTAACTGGATACTTCCTTTTATTCTGTCGGTAATTTCAGGGGTCTACTCAGAG 21 V  Q  L  Q  Q  S  G  T  V  L  A  R  P  G  A  S  V  K  M  S
 61 GTTCAGCTCCAGCAGTCTGGGACTGTGCTGGCAAGGCCTGGGGCTTCCGTGAAGATGTCC 41 C  K  A  S  G  Y  S  F  T  S  Y  W  M  H  W  V  K  Q  R  T
121 TGCAAGGCTTCTGGCTACAGTTTTACCAGCTACTGGATGCACTGGGTAAAACAGAGGACT 61 G  Q  G  L  E  W  I  G  A  I  S  P  G  D  G  D  T  T  Y  N
181 GGGCAGGGTCTAGAATGGATTGGTGCTATTTCTCCTGGAGATGGTGATACTACCTACAAC 81 Q  K  F  T  G  K  A  K  L  T  A  V  T  S  A  S  T  A  Y  M
241 CAGAAGTTCACGGGCAAGGCCAAACTGACTGCAGTCACATCCGCCAGCACTGCCTACATG 101 E  L  S  S  L  T  H  E  D  S  A  V  Y  Y  C  T  R  R  D  G
301 GAGCTCAGCAGCCTGACACATGAGGACTCTGCGGTCTATTACTGTACAAGAAGAGATGGT 121 S  Y  Q  V  A  W  F  A  Y  W  G  R  G  T  L  V  T  V  S  A
361 AGCTACCAAGTTGCCTGGTTTGCTTACTGGGGCCGAGGGACTCTGGTCACTGTCTCTGCA
```

51-41 light chain amino acid sequence (SEQ ID NO: 6) and
nucleotide sequence (SEQ ID NO: 14)
```
  1 M  K  L  P  V  R  L  L  V  L  M  F  W  I  P  V  S  S  S  D
  1 ATGAAATTGCCTGTTAGGCTGTTGGTGCTGATGTTCTGGATTCCTGTTTCCAGCAGTGAT 21 V  L  M  T  Q  T  P  L  S  L  P  V  S  L  G  D  Q  A  S  I
 61 GTTTTGATGACCCAAACTCCACTCTCCCTGCCTGTCAGTCTTGGAGATCAAGCCTCCATC 41 S  C  R  S  S  Q  S  I  V  H  S  N  G  N  T  Y  L  E  W  F
121 TCTTGCAGATCTAGTCAGAGCATTGTCCATAGTAATGGAAACACCTATTTAGAATGGTTC 61 L  Q  K  P  G  Q  S  P  K  L  L  I  Y  K  V  S  N  R  F  S
181 CTGCAGAAACCAGGCCAGTCTCCAAAGCTCCTGATCTACAAAGTTTCCAACCGATTTTCT 81 G  V  P  D  R  F  S  G  S  G  S  G  T  D  F  T  L  K  I  S
241 GGGGTCCCAGACAGGTTCAGTGGCAGTGGATCAGGGACAGATTTCACACTCAAGATCAGC 101 R  V  E  A  E  D  L  G  V  Y  Y  C  F  Q  G  S  H  V  P  F
301 AGAGTGGAGGCTGAGGATCTGGGAGTTTATTACTGCTTTCAAGGTTCACATGTTCCATTC

121 T  F  G  S  G  T  K  L  E  I  K
361 ACGTTCGGCTCGGGGACAAAGTTGGAAATAAAA
``` h5F1Vc heavy chain amino acid sequence (SEQ ID NO: 7) and
nucleotide sequence (SEQ ID NO: 15)
```
  1 M  G  W  S  W  I  F  L  F  L  L  S  G  T  A  G  V  H  S  Q
  1 ATGGGATGGAGCTGGATCTTTCTCTTCCTCCTGTCAGGTACCGCGGGCGTGCACTCTCAG 21 V  Q  L  V  Q  S  G  A  E  V  K  K  P  G  S  S  V  K  V  S
 61 GTCCAGCTTGTCCAGTCTGGGGCTGAAGTCAAGAAACCTGGCTCGAGCGTGAAGGTCTCC
```

TABLE 5-continued

Amino acid sequences of the antibodies' variable regions, and nucleic acid sequences encoding the antibodies' variable regions (CDRs are underlined)

```
 41 C   K   A   S   G   Y   T   F   T   S   Y   V   M   H   W   V   R   Q   A   P
121 TGCAAGGCTTCTGGCTACACCTTTACTAGCTATGTTATGCACTGGGTAAGGCAGGCCCCT

61 C   Q   G   L   E   W   I   G   Y   I   N   P   Y   N   G   G   T   Q   Y   N
181 GGACAGGGTCTGGAATGGATTGGATATATTAATCCTTACAATGGTGGTACTCAGTACAAT

81 E   K   F   K   G   K   A   T   I   T   A   D   E   S   T   N   T   A   Y   M
241 GAGAAGTTCAAAGGCAAGGCCACAATTACTGCAGACGAATCCACCAATACAGCCTACATG

101 E   L   S   S   L   T   S   E   D   S   A   V   Y   Y   C   A   R   R   T   F
301 GAACTGAGCAGCCTGACATCTGAGGACAGCGCAGTCTATTACTGTGCAAGACGGACCTTC

121 P   Y   Y   F   D   Y   W   G   Q   G   T   T   L   T   V   S   S
361 CCGTACTACTTTGACTACTGGGGCCAAGGAACCACGCTCACAGTCTCCTCA h5F1Vc light chain amino acid sequence (SEQ ID NO: 8) and
nucleotide sequence (SEQ ID NO: 16)
  1 M   E   T   D   T   L   L   L   W   V   L   L   L   W   V   P   G   S   T   G
  1 ATGGAGACCGATACCCTCCTGCTATGGGTCCTCCTGCTATGGGTCCCAGGATCAACCGGA 21 D   I   Q   M   T   Q   S   P   S   S   L   S   A   S   V   G   D   R   V   T
 61 GATATTCAGATGACCCAGTCTCCATCTTCCCTCTCTGCTAGCGTCGGGGATAGGGTCACC 41 I   T   C   R   S   S   Q   S   I   L   H   S   N   G   N   T   Y   L   E   W
121 ATAACCTGCAGATCTAGTCAGAGCATTTTACATAGTAATGGAAACACCTATTTAGAATGG 61 Y   Q   Q   K   P   G   K   A   P   K   L   L   I   Y   K   V   S   N   R   F
181 TACCAGCAGAAGCCAGGCAAAGCTCCCAAGCTTCTAATCTATAAAGTTTCCAACCGATTT 81 S   G   V   P   S   R   F   S   G   S   G   S   G   T   D   F   T   L   T   I
241 TCTGGAGTCCCTTCACGCTTCAGTGGCAGTGGATCTGGGACCGATTTCACCCTCACAATC 101 S   S   L   Q   P   D   D   F   A   T   Y   Y   C   F   Q   G   S   H   A   P
301 AGCTCTCTGCAGCCAGATGATTTCGCCACTTATTACTGCTTTCAAGGTTCACATGCTCCT 121 L   T   F   G   Q   G   T   K   V   E   L   K
361 CTCACGTTCGGTCAGGGGACCAAGGTGGAGCTGAAA
```

Example 7

Production and Characterization of Chimeric 5F1 Antibody Construction and Production of Chimeric Antibody 5F1 (c5F1)

To construct vectors for expressing chimeric antibody, the light chain V region of 5F1 was subcloned into the plasmid pVk. pVk contains a CMV promoter, and the human light chain constant region. The sequence and biological information on the human light chain constant region can be found in Hieter, P. A., et al. (1980), *Cloned human and mouse kappa immunoglobulin constant and J region genes conserve homology in functional segments.* Cell, 22(1 Pt 1): p. 197-207.

The heavy chain V region of 5F1 was subcloned into plasmid pVg1. pVg1 plasmid has a CMV promoter and contains the human heavy chain constant region of IgG1. The sequence and biological information on the human IgG1 heavy chain constant region can be found in Ellison, J. W., B. J. Berson, and L. E. Hood (1981), *The Nucleotide sequence of a human immunoglobulin C gamma 1 gene.*, Nucleic Acids Res. 10:4071.

The light and heavy chain expressing plasmids were then co-transfected into Cos-7 cells. The supernatants containing c5F1 were collected and analyzed for the apoptosis-inducing function of c5F1.

Functional Tests of c5F1

Figure 9:
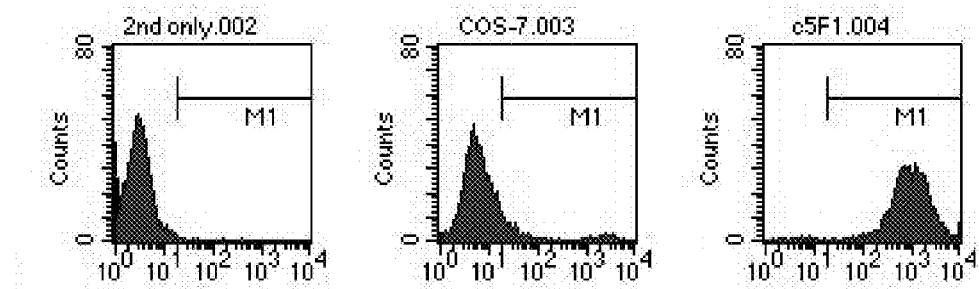
FIG. 9A shows flow cytometry results of chimeric antibody 5F1 binding to COLO 205 cell.
FIGS. 9B shows percentage of annexin V and PI positive cells after incubation of COLO 205 cells with control medium (untreated), sodium azide (0.5%), mouse antibody 5F1 (m5F1, 2-32 µg/ml), or chimeric antibody 5F1 (c5F1, 2-32 µg/ml).
Figure 9:
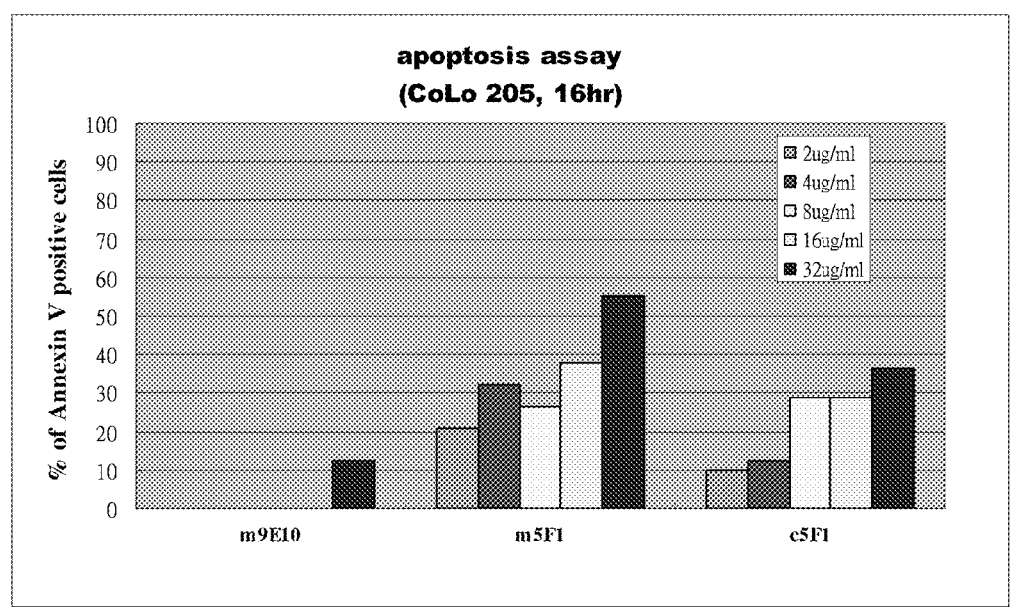

The supernatant containing c5F1 was then tested for its binding to COLO 205 cells by surface staining and for its function by Annexin V apoptosis assay as described above. For binding assay, 0.58 micro gram/ml of c5F1 was used. For apoptosis assay, 2-32 micro gram/ml of m5F1, c5F1 and 9E10 (anti-myc control antibody) were used and the incubation was for 16 hours. The supernatant containing c5F1 binds COLO 205 cells and induces apoptosis in COLO 205 cells, just as its mouse counterpart, demonstrating that the cloned cDNA fragments indeed encode the V regions of 5F1 (FIG. 9A and FIG. 9B).

Example 8

Colorectal Cancer Tissue Immunohistochemistry Study with m5F1 Tissue Staining with m5F1

The expression of m5F1 target was investigated by immunohistochemistry in paraffin-embedded primary tumor tissue samples from patients with colorectal cancer (n=59). Tissue arrays of paraffin-embedded human colon and rectum cancer tissues were obtained from SuperBioChips Laboratories (Human tissue array, Cat no. CD1). Standard staining procedures were used for immunohistochemistry according to manufacturer's instruction (VECTASTAIN® Elite ABC® Kit, Vector Laboratories). All sections were heated at 58° C. for 1 hr, deparaffinized with xylene for five times, and rehydrated in a series of ethanol with decreasing concentration. After blocking with normal serum (VECTASTAIN®, PK6102) for 1 hr, the sections were incubated with the m5F1 at a concentration of 1 µg/ml for 1 hr at RT and subsequently with the secondary, biotinylated anti-mouse antibody (VECTASTAIN®, PK6102). Sections were then incubated with a streptavidin-biotin complex (VECTASTAIN®, PK6102). The slides were developed with diaminobenzidine solution. Finally the slides were counterstained with haematoxylin, dehydrated, cleared, and mounted in 50% glycerol in PBS.

Assessment of Grading

Antigen expression in each tissue section was evaluated by two independent observers and the staining with 5F1 was graded using an empirical semi-quantitative system: −, negative; +−, weak staining; +, moderate staining; ++, strong staining.

Results

In all sections, m5F1 staining was predominantly membranous. In total, 31 out of the 59 tumour specimens (52.5%) showed positive staining for 5F1 target, among them, 27 (45.8%) showed strong levels of expression. 19 samples (32.2%) showed negative staining for m5F1 target expression. A summary of staining results across all colorectal cancer samples tested is shown in Table 6 below. These data indicate that antibody m5F1 may be used for diagnosing colorectal cancer.

TABLE 6

Frequency of 5F1 target expression in human colorectal cancers
colorectal cancer sample/m5F1 staining result

| 1++ | 2++ | 3++ | 4− | 5++ | 6+− | 7++ | 8− | 9++ | 10++ |
|---|---|---|---|---|---|---|---|---|---|
| 11++ | 12− | 13++ | 14+− | 15− | 16− | 17++ | 18++ | 19+− | 20++ |
| 21+ | 22+− | 23+ | 24− | 25++ | 26− | 27− | 28− | 29++ | 30++ |
| 31+− | 32− | 33− | 34++ | 35++ | 36− | 37− | 38++ | 39++ | 40++ |
| 41+ | 42++ | 43− | 44− | 45− | 46− | 47+− | 48++ | 49− | 50+ |
| 51++ | 52++ | 53+− | 54++ | 55++ | 56++ | 57+− | 58+− | 59− | 60 carbon |

++27/59 (45.76%)
+4/59 (6.78%)
+−9/59 (15.25%)
−19/59 (32.20%)

Example 9 m5F1 Binds to Recombinant Human CEA (rhCEA) and CD43 (rhCD43) Expressed by COLO 205, but does not Recognize rhCEA or rhCD43 Expressed by COS-7 Cells Protein Sample Preparation Immuno-Precipitation for recombinant Flag-tagged CEA in COLO 205 and COS cells: The cDNA coding for full length CEA protein (35~702aa) was cloned into plasmid pFlag-CMV-1. The engineered plasmid DNA was introduced into COLO 205 (for stable cell line engineering) by electroporation or COS cells (for transient expression experiment) by lipofectamine™ 2000 (Invitrogen, Catalog #11668-019). Antigen expressing cells were collected and lysed in lysis buffer (50 mM Tris-HCl, pH 8.5, 150 mM NaCl, 1% NP40) containing protease inhibitors (Roche, Catalog #11836145001). The supernatant of cell lysates were incubated with anti-Flag® (M2, Stratagene, Catalog #200472) coupled protein G Sepharose® beads (GE Healthcare, Catalog #17-0618-02) for 2 hours at 4° C. The protein G Sepharose® beads were then washed three times with lysis buffer. The protein G Sepharose® beads containing IP products were used as samples for SDS-PAGE and Western blot.

Soluble recombinant protein purification for Cr1-tagged CD43 expressed in COLO 205 cells: The cDNA coding for the extracellular domain of CD43 protein was cloned into the modified pcDNA3 plasmid which contains N-terminal Flag and C-terminal Cr1 tags. The engineered plasmid DNA was introduced into COLO 205 cells by electroporation for stable cell line development. The soluble recombinant hCD4320-253 expressed by COLO 205 contains N-terminal 3×Flag tag and C-terminal Cr1 tag. The soluble protein were purified with protein A Sepharose® beads (GE Healthcare, Catalog #17-1279-02). After eluted with glycine buffer and dialyzed against PBS, the protein samples were stored at −20° C. for future usage.

Whole cell lysate for CD43 transiently expressed in COS cell: A construct containing full-length human CD43 (in pcDNA3.1myc-His) was introduced into COS cells by Lipofectamine™ 2000 (Invitrogen, Catalog #11668-019). Cells were lysed with RIPA buffer (50 mM Tris-HCl, pH 7.4, 150 mM NaCl, 1 mM EDTA, 0.25% SDS, 1% NP-40) containing protease inhibitors, and centrifugeg at 21,900 g at 4° C. for 10 min to collect the supernatant. After Bio-Rad quantification, sufficient amount of protein lysates were loaded on SDS-PAGE for Western blot analysis.

Western Blot Analysis

After adding sample buffer, the protein samples were boiled at 95° C., loaded on a SDS-PAGE mini-gel, and then transferred to NC paper (GE Healthcare, Hybond™-ECL, Catalog #RPN303D). After blocking the membranes with 5% non-fat milk in TBS, 1st antibodies were added. The binding of 1st antibodies were detected by HRP conjugated 2nd antibody (NEN Life Science, HRP-goat anti-mouse IgG, Catalog #NEF822, or Southern Biotech, HRP-goat anti-mouse Ig, Catalog #1010-05) and developed with ECL Western blotting detection reagents (GE Healthcare, Catalog #RPN2106).

Results

Figure 11:
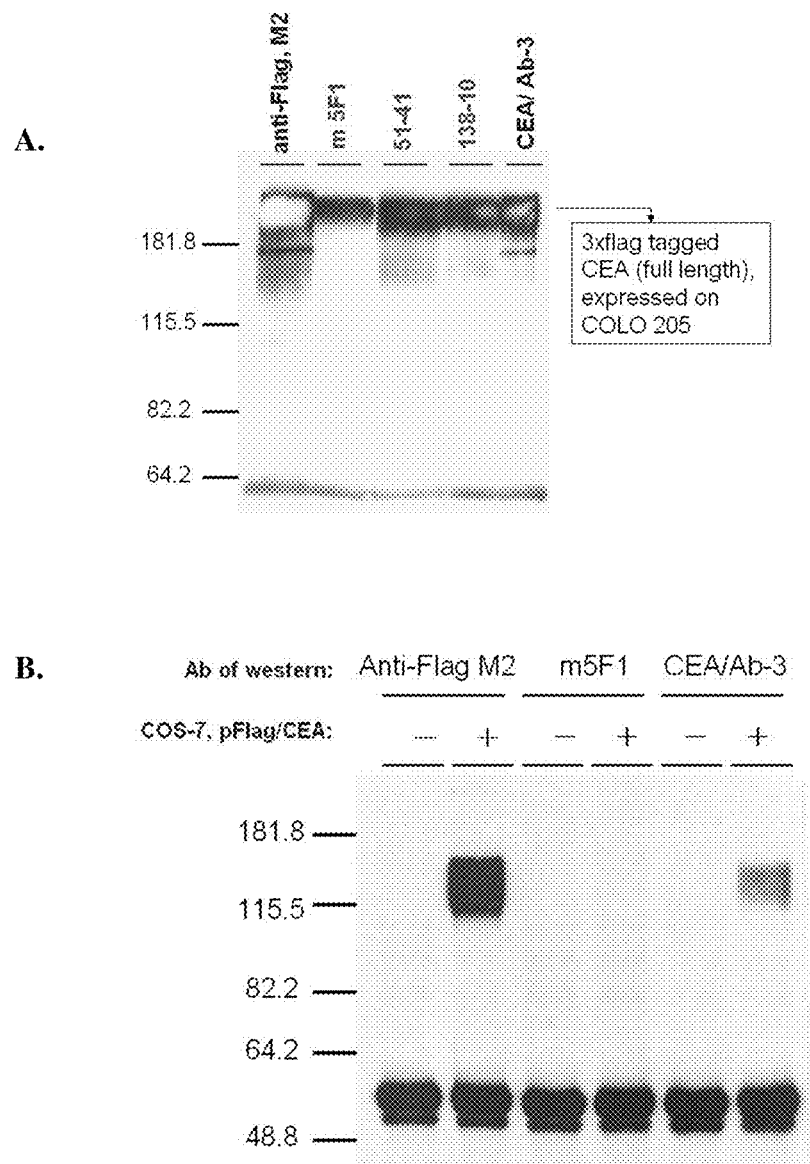
FIG. 11 shows that m5F1 binds to recombinant human CEA (rhCEA) expressed on COLO 205 cells, but does not recognize rhCEA expressed on COS-7 cells.

In the experiment shown in FIG. 11A, cell lysates of COLO 205 cells expressing rhCEA were immunoprecipated with anti-Flag® antibody and the immunoprecipitated proteins were run on SDS-PAGE and transferred to NC paper. NC paper was blotted with various antibodies: anti-Flag®, m5F1, 50-14, 51-41, 138-10, 186-14, 280-6, or anti-CEA antibody (CEA/Ab-3; clone name COL-1 from NeoMarker Cat. MS-613-P1ABX). Data in FIG. 11A showed that m5F1, 51-41, and 138-10 recognized rhCEA expressed by COLO 205 cells.

In the experiment shown in FIG. 11B, cell lysates of COS-7 cells expressed rhCEA were immunoprecipated with anti-Flag® antibody and the immunoprecipitated proteins were run on SDS-PAGE and transferred to NC paper. NC paper was blotted with various antibodies: anti-Flag®, m5F1, or anti-CEA (CEA/Ab-3). Data in FIG. 11B showed that m5F1 did not bind to rhCEA expressed by COS-7 cells.

Figure 12:
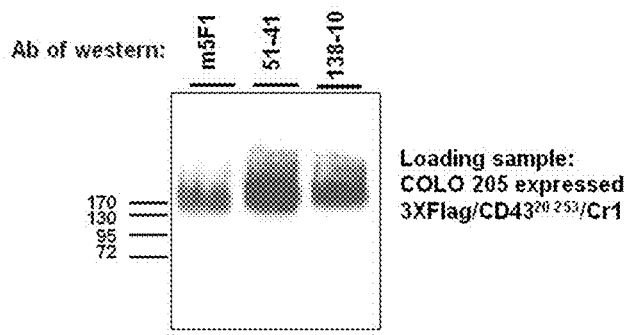
FIG. 12 shows that m5F1 binds to recombinant CD43 (rhCD43) expressed on COLO 205 cells, but does not recognize rhCD43 expressed on COS-7 cells.
Figure 12:
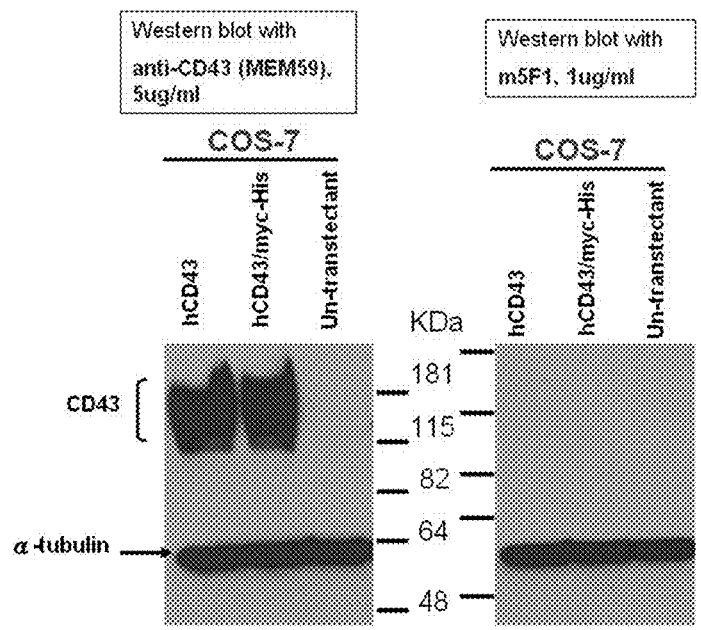

In the experiment shown in FIG. 12A, soluble proteins expressed by COLO 205 were purified with protein A Sepharose® beads, and were run on SDS gel and transferred to NC paper. NC paper was blotted with various antibodies: m5F1, 51-41, or 138-10. Data in FIG. 12A showed m5F1, 51-41, and 138-10 recognized rhCD43 expressed by COLO 205 cells.

In the experiment shown in FIG. 12B, soluble proteins expressed in COLO 205 were purified with protein A Sepharose®, and were run on SDS-PAGE and transferred to NC paper. NC paper was blotted with anti-CD43 (MEM59) (left panel) or m5F1 (right panel). Data in FIG. 12B showed m5F1 did not recognize rhCD43 expressed by COS-7 cells.

These data indicate that the epitope recognized by m5F1 includes a post-translational modification specific for certain cell types.

Example 10

The Epitope Recognized by m5F1, 51-41, and 138-10 Includes a Lewis$^a$ (Le$^a$) Structure and is Fucose Dependent Glycosidase Treatment Recombinant human CEA (rhCEA) was produced by expression human CEA protein in COLO 205 cells. The cDNA coding for the rhCEA (CEA-N-A2), which is a fusion having amino acids 35-145 (N domain) and amino acids 324-415 (A2 domain) of CEA, was cloned into modified pcDNA3 plasmid which contains Flag tag. Amino acid residue position of CEA is based on the amino acid position in the pre-protein. The engineered plasmid DNA was introduced into COLO 205 cells for stable cell line engineering by electroporation. Recombinant CEA protein was purified from cell culture supernatant of the recombinant-CEA expressing stable cell lines using anti-Flag® antibody.

For each reaction, about 1.8 μg recombinant protein (rhCEA) was incubated with different amount (0, 0.01, 0.03, or 0.1 mU) of α-1→(2,3,4)-Fucosidase solution from *Xanthomonas* sp. (Sigma, Catalog #F 1924) at 37° C. for 20 hours. After treatment, the protein samples were loaded on SDS-PAGE for Coomassie blue staining (FIG. 13 left panel) or Western blot detection (FIG. 13 right panel) with m5F 1.

Figure 13:
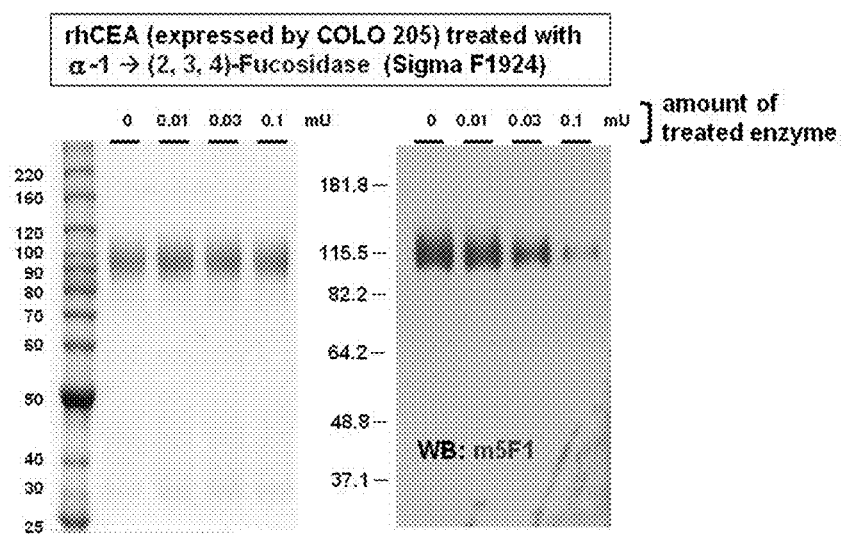
FIG. 13 shows that m5F1 antibody recognizes a fucose dependent glyco-epitope. rhCEA expressed by COLO 205 cells were treated with 0, 0.01, 0.03, 0.1 mU of α-1→(2,3,4)-Fucosidase. After treatment, proteins were run on SDS-PAGE, and then Coomassie blue stained (right panel) or Western blotted with m5F1 antibody.

As shown in FIG. 13, binding of m5F1 to the rhCEA decreased when the antigen was treated with α-1→(2,3,4)-Fucosidase, indicating m5F1 recognize a fucose sensitive glyco-epitope.

Oligosaccharides Competition Assay

Figure 14:
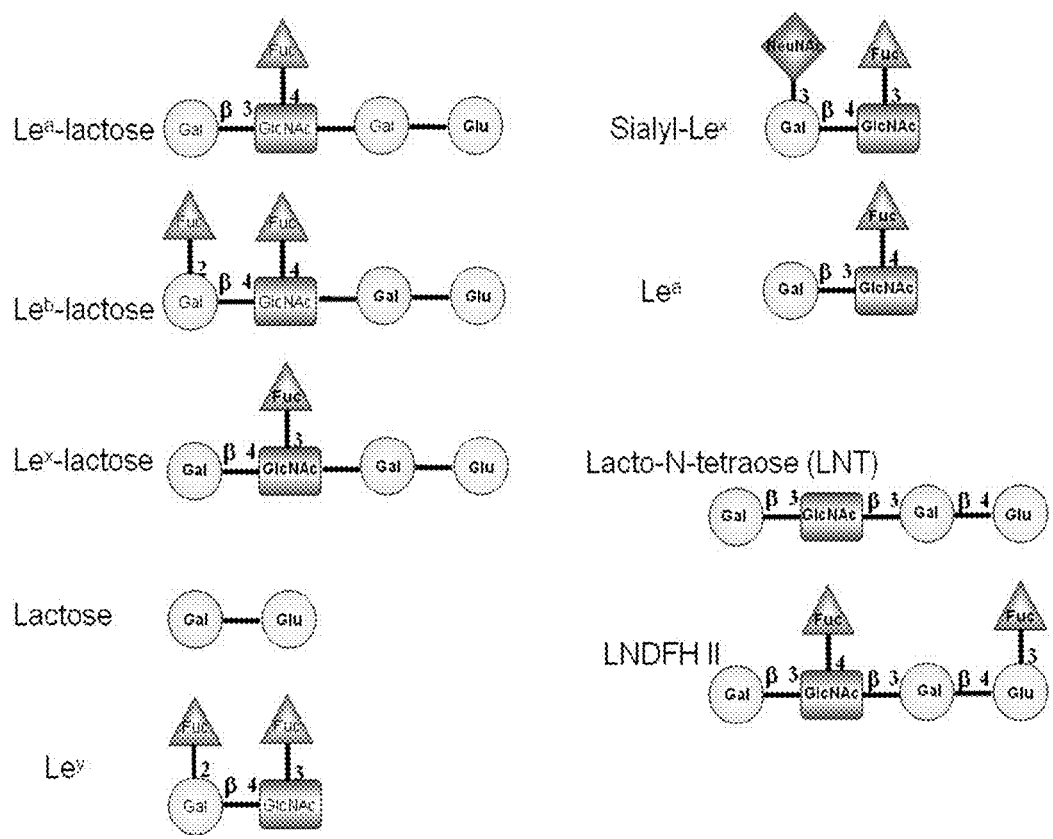
FIG. 14 shows the structure of Lewis$^a$-lactose (Le$^a$-lactose), Lewis$^b$-lactose (Le$^b$-lactose), Lewis$^x$-lactose (Le$^x$-lactose), lactose, Lewis$^y$(Le$^y$), Sialyl-Lewis$^x$ (Sialyl-Le$^x$), Lewis$^a$ (Le$^a$), Lacto-N-tetraose (LNT), and Lecto-N-difucohexaose II (LNDFH II).

To further test the glyco-epitope recognized by m5F1, competition assays with various oligosaccharides were conducted. Oligosaccharides were purchased (Lewis$^a$ from Sigma Catalog #03499, Lewis$^b$-lactose from Sigma Catalog #L7033, Lewis$^x$-lactose from Sigma Catalog #L7777, Lewis$^y$ from Sigma Catalog #L7784, Sialyl-Lewis$^x$ from Sigma Catalog #S1782, Lacto-N-tetraose from Sigma Catalog #L6770, Lecto-N-difucohexaose II from Sigma Catalog #L6645, Lewis$^a$ from Calbiochem Catalog #434626, and β-lactose form Sigma Catalog #L3750) and dissolved in PBS. The structures of these oligosaccharides are shown in FIG. 14. Oligosaccharides (at 1 mM final concentration) were added into different wells containing 2×10$^5$ COLO 205 cells, followed by the addition of indicated antibodies (m5F1, 51-41, or 138-10; each at 0.25 ug/ml). After one hour incubation at 4° C., the supernatant was discarded and secondary antibodies (Southern Biotech, RPE-goat anti-mouse IgG, Catalog #1032-09, or Southern Biotech, RPE-goat anti-mouse IgM, Catalog #1022-09) were added. And the cellular binding signals were detected with flow cytometry analysis.

Figure 15:
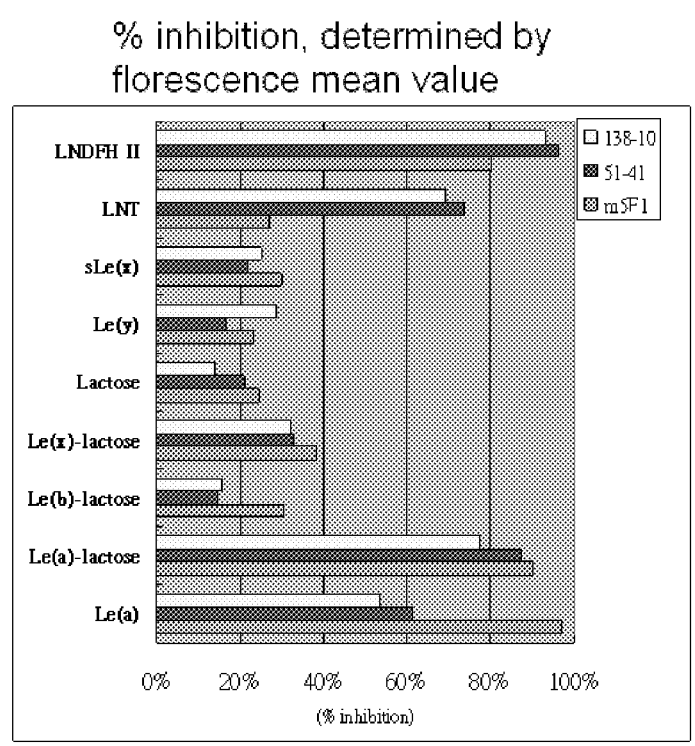
FIG. 15 shows the results of binding inhibition assays by adding oligosaccharides to compete m5F1, 138-10, and 51-41 binding to COLO 205 cells. Oligosaccharides (LNDFH II, LNT, sLe(x), Le(y), Lactose, Le(x)-lactose, Le(b)-lactose, Le(a)-lactose, or Le(a); each at 1 mM) were added into different wells containing 2×10$^5$ COLO 205 cells, followed by the addition of the antibodies (138-10, 51-41, or m5F1) or no antibodies as control. Binding of the antibodies to COLO 205 cells were measured by flow cytometry analysis. Binding inhibition by the oligosaccharides for each antibody is shown as percentage of inhibition determined by florescence mean value in the Figure.

As shown in FIG. 15, LNDFH II, Le(a)-lactose, and Le(a) all inhibited, at various levels, binding of antibodies m5F1, 51-41, and 138-10 to COLO 205 cells; and LNT also inhibited binding of antibodies 51-41 and 138-10, but did not significantly inhibit binding of m5F1 to COLO 205 cells. This indicates that the epitope recognized by these antibodies may include a Le$^a$ or similar structure, and is fucose sensitive. In addition, m5F1 antibody has higher dependency on fucose than antibody 51-41 and 138-10.

Although the foregoing invention has been described in some detail by way of illustration and example for purposes of clarity of understanding, the descriptions and examples should not be construed as limiting the scope of the invention.

REFERENCES

Laos, S., Baeckstrom, D, and Hansson, G. C. (2006) Inhibition of NF-kappaB activation and chemokine expression by the leukocyte glycoprotein, CD43, in colon cancer cells. Int. J. Oncol. 28(3):695-704.

Fuhlbrigge, R. C., King, S. L., Sackstein, R., and Kupper, T S. (2006) CD43 is a ligand for E-selectin on CLA+ human T cells. Blood. 15; 107(4):1421-6.

Matsumoto, M., Atarashi, K., Umemoto, E., Furukawa, Y., Shigeta, A., Miyasaka, M., and Hirata, T. (2005) CD43 functions as a ligand for E-Selectin on activated T cells. J. Immunol. 15; 175(12):8042-50.

Pimenidou, A., Madden, L. A., Topping, K. P., Smith, K. A., Monson, J. R., and Greenman, J. (2004) Novel CD43 specific phage antibodies react with early stage colorectal tumours. Oncol. Rep. 11(2):327-31.

Kadaja, L., Laos, S., and Maimets, T. (2004) Overexpression of leukocyte marker CD43 causes activation of the tumor suppressor proteins p53 and ARF. Oncogene. 19; 23(37): 2523-2530.

Fernandez-Rodriguez, J., Andersson, C. X., Laos, S., Baeckstrom, D., Sikut, A., Sikut, R., and Hansson, G. C. (2002) The leukocyte antigen CD43 is expressed in different cell lines of nonhematopoietic origin. Tumour Biol. 23(4): 193-201.

Cermak, L., Simova, S., Pintzas, A., Horejsi, V., and Andera, L. (2002) Molecular mechanisms involved in CD43-mediated apoptosis of TF-1 cells. Roles of transcription Daxx expression, and adhesion molecules. J Biol Chem. 8; 277(10): 7955-61.

Carlow, D. A., Corbel, S. Y., and Ziltener, H. J. (2001) Absence of CD43 fails to alter T cell development and responsiveness. J Immunol. 166(1):256-61.

Nieto, M., Rodriguez-Fernandez, J. L., Navarro, F., Sancho, D., Frade, J. M., Mellado, M., Martinez-A, C., Cabanas, C., and Sanchez-Madrid, F. (1999) Signaling through CD43 induces natural killer cell activation, chemokine release, and PYK-2 activation. Blood. 94(8):2767-77.

Sikut, R., Andersson, C. X., Sikut, A., Fernandez-Rodriguez, J., Karlsson, N. G., and Hansson, G. C. (1999) Detection of CD43 (leukosialin) in colon adenoma and adenocarcinoma by novel monoclonal antibodies against its intracellular domain. Int. J. Cancer. 82(1):52-8.

Lopez, S., Seveau, S., Lesavre, P., Robinson, M. K., and Halbwachs-Mecarelli, L. (1998) CD43 (sialophorin, leukosialin) shedding is an initial event during neutrophil migration, which could be closely related to the spreading of adherent cells. Cell Adhes. Commun. 5(2):151-60.

Stockton, B. M., Cheng, G., Manjunath, N., Ardman, B., and von Andrian, U. H. (1998) Negative regulation of T cell homing by CD43. Immunity. 8(3):373-81.

McEvoy, L. M., Jutila, M. A., Tsao, P. S., Cooke, J. P., and Butcher, E. C. (1997) Anti-CD43 inhibits monocyte-endothelial adhesion in inflammation and atherogenesis. Blood. 90(9):3587-94.

Baeckstrom, D. (1997) Post-translational fate of a mucin-like leukocyte sialoglycoprotein (CD43) aberrantly expressed in a colon carcinoma cell line. J Biol Chem. 272 (17):11503-9.

McEvoy, L. M., Sun, H., Frelinger, J. G., and Butcher, E. C. (1997) Anti-CD43 inhibition of T cell homing. J Exp Med. 185(8):1493-8.

Brown, T. J., Shuford, W. W., Wang, W. C., Nadler, S. G., Bailey, T. S., Marquardt, H., and Mittler, R. S. (1996) Characterization of a CD43/leukosialin-mediated pathway for inducing apoptosis in human T-lymphoblastoid cells. J Biol Chem. 271(44):27686-95.

Santamaria, M., Lopez-Beltran, A., Toro, M., Pena, J., and Molina, I. J. (1996) Specific monoclonal antibodies against leukocyte-restricted cell surface molecule CD43 react with nonhematopoietic tumor cells. Cancer Res. 56(15):3526-9.

Bazil, V., Brandt, J., Chen, S., Roeding, M., Luens, K., Tsukamoto, A., and Hoffman, R. (1996) A monoclonal antibody recognizing CD43 (leukosialin) initiates apoptosis of human hematopoietic progenitor cells but not stem cells. Blood. 87(4):1272-81.

Manjunath, N., Correa, M., Ardman, M., and Ardman, B. (1995) Negative regulation of T-cell adhesion and activation by CD43. Nature. 377(6549):535-8

Nong, Y. H., Remold-O'Donnell, E., LeBien, T. W., and Remold, H. G. (1989) A monoclonal antibody to sialophorin (CD43) induces homotypic adhesion and activation of human monocytes. J Exp Med. 170(1):259-67.

Mentzer, S. J., Remold-O'Donnell, E., Crimmins, M. A., Bierer, B. E., Rosen, F. S., and Burakoff, S. J. (1987) Sialophorin, a surface sialoglycoprotein defective in the Wiskott-Aldrich syndrome, is involved in human T lymphocyte proliferation. J Exp Med. 165(5):1383-92.

Pallant, A., Eskenazi, A., Mattei, M G., Fournier, R. E. K., Carlsson, S. R., Fukuda, M., and Frelinger, J. G. (1989) Characterization of cDNA encoding human leukosialin and localization of the leukosialin gene to chromosome 16. Proc. Natl. Acad. Sci. USA 86:1328-32.

Shelley, C. S., Remold-O'Donnell, E., Davis III, A. E., Bruns, G. A. P., Rosen, F. S., Carroll, M. C., and Whitehead, A. S. (1989) Molecular characterization of sialophorin (CD43), the lymphocyte surface sialoglycoprotein defective in Wiskott-Aldrich syndrome. Proc. Natl. Acad. Sci. USA 86: 2819-23.

What is claimed is:

1. A method for treating colorectal or gastric cancer in an individual having cancer comprising administering to the individual an effective amount of a composition comprising a monoclonal antibody, wherein the antibody recognizes an epitope on the extracellular surface of a human CD43 expressed by a human colorectal or human gastric cancer cell and comprises a heavy chain variable region comprising the three complementarity determining regions from the amino acid sequence of SEQ ID NO:1, and a light chain variable region comprising the three complementarity determining regions from the amino acid sequence of SEQ ID NO:2.

2. The method of claim 1, wherein the antibody comprises the heavy chain variable region sequence from the amino acid sequence of SEQ ID NO:1, and the light chain variable region sequence from the amino acid sequence of SEQ ID NO:2.

3. A method for treating colorectal or gastric cancer in an individual having cancer comprising administering to the individual an effective amount of a composition comprising a monoclonal antibody, wherein the antibody recognizes an epitope on the extracellular surface of a human CD43 expressed by a human colorectal or human gastric cancer cell and comprises the heavy chain variable region sequence from the amino acid sequence of SEQ ID NO:7, and the light chain variable region sequence from the amino acid sequence of SEQ ID NO:8.

4. A method for treating colorectal or gastric cancer in an individual comprising administering to the individual an amount of a monoclonal antibody and an amount of another anti-cancer agent, whereby the monoclonal antibody and the anti-cancer agent in conjunction provides effective treatment of cancer in the individual, wherein the antibody recognizes an epitope on the extracellular surface of a human CD43 expressed by a human colorectal or human gastric cancer cell and comprises a heavy chain variable region comprising the three complementarity determining regions from the amino acid sequence of SEQ ID NO:1, and a light chain variable region comprising the three complementarity determining regions from the amino acid sequence of SEQ ID NO:2.

5. The method of claim 4, wherein the antibody comprises the heavy chain variable region sequence from the amino acid sequence of SEQ ID NO:1, and the light chain variable region sequence from the amino acid sequence of SEQ ID NO:2.

6. A method for treating colorectal or gastric cancer in an individual comprising administering to the individual an amount of a monoclonal antibody and an amount of another anti-cancer agent, whereby the monoclonal antibody and the anti-cancer agent in conjunction provides effective treatment of cancer in the individual, wherein the antibody recognizes an epitope on the extracellular surface of a human CD43 expressed by a human colorectal or human gastric cancer cell and comprises the heavy chain variable region sequence from the amino acid sequence of SEQ ID NO:7, and the light chain variable region sequence from the amino acid sequence of SEQ ID NO:8.

7. The method of claim 1, wherein the antibody is conjugated to a cytotoxin.

8. The method of claim 1, wherein the antibody is a humanized antibody.

9. The method of claim 1, wherein the individual is a human.

10. The method of claim 4, wherein the antibody is conjugated to a cytotoxin.

11. The method of claim 4, wherein the antibody is a humanized antibody.

12. The method of claim 4, wherein the individual is a human.

13. The method of claim 1, wherein the antibody is a chimeric antibody.

14. The method of claim 4, wherein the antibody is a chimeric antibody.

15. The method of claim 7, wherein the cytotoxin is selected from the group consisting of paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin.

16. The method of claim 10, wherein the cytotoxin is selected from the group consisting of paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin.

17. The method of claim 3, wherein the antibody is conjugated to a cytotoxin.

18. The method of claim 17, wherein the cytotoxin is selected from the group consisting of paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin.

19. The method of claim 3, wherein the individual is human.

20. The method of claim 6, wherein the antibody is conjugated to a cytotoxin.

21. The method of claim 20, wherein the cytotoxin is selected from the group consisting of paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin.

22. The method of claim 6, wherein the individual is human.

23. The method of claim 1, wherein the cancer is colorectal cancer.

24. The method of claim 1, wherein the cancer is gastric cancer.

25. The method of claim 3, wherein the cancer is colorectal cancer.

26. The method of claim 3, wherein the cancer is gastric cancer.

27. The method of claim 4, wherein the cancer is colorectal cancer.

28. The method of claim 4, wherein the cancer is gastric cancer.

29. The method of claim 6, wherein the cancer is colorectal cancer.

30. The method of claim 6, wherein the cancer is gastric cancer.

* * * * *